(12) United States Patent
Williams et al.

(10) Patent No.: US 11,448,650 B2
(45) Date of Patent: Sep. 20, 2022

(54) METHODS FOR DIAGNOSING HIGH-RISK CANCER USING POLYSIALIC ACID AND ONE OR MORE TISSUE-SPECIFIC BIOMARKERS

(71) Applicant: Glyca Inc., Calgary (CA)

(72) Inventors: Karla Williams, Vancouver (CA); Hon Sing Leong, Rochester, MN (US)

(73) Assignee: GLYCA INC., Calgary (CA)

( * ) Notice: Subject to any disclaimer, the term of this patent is extended or adjusted under 35 U.S.C. 154(b) by 166 days.

(21) Appl. No.: 16/611,596

(22) PCT Filed: May 8, 2018

(86) PCT No.: PCT/CA2018/050549
§ 371 (c)(1),
(2) Date: Nov. 7, 2019

(87) PCT Pub. No.: WO2018/205023
PCT Pub. Date: Nov. 15, 2018

(65) Prior Publication Data
US 2020/0116728 A1    Apr. 16, 2020

Related U.S. Application Data

(60) Provisional application No. 62/503,256, filed on May 8, 2017.

(51) Int. Cl.
*G01N 1/00* (2006.01)
*G01N 33/574* (2006.01)

(52) U.S. Cl.
CPC . *G01N 33/57488* (2013.01); *G01N 33/57415* (2013.01); *G01N 33/57434* (2013.01); *G01N 2400/00* (2013.01)

(58) Field of Classification Search
CPC ............................................... G01N 33/57488
USPC ........................................................ 435/7.23
See application file for complete search history.

(56) References Cited

U.S. PATENT DOCUMENTS

| | | |
|---|---|---|
| 2004/0157227 A1 | 8/2004 | Chopin et al. |
| 2012/0309018 A1 | 12/2012 | Skolnick et al. |
| 2014/0056807 A1 | 2/2014 | Di Vizio et al. |
| 2014/0113310 A9 | 4/2014 | Skolnick et al. |
| 2014/0228233 A1 | 8/2014 | Pawlowski et al. |
| 2015/0133327 A1 | 5/2015 | Leong et al. |

FOREIGN PATENT DOCUMENTS

| | | |
|---|---|---|
| WO | WO-2013/155605 A1 | 10/2013 |
| WO | WO-2013/155633 A1 | 10/2013 |

OTHER PUBLICATIONS

Gandaglia et al (International Journal of Urology, 2015, 22: 89-95).*
Tanaka et al (Cancer Research, 2000, 60: 3072-3080).*
Su et al (Radiation Oncology, 2014, 9(290): 1-7).*
Wang et al (International Journal of Molecular Medicine, 2016, 37: 197-206).*
Davidson et al (CMAJ Open, 2013, 1(4): E134-E141).*
Shenkier et al (CMAJ, 2004, 170(6): 983-994).*
Paner et al (Arch Pathol Lab Med, 2008, 132: 1388-1396).*
Thompson et al (The Journal of Urology, 2009, 181: 956-962).*
Al-Saraireh et al., "Pharmacological Inhibition of polysialyltransferase ST8SiaII Modulates Tumour Cell Migration," PLoS One. 8(8):e73366 (2013) (12 pages).
Aristizábal-Pachón et al., "Detection of human mammaglobin A mRNA in peripheral blood of breast cancer patients before treatment and association with metastasis," J Egypt Natl Canc Inst. 27(4):217-22 (2015).
Biggs et al., "Prostate extracellular vesicles in patient plasma as a liquid biopsy platform for prostate cancer using nanoscale flow cytometry," Oncotarget. 7(8):8839-49 (2016).
Brett et al., "Extracellular vesicles such as prostate cancer cell fragments as a fluid biopsy for prostate cancer," Prostate Cancer Prostatic Dis. 18(3):213-20 (2015).
Carter et al., "Gleason Score 6 Adenocarcinoma: Should It be Labeled as Cancer?," J Clin Oncol. 30(35):4294-96 (2012).
Chandler et al., "A new microparticle size calibration standard for use in measuring smaller microparticles using a new flow cytometer," J Thromb Haemost. 9(6):1216-24 (2011).
Colley et al., "Polysialic acid: biosynthesis, novel functions and applications," Crit Rev Biochem Mol Biol. 49(6):498-532 (2014) (36 pages).
Conchonaud et al., "Polysialylation Increases Lateral Diffusion of Neural Cell Adhesion Molecule in the Cell Membrane," J Biol Chem. 282(36):26266-74 (2007) (10 pages).
Cooperberg et al., "The Changing Face of Low-risk Prostate Cancer: Trends in Clinical Presentation and Primary Management," available in PMC Dec. 4, 2010, published in final edited form as: J Clin Oncol. 22(11):2141-49 (2004) (17 pages).
Curreli et al., "Polysialylated Neuropilin-2 Is Expressed on the Surface of Human Dendritic Cells and Modulates Dendritic Cell-T Lymphocyte Interactions," J Biol Chem. 282(42):30346-56 (2007) (12 pages).
Daniel et al., "A nude mice model of human rhabdomyosarcoma lung metastases for evaluating the role of polysialic acids in the metastatic process," Oncogene. 20(8):997-1004 (2001).
Di Vizio et al., "Large Oncosomes in Human Prostate Cancer Tissues and in the Circulation of Mice with Metastatic Disease," Am J Pathol. 181(5):1573-84 (2012).
Draisma et al., "Lead Time and Overdiagnosis in Prostate-Specific Antigen Screening: Importance of Methods and Context," J Natl Cancer Inst. 101(6):374-83 (2009).
Fendler et al., "$^{68}$Ga-PSMA PET/CT Detects the Location and Extent of Primary Prostate Cancer," J Nucl Med. 57(11):1720-25 (2016) (7 pages).
Giza et al., "Polysialic acid: A veteran sugar with a new site of action in the brain," PNAS. 107(23):10335-336 (2010).

(Continued)

*Primary Examiner* — Sean E Aeder
(74) *Attorney, Agent, or Firm* — Hogan Lovells US LLP

(57) ABSTRACT

Described herein are methods for diagnosing high-risk cancer in a subject by detecting PolySialic Acid (polySia) in a biological sample obtained from the subject, or by detecting polySia and one or more tissue-specific markers in a biological sample obtained from the subject.

6 Claims, 42 Drawing Sheets

(56) References Cited

OTHER PUBLICATIONS

Gross et al., "Isolation of Bacteriophages Specific for the K1 Polysaccharide Antigen of *Escherichia coli*," J Clin Microbiol. 6(6):548-50 (1977).
Heimburg-Molinaro et al., "Cancer Vaccines and Carbohydrate Epitopes," available in PMC Nov. 8, 2012, published in final edited form as: Vaccine. 29(48):8802-26 (2011) (57 pages).
Hromatka et al., "Polysialic acid enhances the migration and invasion of human cytotrophoblasts," Glycobiology. 23(5):593-602 (2013).
Humphrey, "Gleason grading and prognostic factors in carcinoma of the prostate," Mod Pathol. 17(3):292-306 (2004).
Ihlaseh-Catalano et al., "STEAP1 protein overexpression is an independent marker for biochemical recurrence in prostate carcinoma," Histopathology. 63(5): 678-85 (2013).
International Search Report and Written Opinion for International Application No. PCT/CA2018/050549, dated Jul. 16, 2018 (10 pages).
Julich et al., "Extracellular vesicle profiling and their use as potential disease specific biomarker," Front Immunol. 5(413):1-6 (2014).
Klobučar et al., "Expression of polysialic acid in primary laryngeal squamous cell carcinoma," Life Sci. 173:73-9 (2017).
Klotz et al., "Clinical Results of Long-Term Follow-Up of a Large, Active Surveillance Cohort With Localized Prostate Cancer," Journal of Clinical Oncology. 28(1):126-131 (2010).
Klotz et al., "Long-Term Follow-Up of a Large Active Surveillance Cohort of Patients With Prostate Cancer," Journal of Clinical Oncology. 33(3):272-77 (2015) (10 pages).
Lalonde et al., "Tumour genomic and microenvironmental heterogeneity for integrated prediction of 5-year biochemical recurrence of prostate cancer: a retrospective cohort study," Lancet Oncol. 15:1521-32 (2014).
Leach et al., "The Dilemma of Prostate-Specific Antigen Testing," available in PMC Sep. 13, 2016, published in final edited form as: Arch Intern Med. 172(11):835-36 (2012) (3 pages).
Leong et al., "Imaging the Impact of Chemically Inducible Proteins on Cellular Dynamics In Vivo" PLoS ONE. 7(1):e30177 (2012) (12 pages).
Leong et al., "Invadopodia Are Required for Cancer Cell Extravasation and Are a Therapeutic Target for Metastasis," Cell Reports. 8:1558-70 (2014) (20 pages).
Li et al., "Human mammaglobin: A specific marker for breast cancer prognosis," J Buon 21(1):35-41 (2016).
Muralidharan-Chari et al., "Microvesicles: mediators of extracellular communication during cancer progression," J Cell Sci. 123:1603-1611 (2010).
Nakata et al., "Degree of Polymerization (DP) of Polysialic Acid (PolySia) on Neural Cell Adhesion Molecules (N-CAMs)," The Journal of Biological Chemistry. 280(46):38305-16 (2005).
Padda et al., "Nanoscale flow cytometry to distinguish subpopulations of prostate extracellular vesicles in patient plasma," Prostate. 79(6):592-603 (2019) (12 pages).
Peinado et al., "Melanoma exosomes educate bone marrow progenitor cells toward a pro-metastatic phenotype through MET," available in PMC May 6, 2013, published in final edited form as: Nat Med. 18(6): 883-91 (2012) (20 pages).
Pinkhasov et al., "Complications following prostate needle biopsy requiring hospital admission or emergency department visits—experience from 1000 consecutive cases," BJU Int. 110(3):369-74 (2012).

Saldova et al., "Core fucosylation and alpha2-3 sialylation in serum N-glycome is significantly increased in prostate cancer comparing to benign prostate hyperplasia," Glycobiology. 21(2):195-205 (2011).
Schnaar et al., "Sialic Acids in the Brain: Gangliosides and Polysialic Acid in Nervous System Development, Stability, Disease, and Regeneration," Physiol Rev. 94(2):461-518 (2014).
Schreiber et al., "Polysialylated NCAM Represses E-Cadherin-Mediated Cell-Cell Adhesion in Pancreatic Tumor Cells," Gastroenterology. 134(5):1555-66 (2008).
Sokoll et al., "A Prospective, Multicenter, NCI EDRN Study of [-2]proPSA: Improving Prostate Cancer Detection and Correlating with Cancer Aggressiveness," available in PMC May 1, 2011, published in final edited form as: Cancer Epidemiol Biomarkers Prev. 19(5):1193-1200 (2010) (17 pages).
Suzuki et al., "Polysialic acid facilitates tumor invasion by glioma cells," Glycobiology. 15(9):887-94 (2005).
Tajiri et al., "Oligosaccharide profiles of the prostate specific antigen in free and complexed forms from the prostate cancer patient serum and in seminal plasma: a glycopeptide approach," Glycobiology. 18(1):2-8 (2008).
Verma et al., "Extracellular vesicles: potential applications in cancer diagnosis, prognosis, and epidemiology," BMC Clin Pathol. 15:6 (2015) (9 pages).
Williams et al., "Polysialic Acid as a Novel Carbohydrate Biomarker for Intermediate and High-risk Prostate Cancer," The Journal of Urology. 199(4S):e1150 (2018) (1 page). Abstract PD60-10.
Witwer et al., "Standardization of sample collection, isolation and analysis methods in extracellular vesicle research," J Extracell Vesicles. 2:20360 (2013) (25 pages).
Albertsen et al., "20-Year Outcomes Following Conservative Management of Clinically Localized Prostate Cancer." JAMA. 293(17): 2095-101 (2005).
Burgess et al., "Polysialic Acid Regulates the Clustering, Migration, and Neuronal Differentiation of Progenitor Cells in the Adult Hippocampus," Dev Neurobiol. 68(14):1580-90 (2008).
Loblaw et al., "Comparing Prostate Specific Antigen Triggers for Intervention in Men With Stable Prostate Cancer on Active Surveillance," J Urol. 184(5):1942-6 (2010).
Wolf et al., "Three Conformational Antibodies Specific for Different PSMA Epitopes Are Promising Diagnostic and Therapeutic Tools for Prostate Cancer," Prostate. 70(5):562-9 (2010).
Choi et al., "Circulating Extracellular Vesicles in Cancer Diagnosis and Monitoring," Mol Diagn Ther. 17(5):265-71 (2013).
Falconer et al., "Polysialyltransferase: A New Target in Metastatic Cancer," Curr Cancer Drug Targets. 12(8):925-39 (2012).
Höbarth et al., "Plasma Sialic Acid in Patients with Prostate Cancer," Br J Urol. 72(5 Pt 1 ):621-4 (1993).
Michalakis et al., "Detection of prostate cancer by sialic acid level in patients with non-diagnostic levels of prostate-specific antigen." Maturitas. 73(4):325-30 (2012).
Boutros et al., "Spatial genomic heterogeneity within localized, multifocal prostate cancer," Nat Genet. 47(7):736-45 (2015) (14 pages).
Fine et al., "A Contemporary Study Correlating Prostate Needle Biopsy and Radical Prostatectomy Gleason Score." J Urol. 179(4):1335-9 (2008).
International Preliminary Report on Patentability for International Application No. PCT/CA2018/050549, dated Nov. 12, 2019 (7 pages).

\* cited by examiner

FIG. 3B
Dual Positive EV Size
Group 2
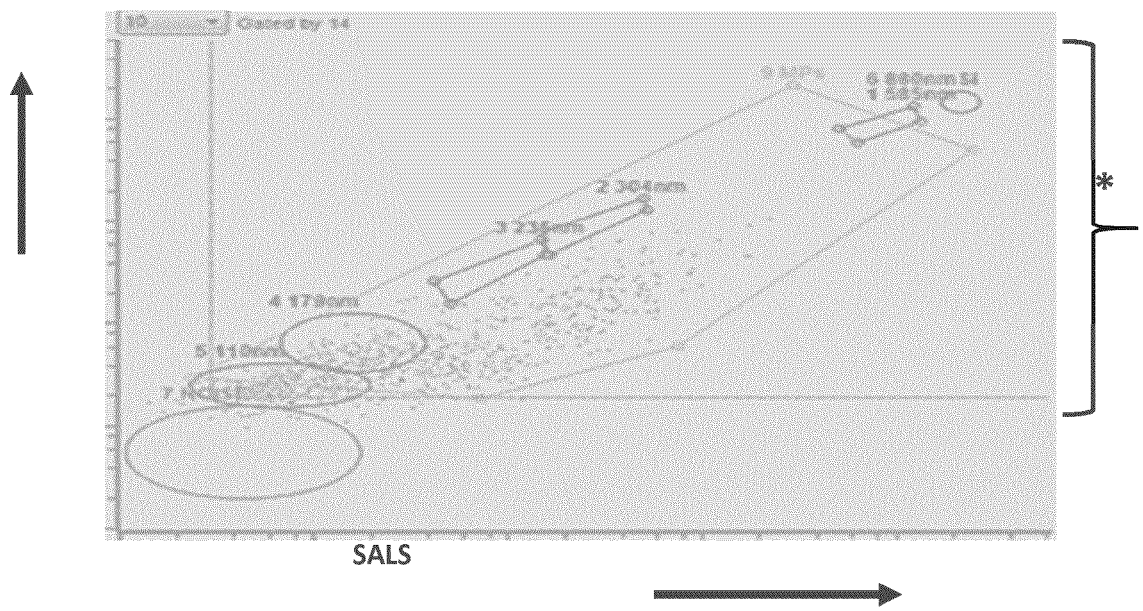
Group 4
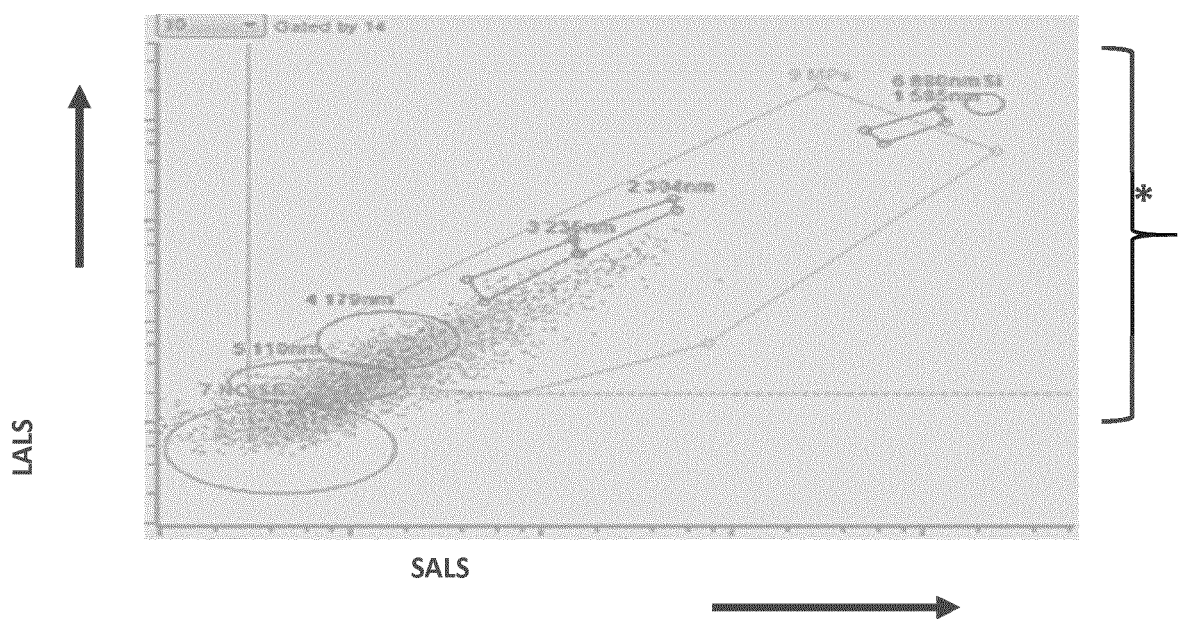

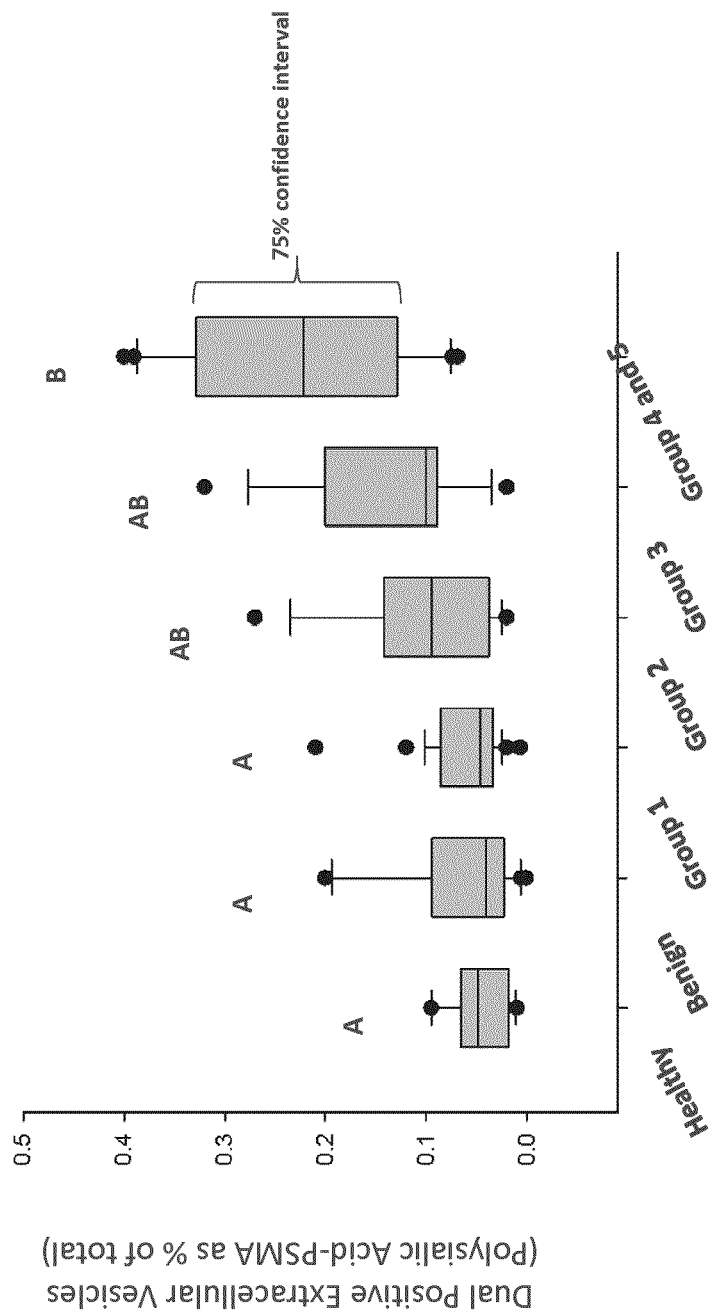

FIG. 7
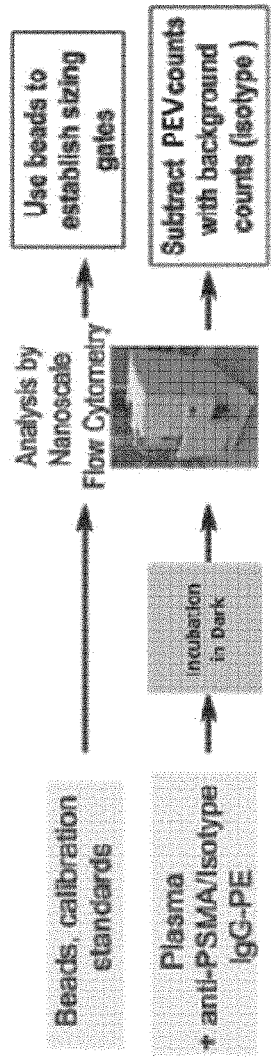
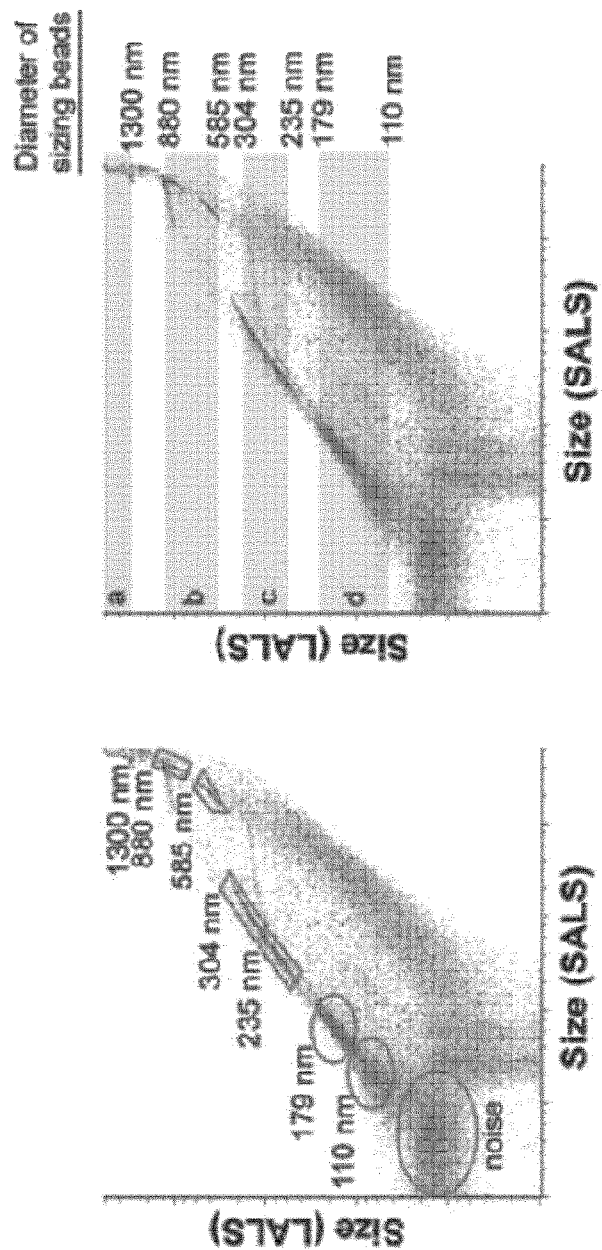

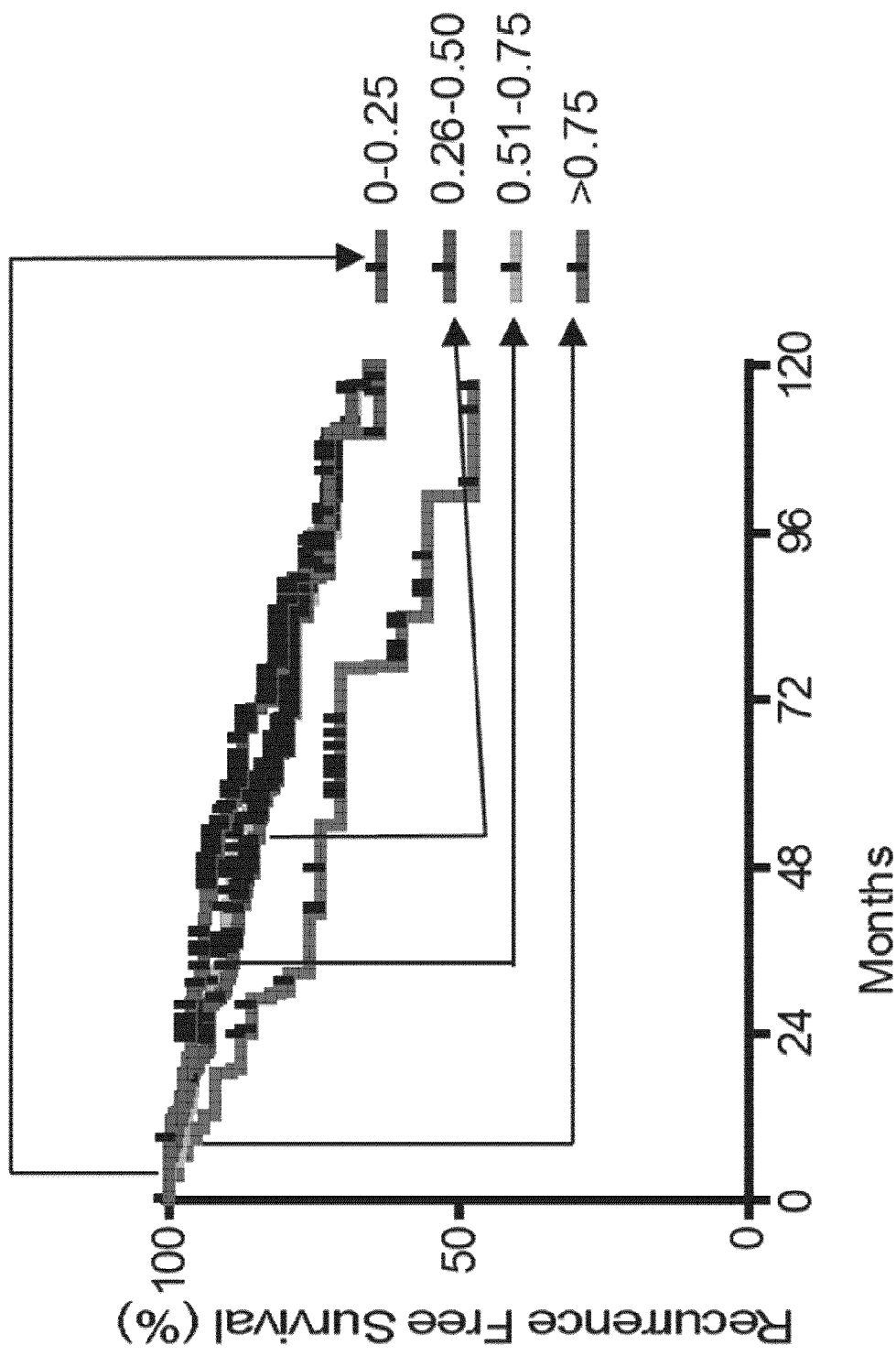

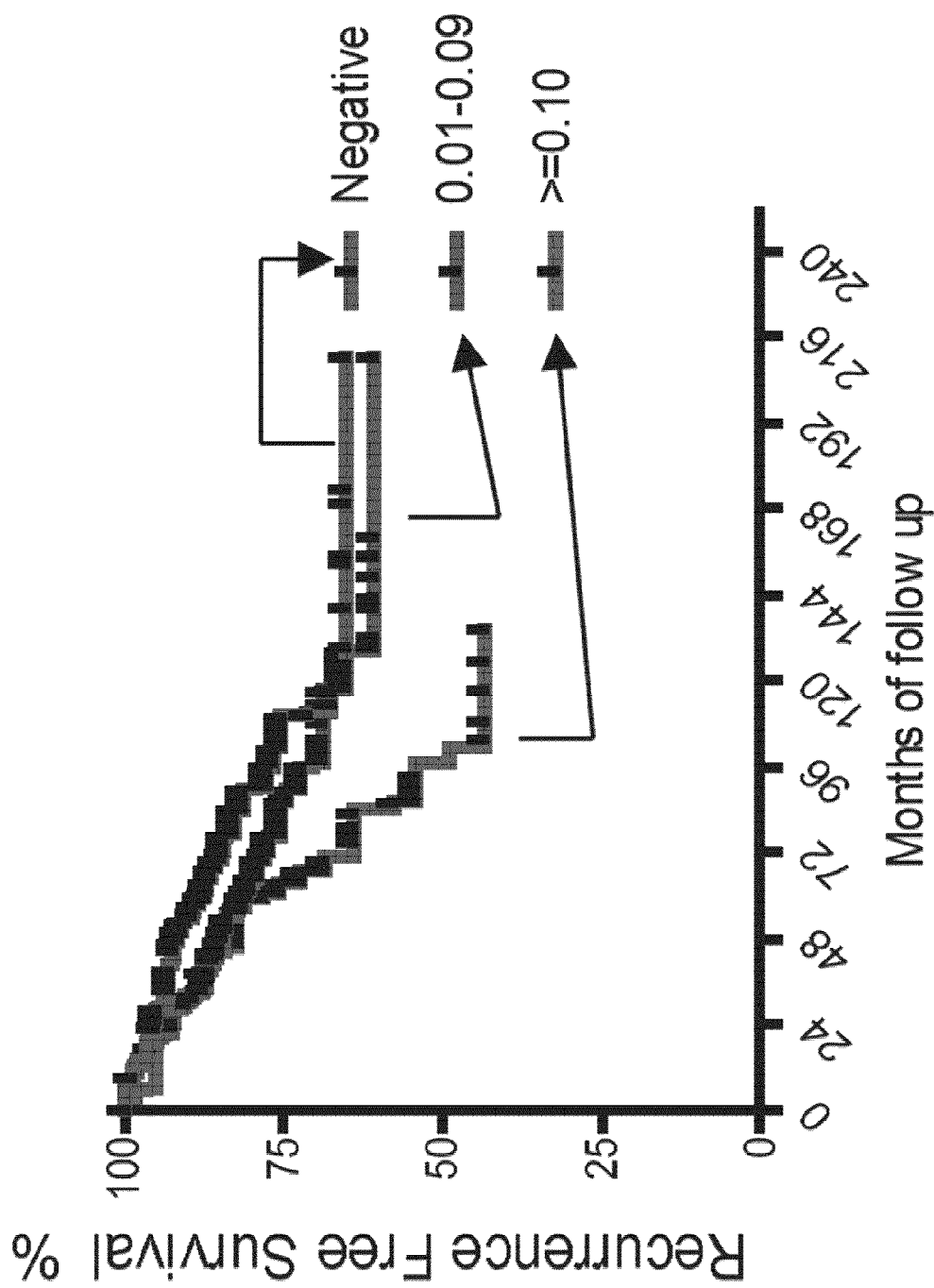

FIG. 14B

| | PSA ≥ 4 ng/ml | | Triple Positive Events ≥ 2000 | | Triple Positive Events ≥ 2000 +PSA≥18ng/ml | |
|---|---|---|---|---|---|---|
| | FDR | TDR | FDR | TDR | FDR | TDR |
| Low-Risk | 77.5% | - | 28% | - | 28% | - |
| High-Risk | 6.3% | 93.6% | 17.3% | 82.6% | 12.6% | 87.3% |

FIG. 16B

|  | PSA≥4ng/ml | | Triple Positive Events ≥ 2000 | | Triple Positive Events ≥ 2000 +PSA≥18ng/ml | |
| --- | --- | --- | --- | --- | --- | --- |
|  | FDR | TDR | FDR | TDR | FDR | TDR |
| Low-Risk | 69.5% | - | 13% | - | 15.5% | - |
| High-Risk | 13.3% | 86.6% | 28.3% | 71.6% | 19.9% | 80.1% |

METHODS FOR DIAGNOSING HIGH-RISK CANCER USING POLYSIALIC ACID AND ONE OR MORE TISSUE-SPECIFIC BIOMARKERS

FIELD OF THE INVENTION

The invention relates to methods for diagnosing high-risk or non-indolent cancer.

BACKGROUND

Cancer is a chronic disease in which certain mutated cells in the body proliferate without restraint, but cancer only becomes deadly when it acquires qualities that allow it to spread and colonize the rest of the body in a process known as metastasis. Cancer classified as indolent (e.g., slow growing) is considered low-risk cancer, while non-indolent cancer, such as high-risk cancer, is cancer that is likely to progress, increase in volume, recur, spread, and that is more likely to lead to mortality. Identifying whether cancer is low or high-risk is critically important in determining whether and how a subject with cancer is to be treated. Current methods for diagnosing high-risk cancer primarily depend on histological and genetic analysis of tissue biopsies. Diagnostic methods are needed to non-invasively risk stratify individual subjects with cancer as particularly high or low-risk prior to or at the onset of treatment.

Prostate cancer (PCa) is the second most common cancer in men worldwide and the most commonly diagnosed cancer. Unfortunately, it is also the most over-diagnosed and over-treated cancer. Prostate cancer (PCa) represents 24.1% of newly diagnosed cancers in men each year and is responsible for 10.0% of all cancer related deaths in men. This incidence rate is attributed in part to the ubiquitous use of the Prostate Specific Antigen (PSA) blood test as a screening tool and low decision threshold for needle-based biopsy of the prostate (tissue biopsy). The PSA blood test has a high incidence of false-positives (almost 20%) and is unable to distinguish between low-risk and high-risk patients. In up to 30% of cases, PSA is elevated for reasons other than PCa, leading to many unnecessary invasive prostate biopsies.

Prostate cancer can now be diagnosed much earlier, therefore, a higher percentage of newly diagnosed prostate cancer is low volume and early-staged, leading to decreased prostate cancer mortality. Patient demographics are also changing as an increasing number of younger men with different priorities are being diagnosed with early stage disease. An unanticipated consequence of this is a growing recognition that conventional, whole gland ablative therapies (e.g., surgery or radiation therapy), though very effective in eradicating the malignancy, may be excessive treatment. For many of these men, their cancer will not progress to a life-threatening phenotype and does not require aggressive treatment over their lifetime. Therefore, many genitourinary, gastrointestinal, and sexual side effects associated with radical prostatectomy or radiation therapy can be avoided for these low-risk patients.

There is accumulating prospective data suggesting that low-risk patients could benefit from "active surveillance" (AS), a management strategy whereby active therapy is withheld and close monitoring of the disease is undertaken. Only when there is evidence of PCa progression measured by PSA, digital rectal examination (DRE), or repeat prostate needle biopsy findings, do these patients undergo therapy at a time when cure is still achievable. The outcomes for low-risk patients under active surveillance is excellent: a metastasis-free survival rate of 97% and a 15 year cancer-specific survival rate of 94.3. Indeed, appropriate implementation of active surveillance has the potential to reduce the overtreatment of patients and spare ~40% of all diagnosed prostate cancer patients needless radical therapy, but many more patients could be placed on AS. Clinical parameters to assess patient candidacy for active surveillance include: PSA, DRE, and biopsy results to stratify patients as low, intermediate, and high-risk for subsequent disease progression, the development of metastases, and death. This categorization of patients is used to determine clinical management of patients, although there remains extreme heterogeneity in terms of tumor indolence or conversely, the progression of disease within each of these defined groups. There is a need for new methods to accurately determine the potential for disease progression at the time of diagnosis to direct patient treatment.

Breast cancer (BCa) is the most common cancer in women worldwide. Treatments for breast cancer include radiation, chemotherapy, and mastectomy, which are often given as early as possible to prevent cancer progression or death. Approximately 20-30 percent of BCa cases present as early Stage 0, Ductal Carcinoma in situ (DCIS), and Stage 1, Invasive Ductal Carcinoma (IDC) disease, because of screening mammography in healthy women. Even though many newly diagnosed early BCa patients are at low risk of clinical progression, the lack of reliable assays to distinguish between low-risk and high-risk patients results in substantial overtreatment of the disease with surgery, radiation and on occasion aromatase inhibitors or tamoxifen. Clinical studies over the last decade have sought to determine treatment benefit in the early BCa setting, with results highlighting overtreatment in ~90% of patients. For example, studies comparing the absolute benefit of radiotherapy after breast conserving surgery for DCIS show that the number of recurrent events prevented per 1000 treated women is typically less than 10% with an overall progression free benefit of 20-50%. Consequently, despite radiation being standard of care, clinical decisions to pursue aggressive treatment are often made on a patient by patient case, taking into consideration cardiovascular risk factors and modest increased risk of recurrence. What is needed is a robust assay to stratify early BCa patients at high-risk of invasive disease progression, directing aggressive treatments towards those individuals while sparing those with indolent disease. Recent studies have also indicated that early therapy in ductal carcinoma in situ (DCIS) is not always needed and may put patients at risk for adverse effects without sufficient potential for benefit. Many cases of DCIS are lesions that are diagnosed via screening that may never become malignant. Clinical trials involving active surveillance, in which subjects with DCIS undergo screening every six months (alternating mammograms and magnetic resonance imaging (MRI)) have been conducted, and suggest that active monitoring of breast cancer for signs of progression is a viable approach. Thus, there is a need for a non-invasive test to monitor breast cancer risk in subjects.

Identification of indolent disease from aggressive disease in both PCa and BCa is needed to direct patient treatment, ensuring that the right treatment is given to the right person at the right time. Intense efforts to identify markers, or combinations of markers, in blood or tissue have proceeded in light of our understanding that non-indolent cancers produce and release protein, nucleic acids, cells and extra-cellular vesicles unique to the disease state. The ability to detect these tumor-derived materials and define unique markers, and/or combinations of markers, specific to a disease state has the potential to transform clinical management in cancer. Discriminating high-risk individuals from low-risk will enable clinicians to deliver immediate, effective treatments, while sparing those with low-risk disease the toxic side effects of surgery, radiation and chemotherapy.

SUMMARY OF THE INVENTION

The invention features a method of diagnosing high-risk or non-indolent cancer in a subject, the method comprising: (i) measuring polysialic acid (polySia) in a biological sample obtained from the subject; (ii) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; and (iii) diagnosing the subject on the basis of the comparison to the two reference values. In particular embodiments, the method further comprises comparing the polySia measurement in the biological sample obtained from the subject to a third reference value obtained by measuring polySia in a biological sample from intermediate-risk cancer of the same tumor type as that of the subject. The biological samples can be liquid biopsies containing cancer extracellular vesicles, such as microvesicles. In particular embodiments, the liquid biopsies are blood, blood plasma, or semen samples.

In a related aspect, the invention features a method of assessing high-risk or non-indolent cancer in a subject, the method comprising: (i) providing a blood or semen sample from the subject; (ii) measuring the level of polysialic acid (polySia) in the blood or semen sample; and (iii) on the basis of the results of step (ii), assessing high-risk or non-indolent cancer in the subject. Assessing the subject can include diagnosing high-risk cancer in a subject, monitoring cancer in a subject, assessing cancer treatment efficacy in a subject, identifying a subject with cancer for a clinical trial, and/or predicting cancer recurrence in a subject.

In a related aspect, the invention features a method of monitoring cancer in a subject, the method comprising: (i) measuring polysialic acid (polySia) in a biological sample obtained from the subject; (ii) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; (iii) diagnosing the subject on the basis of the comparison to the two reference values; (iv) recommending a treatment based on the diagnosis; (v) measuring polysialic acid (polySia) in a biological sample obtained from the subject at a second time point; (vi) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; (vii) comparing the polySia measurement of the biological sample obtained from the subject to the subject's previous polySia measurement(s); and (viii) monitoring the subject on the basis of the comparison to the reference values and the subject's previous measurement(s).

In another related aspect, the invention features a method of assessing cancer treatment efficacy in a subject, the method comprising: (i) measuring polysialic acid (polySia) in a biological sample obtained from the subject, wherein the subject has been diagnosed and treated for cancer; (ii) comparing the polySia measurement of the biological sample obtained from the subject to two reference values, wherein the first reference value is obtained by measuring polySia in a pre-treatment biological sample, and wherein the second reference value is obtained by measuring polySia in a post-treatment biological sample; (iii) diagnosing the subject treatment response on the basis of the comparison to the two reference values; and (iv) assessing the efficacy of the therapy based on whether the diagnosis has improved compared to the diagnosis before treatment initiation.

In another related aspect, the invention features a method of assessing cancer treatment efficacy in a subject, the method comprising: (i) measuring polysialic acid (polySia) in a biological sample obtained from the subject, wherein the subject has been diagnosed and treated for cancer; (ii) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; (iii) diagnosing the subject on the basis of the comparison to the two reference values; and (iv) assessing the efficacy of the therapy based on whether the diagnosis has improved compared to the diagnosis before treatment initiation.

In a related aspect, the invention features a method of identifying a subject with cancer for a clinical trial, the method comprising: (i) measuring polysialic acid (polySia) in a biological sample obtained from the subject; (ii) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; and (iii) diagnosing the subject on the basis of the comparison to the two reference values. In particular embodiments, the method further comprises assigning the subject to an appropriate clinical trial based on cancer diagnosis.

In another related aspect, the invention features a method of predicting cancer recurrence in a subject, the method comprising: (i) measuring polysialic acid (polySia) in a biological sample obtained from the subject; (ii) comparing the polySia measurement of the biological sample obtained from the subject to two reference values, wherein the first reference value is obtained by measuring polySia in a biological sample from low-risk cancer of the same tumor type as that of the subject, and wherein the second reference value is obtained by measuring polySia in a biological sample from high-risk or non-indolent cancer of the same tumor type as that of the subject; and (iii) predicting the risk of cancer recurrence on the basis of the comparison to the two reference values. In particular embodiments, the method further comprises monitoring the subject to determine when the cancer has returned.

In particular embodiments of any of the above methods, the measurement is obtained using nanoscale flow cytometry. In some embodiments, the measurement is the number of extracellular vesicles, such as microvesicles, positive for polySia. The method can further include measuring one or more tissue-specific biomarkers in the biological samples per unit volume.

The cancer can be prostate cancer. The method can include measuring one or more tissue-specific biomarkers selected from the group consisting of prostate specific membrane antigen (PSMA) and six transmembrane epithelial antigen of the prostate 1 (STEAP1). In particular embodiments, the one or more tissue-specific biomarkers are PSMA and STEAP1.

The cancer can be breast cancer. The method can include further measuring one or more tissue-specific biomarkers including Mammaglobin A.

In some embodiments of any of the above methods, the biological samples are liquid biopsies containing cancer extracellular vesicles, such as microvesicles. In some embodiments of any of the above methods, the biological samples are blood, blood plasma, or semen samples.

In particular embodiments of any of the above methods, the biological samples are tissue biopsies. In some embodiments, the measurement is obtained using immunohistochemical staining. For example, the measurement can be the polySia staining intensity or staining pattern. In certain embodiments, the cancer is prostate cancer or breast cancer.

In particular embodiments of any of the above methods, the method further comprises treating a subject diagnosed with high-risk or non-indolent cancer with an aggressive therapy or treating a subject diagnosed with low-risk cancer with active surveillance or a therapy that has fewer side effects. In some embodiments, the aggressive therapy is selected from the group consisting of radical prostatectomy, external beam radiation, brachytherapy, hormone therapy, chemotherapy, cryotherapy, an anti-cancer vaccine, mastectomy, lymph node removal, or HER2-targeted therapy.

In particular embodiments of any of the above methods, the subject is a human.

The invention features a kit for diagnosing intermediate to high-risk cancer in a subject, wherein the kit comprises an antibody specific to polySia and one or more antibodies that are each specific to a tissue-specific biomarker. The kit can further include isotype control antibodies. The cancer can be prostate cancer. The kit can further include tissue-specific antibody biomarkers, such as PSMA and STEAP1. The cancer can be breast cancer. The kit can further include tissue-specific antibody biomarkers, such as Mammaglobin A.

In another aspect, the invention features a method of diagnosing prostate cancer in a subject, the method comprising: (i) measuring the number of prostate cancer extracellular vesicles in a biological sample obtained from the subject that are triple-positive for polySia, STEAP1, and PSMA; and (ii) diagnosing the subject with high-risk or non-indolent prostate cancer if the number of triple-positive extracellular vesicles per microliter of the biological sample is at least 2,000; or diagnosing the subject with low-risk prostate cancer if the number if triple-positive extracellular vesicles per microliter of the biological sample is less than 2,000. In some embodiments, the method further comprises performing a needle-core biopsy on the subject after diagnosis with high-risk or non-indolent prostate cancer. In some embodiments, the method further comprises treating a subject diagnosed with high-risk or non-indolent cancer with an aggressive therapy. In some embodiments, the method further comprises placing a subject diagnosed with low-risk cancer on active surveillance.

In another aspect, the invention features a method of identifying a subject with prostate cancer for a clinical trial, the method comprising: (i) measuring the number of prostate cancer extracellular vesicles in a biological sample obtained from the subject that are triple-positive for polySia, STEAP1, and PSMA; and (ii) selecting the subject for the clinical trial if the number of triple-positive extracellular vesicles per microliter of the biological sample is at least 2,000.

In another aspect, the invention features a method of treating prostate cancer in a subject (e.g., a subject having or at risk of developing prostate cancer), the method comprising: (i) measuring the number of prostate cancer extracellular vesicles in a biological sample obtained from the subject that are triple-positive for polySia, STEAP1, and PSMA; and (ii) treating the subject with an aggressive therapy if the number of triple-positive extracellular vesicles per microliter of the biological sample is at least 2,000; or placing the subject on active surveillance if the number of triple-positive extracellular vesicles per microliter of the biological sample is less than 2,000.

In yet another aspect, the invention features a method of treating prostate cancer in a subject, the method comprising: (i) providing a subject that has at least 2,000 prostate cancer extracellular vesicles that are triple-positive for polySia, STEAP1, and PSMA per microliter of a biological sample; and (ii) treating the subject with an aggressive therapy for prostate cancer.

In some embodiments of any of the above methods, the method further comprises performing a needle-core biopsy on the subject before aggressive treatment for prostate cancer.

In another aspect, the invention features a method of diagnosing prostate cancer in a subject, the method comprising: (i) providing a subject with a Prostate Specific Antigen (PSA) level of 2 ng/ml and <18 ng/ml (e.g., ≥4 ng/ml and <18 ng/ml, ≥4 ng/ml and ≤10 ng/ml, or ≥10 ng/ml and <18 ng/ml); (ii) measuring the number of prostate cancer extracellular vesicles in a biological sample obtained from the subject that are triple-positive for polySia, STEAP1, and PSMA; and (iii) diagnosing the subject with high-risk or non-indolent prostate cancer if the number of triple-positive extracellular vesicles per microliter of the biological sample is at least 2,000; or diagnosing the subject with low-risk prostate cancer if the number if triple-positive extracellular vesicles per microliter of the biological sample is less than 2,000. In some embodiments, the method further comprises performing a needle-core biopsy on the subject after diagnosis with high-risk or non-indolent prostate cancer.

In another aspect, the invention features a method of monitoring a subject for the development of prostate cancer (e.g., high risk or non-indolent prostate cancer), the method comprising: (i) providing a subject having less than 2,000 prostate cancer extracellular vesicles that are triple-positive for polySia, STEAP1, and PSMA per microliter of a biological sample; and (ii) measuring the number of triple-positive prostate cancer extracellular vesicles per microliter in a biological sample from the subject at least once a year. In some embodiments, the number of triple-positive prostate cancer extracellular vesicles are measured at least twice a year, at least three times a year, at least four times a year, at least six times a year, or at least twelve times a year. In some embodiments, monitoring is discontinued and the subject is treated with an aggressive therapy if the number of triple-positive prostate cancer extracellular vesicles per microliter measured in the biological sample is at least 2,000.

In another aspect, the invention features a method of assessing prostate cancer treatment efficacy in a subject, the method comprising: (i) providing a biological sample obtained from the subject prior to treatment and a biological sample obtained from the subject after treatment; (ii) measuring the number of prostate cancer extracellular vesicles in the biological samples obtained from the subject that are triple-positive for polySia, STEAP1, and PSMA; and (iii) determining that the treatment has been effective if the number of triple-positive extracellular vesicles per microliter in the biological sample obtained after treatment is lower than the number of triple-positive extracellular vesicles per microliter in the biological sample obtained before treatment; or determining that the treatment has not been effective if the number of triple-positive extracellular vesicles per microliter in the biological sample obtained after treatment is equal to or greater than the number of triple-positive extracellular vesicles per microliter in the biological sample obtained before treatment.

In another aspect, the invention features a method of assessing treatment efficacy in a subject treated for prostate cancer (e.g., high-risk or non-indolent prostate cancer), the method comprising: (i) measuring the number of prostate cancer extracellular vesicles in a biological sample obtained from the subject that are triple-positive for polySia, STEAP1, and PSMA; and (ii) determining that the treatment has been effective if the number of triple-positive extracellular vesicles per microliter in the biological sample is less than 2,000; or determining that the treatment has not been effective if the number of triple-positive extracellular vesicles per microliter in the biological sample is 2,000 or more.

In another aspect, the invention features a method of treating cancer in a subject (e.g., a subject having or at risk of developing cancer), the method comprising: (i) measuring the number of cancer extracellular vesicles in a biological sample obtained from the subject that are positive for polySia and one or more tissue-specific biomarkers; and (ii) treating the subject with an aggressive therapy if the number of extracellular vesicles positive for polySia and one or more tissue-specific biomarkers per microliter of the biological sample is at least 2,000; or placing the subject on active surveillance if the number of extracellular vesicles positive for polySia and one or more tissue-specific biomarkers per microliter of the biological sample is less than 2,000.

In yet another aspect, the invention features a method of treating cancer in a subject, the method comprising: (i) providing a subject that has at least 2,000 cancer extracellular vesicles that are positive for polySia and one or more tissue-specific biomarkers per microliter of a biological sample; and (ii) treating the subject with an aggressive therapy for cancer.

In another aspect, the invention features a method of detecting cancer extracellular vesicles in a subject, the method comprising quantifying the number of extracellular vesicles per microliter of a biological sample obtained from the subject that are about 50 nm to about 1400 nm in size and positive for polySia and one or more tissue-specific biomarkers.

In some embodiments of any of the above methods, the cancer is prostate cancer. In some embodiments of any of the above methods, the tissue-specific biomarkers are PSMA and STEAP1. In some embodiments of any of the above methods, the method further comprises administering an aggressive therapy to a subject having at least 2,000 extracellular vesicles per microliter of the biological sample that are triple-positive for polySia, PSMA, and STEAP1. In some embodiments of any of the above methods, the aggressive therapy is radical prostatectomy, external beam radiation, brachytherapy, hormone therapy, chemotherapy, cryotherapy, and an anti-cancer vaccine.

In some embodiments of any of the above methods, the cancer is breast cancer. In some embodiments of any of the above methods, the tissue-specific biomarker is Mammaglobin A. In some embodiments of any of the above methods, the method further comprises administering an aggressive therapy to a subject having at least 2,000 extracellular vesicles per microliter of the biological sample that are dual-positive for polySia and Mammaglobin-A. In some embodiments of any of the above methods, the aggressive therapy is selected from the group consisting of mastectomy, external beam radiation, brachytherapy, lymph node removal, chemotherapy, hormone therapy, HER2-targeted therapy, or cryotherapy.

In another aspect, the invention features a method of assessing the risk of metastatic prostate cancer recurrence in a subject, the method comprising: (i) measuring the number of prostate cancer extracellular vesicles in a biological sample obtained from the subject that are triple-positive for polySia, STEAP1, and PSMA; and (ii) diagnosing the subject with high-risk of metastatic prostate cancer recurrence if the number of triple-positive extracellular vesicles per microliter of the biological sample is greater than 4,000. In some embodiments, the method further comprises treating the subject with metastatic inhibitors.

In another aspect, the invention features a method of treating prostate cancer in a subject, the method comprising: (i) providing a subject that has greater than 4,000 prostate cancer extracellular vesicles that are triple-positive for polySia, STEAP1, and PSMA per microliter of a biological sample; and (ii) treating the subject with a metastatic inhibitor.

In another aspect, the invention features a method of assessing the risk of metastatic cancer recurrence in a subject, the method comprising: (i) measuring the number of cancer extracellular vesicles in a biological sample obtained from the subject that are positive for polySia and one or more tissue-specific biomarkers; and (ii) diagnosing the subject with high-risk of metastatic cancer recurrence if the number of extracellular vesicles positive for polySia and one or more tissue-specific biomarkers per microliter of the biological sample is greater than 4,000. In some embodiments, the method further comprises treating the subject with a metastatic inhibitor.

In another aspect, the invention features a method of treating cancer in a subject, the method comprising: (i) providing a subject that has greater than 4,000 cancer extracellular vesicles that are positive for polySia and one or more tissue-specific biomarkers per microliter of a biological sample; and (ii) treating the subject with a metastatic inhibitor.

In some embodiments of any of the above methods, the cancer is prostate cancer. In some embodiments of any of the above methods, the tissue-specific biomarkers are PSMA and STEAP1.

In some embodiments of any of the above methods, the cancer is breast cancer. In some embodiments of any of the above methods, the tissue-specific biomarker is Mammaglobin A. In some embodiments of any of the above methods, the method further comprises treating the subject with a single or double mastectomy.

In some embodiments of any of the above methods, the method further comprises measuring the number of triple-positive extracellular vesicles in a biological sample obtained from the subject after treatment. In some embodiments, a decrease in the number of triple-positive extracellular vesicles in the biological sample after treatment compared to the number of triple-positive extracellular vesicles in the biological sample before treatment indicates treatment efficacy. In some embodiments, the subject is treated with an additional round of therapy or a different therapy if the number of triple-positive extracellular vesicles in a biological sample obtained from the subject after treatment is equal to or greater than the number of triple-positive extracellular vesicles in the biological sample before treatment.

In another aspect, the invention features a method of diagnosing breast cancer in a subject, the method comprising: (i) measuring the number of breast cancer extracellular vesicles in a biological sample obtained from the subject that are dual-positive for polySia and Mammaglobin-A; and (ii) diagnosing the subject with high-risk or non-indolent breast cancer if the number of dual-positive extracellular vesicles per microliter of the biological sample is at least 2,000; or diagnosing the subject with low-risk breast cancer if the number if dual-positive extracellular vesicles per microliter of the biological sample is less than 2,000.

In another aspect, the invention features a method of identifying a subject with breast cancer (e.g., high-risk or non-indolent breast cancer) for a clinical trial, the method comprising: (i) measuring the number of breast cancer extracellular vesicles in a biological sample obtained from the subject that are dual-positive for polySia and Mammaglobin-A; and (ii) selecting the subject for the clinical trial if the number of dual-positive extracellular vesicles per microliter of the biological sample is at least 2,000.

In another aspect, the invention features a method of treating breast cancer in a subject (e.g., a subject having or at risk of developing breast cancer), the method comprising: (i) measuring the number of breast cancer extracellular vesicles in a biological sample obtained from the subject that are dual-positive for polySia and Mammaglobin-A; and (ii) treating the subject with an aggressive therapy if the number of dual-positive extracellular vesicles per microliter of the biological sample is at least 2,000; or placing the subject on active surveillance if the number of dual-positive extracellular vesicles per microliter of the biological sample is less than 2,000.

In another aspect, the invention features a method of treating breast cancer in a subject, the method comprising: (ii) providing a subject that has at least 2,000 breast cancer extracellular vesicles that are dual-positive for polySia and Mammaglobin-A per microliter of a biological sample; and (iii) treating the subject with an aggressive therapy for breast cancer.

In another aspect, the invention features a method of monitoring a subject for the development of breast cancer (e.g., high-risk or non-indolent breast cancer), the method comprising: (i) providing a subject having less than 2,000 breast cancer extracellular vesicles that are dual-positive for polySia and Mammaglobin-A per microliter of a biological sample; and (ii) measuring the number of dual-positive breast cancer extracellular vesicles per microliter in a biological sample from the subject at least once a year. In some embodiments, the number of dual-positive breast cancer extracellular vesicles are measured at least twice a year, at least three times a year, at least four times a year, at least six times a year, or at least twelve times a year. In some embodiments, monitoring is discontinued and the subject is treated with an aggressive therapy if the number of dual-positive breast cancer extracellular vesicles per microliter measured in the biological sample is at least 2,000.

In another aspect, the invention features a method of assessing breast cancer treatment efficacy in a subject, the method comprising: (i) providing a biological sample obtained from the subject prior to treatment and a biological sample obtained from the subject after treatment; (ii) measuring the number of breast cancer extracellular vesicles in the biological samples obtained from the subject that are dual-positive for polySia and Mammaglobin-A; and (iii) determining that the treatment has been effective if the number of dual-positive extracellular vesicles per microliter in the biological sample obtained after treatment is lower than the number of dual-positive extracellular vesicles per microliter in the biological sample obtained before treatment; or determining that the treatment has not been effective if the number of dual-positive extracellular vesicles per microliter in the biological sample obtained after treatment is equal to or greater than the number of dual-positive extracellular vesicles per microliter in the biological sample obtained before treatment.

In another aspect, the invention features a method of assessing treatment efficacy in a subject treated for high-risk or non-indolent breast cancer, the method comprising: (i) measuring the number of breast cancer extracellular vesicles in a biological sample obtained from the subject that are dual-positive for polySia and Mammaglobin-A; and (ii) determining that the treatment has been effective if the number of dual-positive extracellular vesicles per microliter in the biological sample is less than 2,000; or determining that the treatment has not been effective if the number of dual-positive extracellular vesicles per microliter in the biological sample is 2,000 or more.

In another aspect, the invention features a method of assessing the risk of metastatic breast cancer recurrence in a subject, the method comprising: (i) measuring the number of breast cancer extracellular vesicles in a biological sample obtained from the subject that are dual-positive for polySia and Mammaglobin-A; and (ii) diagnosing the subject with high-risk of metastatic breast cancer recurrence if the number of dual-positive extracellular vesicles per microliter of the biological sample is greater than 4,000. In some embodiments, the method further comprises treating the subject with a metastatic inhibitor or a single or double mastectomy.

In another aspect, the invention features a method of treating breast cancer in a subject, the method comprising: (i) providing a subject that has greater than 4,000 breast cancer extracellular vesicles that are dual-positive for polySia and Mammaglobin-A per microliter of a biological sample; and (ii) treating the subject with a metastatic inhibitor or a single or double mastectomy.

In some embodiments of any of the above methods, the method further comprises measuring the number of dual-positive extracellular vesicles in a biological sample obtained from the subject after treatment. In some embodiments, a decrease in the number of dual-positive extracellular vesicles in the biological sample after treatment compared to the number of dual-positive extracellular vesicles in the biological sample before treatment indicates treatment efficacy. In some embodiments, the subject is treated with an additional round of therapy or a different therapy if the number of dual-positive extracellular vesicles in a biological sample obtained from the subject after treatment is equal to or greater than the number of dual-positive extracellular vesicles in the biological sample before treatment.

In some embodiments of any of the above methods, the biological sample is blood, blood plasma, or semen.

In some embodiments of any of the above methods, the measurement of cancer extracellular vesicles (e.g., prostate cancer extracellular vesicles or breast cancer extracellular vesicles) is obtained using nanoscale flow cytometry.

In some embodiments of any of the above methods, the method further comprises treating a subject diagnosed with high-risk or non-indolent cancer with an aggressive therapy. In some embodiments of any of the foregoing aspects, the method further comprises placing a subject diagnosed with low-risk cancer on active surveillance.

In some embodiments of any of the above methods, the aggressive therapy for prostate cancer is selected from the group consisting of radical prostatectomy, external beam radiation, brachytherapy, hormone therapy, chemotherapy, cryotherapy, and an anti-cancer vaccine. In some embodiments of any of the above methods, the aggressive therapy for breast cancer is selected from the group consisting of mastectomy, external beam radiation, brachytherapy, lymph node removal, chemotherapy, hormone therapy, HER2-targeted therapy, or cryotherapy.

In some embodiments of any of the above methods, the subject is at risk of developing cancer (e.g., is at risk of developing cancer due to family history of cancer, genetic mutations that increase the risk of developing cancer, exposure to carcinogens or known environmental risk factors, other medical conditions (e.g., obesity, hormonal imbalance, chronic inflammation) or medications taken for other medical conditions (e.g., hormone therapy), advanced age, alcohol abuse, diet, immunosuppression, or infection).

In some embodiments of any of the above methods, the subject is a human.

In another aspect, the invention features a kit for diagnosing high-risk or non-indolent prostate cancer in a subject, wherein the kit contains a solution including antibodies specific for polySia, STEAP1, and PSMA.

In yet another aspect, the invention provides a kit for diagnosing high-risk or non-indolent breast cancer in a subject, wherein the kit contains a solution including antibodies specific for polySia and Mammaglobin-A.

In some embodiments of any of the above kits, each of the antibodies is conjugated to a different fluorophore. In some embodiments of any of the above kits, the kit further includes isotype control antibodies. In some embodiments of any of the above kits, the kit further includes calibration beads. In some embodiments of any of the above kits, the kit further includes instructions directing a user of the kit to perform nanoscale flow cytometry to diagnose high-risk or non-indolent prostate or breast cancer.

Definitions

As used herein, the terms "aggressive treatment" or "aggressive therapy" refer to cancer treatments with significant side effects (e.g., surgery, radiation therapy, and chemotherapy, among others). Aggressive therapy approaches are typically used for high-risk or non-indolent cancer that has a high likelihood of progressing, increasing in volume, metastasizing, or leading to mortality. The methods described herein are designed to ensure that aggressive treatments are appropriately used to treat high-risk patients or patients with non-indolent cancer and not given to patients with low-risk cancer who could benefit from monitoring or less aggressive treatments with fewer side effects.

As used herein, the terms "benign prostatic hyperplasia" and "BPH" refer to an increase in size of a prostate due to an increase in the number of prostate cells. BPH is not known to cause cancer, including prostate cancer, or to increase the risk of cancer, including prostate cancer.

As used herein, the terms "biomarker" and "marker" refer to a protein, polypeptide, or post-translational modification that is differentially present in samples from different tissues, or in samples from subjects with a disease or condition as compared to subjects without the disease. A biomarker may be a molecule whose measurement provides information regarding the state of a subject, or a feature of a subject, for example, the disease state of a subject can be assessed using a biomarker. Measurements of a biomarker may be used alone or combined with other data obtained regarding a subject, or feature thereof, in order to determine the stat of the subject, or feature thereof. The terms "tissue-specific biomarker" and "tissue-specific marker" as used herein, refer to proteins or polypeptides expressed by one tissue type that are expressed only minimally or not at all by other tissue types. For example, prostate specific membrane antigen (PSMA) and six transmembrane epithelial antigen of the prostate 1 (STEAP1) are prostate-specific biomarkers, and Mammaglobin A is a breast-specific biomarker. As used herein, the terms "cancer-specific biomarker" and "cancer biomarker" refer to proteins, polypeptides, or post-translational modifications found in cancer cells but not in healthy cells. Cancer biomarkers may also vary between different types of cancers (e.g., low-risk cancer and high-risk cancer). In the present invention, we have discovered that PolySialic Acid is an excellent biomarker for high-risk or non-indolent cancer, as the concentration of polySia positive extracellular vesicles, such as microparticles or microvesicles in the blood of cancer patients correlates with Gleason score and cancer recurrence (e.g., higher concentrations of polySia-positive extracellular vesicles are observed in the blood, plasma, or tissue of patients with Gleason group ≥3, and in the blood, plasma, or tissue of patients whose cancer has recurred).

As used herein, the term "biopsy" refers to a biological sample obtained from a subject. A biopsy may be used for analysis (e.g., diagnosis) to determine the presence or status of disease (e.g., type of disease, severity of disease, or cause of disease). A biopsy may be used to direct disease treatment or provide a prognosis. As used herein, the term "liquid biopsy" refers to a fluid sample obtained from a subject (e.g., a blood, plasma, serum, urine, breast milk, sweat, semen, or saliva sample). As described herein, a liquid biopsy obtained from a subject with cancer (e.g., prostate cancer or breast cancer) may contain cancer extracellular vesicles, such as microvesicles. The term "tissue biopsy" as used herein refers to a tissue sample obtained from a subject (e.g., prostate tissue or breast tissue).

As used herein, the terms "breast cancer extracellular vesicle," and "BCEV" refer to an extracellular vesicle, such as a microvesicles, between 50 nm-1400 nm (e.g., 100 nm-1400 nm) in size that expresses one or more breast tissue-specific biomarkers (e.g., Mammaglobin A). BCEVs are fragments of breast cancer cells, and they may also express cancer-specific biomarkers, which can differ depending on whether the cancer is indolent or aggressive, as will be appreciated by one of skill in the art. BCEVs from high-risk or non-indolent breast cancer may express polySia. As used herein, the terms "breast cancer microparticle" and "breast cancer microvesicle" are synonymous and refer to types of BCEVs.

As used herein, the terms "cancer extracellular vesicle," and "CEV" refer to fragments of tumor cells released at the cell membrane during necrosis, cell activation, or apoptosis.

CEVs belong to a class of biological entities called "extracellular vesicles" which include microparticles, microvesicles, apoptotic bodies, oncosomes, exosomes, and ectosomes. CEVs exhibit a size range between 50 nm-1400 nm (e.g., 100 nm-1400 nm) and can continue to express membrane based biomarkers or antigens, reflecting their origin of release at the cell membrane. CEVs are present in the blood (e.g., blood plasma) and other body fluids (e.g., semen). Using monoclonal antibodies specific to the extracellular portion of cell-specific and cancer-specific antigens, CEVs can be readily detected in cancer patient liquid biopsies (e.g., blood, serum, plasma, semen). As used herein, the terms "cancer microparticle" and "cancer microvesicle" are synonymous and refer to types of CEVs.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, muscle tissue, breast tissue, or prostate tissue) and/or those that are isolated from a common organ, tissue system, blood vessel, or other structure and/or region in an organism.

As used herein, the terms "detect", "detection" and "detecting" refer to a quantitative or qualitative determination of a property of an entity, for example, quantifying the amount or concentration of a molecule (e.g., a biomarker) or the activity level of a molecule. The term "concentration" or "level" can refer to an absolute or relative quantity. Measuring a molecule (e.g., a biomarker) may also include determining the absence or presence of the molecule. Various methods of detection are known in the art, for example fluorescence analysis. In this regard, biomarkers can be measured using fluorescence detection methods or other methods known to the skilled artisan.

As used herein, the terms "diagnose," "diagnosis," and "diagnosing" refer to determining the nature or the identity of a condition or disease. A diagnosis may provide information regarding the severity of the disease. Diagnosis as it relates to the methods described herein, relates to determining whether cancer is low-risk or high-risk.

As used herein, the term "disease state" refers to any distinguishable manifestation of a particular disease, including non-disease. For example, disease state includes the presence or absence of a disease, the risk of developing a disease, the stage of a disease, the progression or remission of a disease over time and the severity of disease. The term "worsened disease state" refers to the progression of a disease over time. The term "improved disease state" refers to remission of disease over time.

As used herein, the term "efficacy" refers to the capacity of an intervention to produce a therapeutic effect. For example, a prostate cancer treatment having good efficacy might significantly reduce or eliminate from a subject detectable tumor-forming prostate epithelial cells. In contrast, a prostate cancer treatment having a poor efficacy might not reduce in a subject the level of detectable tumor-forming prostate epithelial cells.

As used herein, the terms "extracellular vesicle" and "EV" refer to membrane surrounded structures released by cells, which include microparticles, microvesicles, apoptotic bodies, oncosomes, exosomes, and ectosomes. EVs exhibit a size range between 50 nm-1400 nm. The cargo contained within and on surface of the EV is representative of the cell of origin containing lipids, proteins, metabolites, glycans and nucleic acids. EVs are rapidly shed from tumor cells either directly from the plasma membrane (microvesicles) or through exocytosis (exosomes) and are readily detectable in the blood ($\sim$1-3$\times$10$^{12}$ exosomes per ml of plasma). Due to their documented abundance and stability in the blood the use of EVs in disease detection and monitoring is most promising. Through the profiling of EVs valuable information has been obtained with the potential to direct patient treatment. For example, in lung cancer the mutation status of EGFR can be detected through isolation of EVs.

As used herein, the terms "Gleason group score" and "GGS" refer to a histological grading scale used to determine prostate cancer risk by assessing morphological parameters of tumor cells in histological sections of a needle biopsy or whole mount prostate specimen. It consists of two numbers (1-5, differentiated to least differentiated state) that describe the two main lesions most abundant in the prostate biopsy/section. There is consistent and longstanding evidence that GGS is a powerful prognosticator for survival, failure, and/or progression for patients with histologically proven prostate cancer. For example, patients who have a Gleason group score 1 (Gleason score $\leq$6, commonly 3+3 Gleason pattern; Gleason patterns of 4+2 are rare) at initial diagnosis are unlikely to progress and die from their cancer within 10-15 years (>98% 5 year survival rate), and patients who have a GGS 2 (Gleason score 3+4=7) at initial diagnosis are also unlikely to progress (>92% 5 year survival). Whereas, patients with a GGS$\geq$3 (Gleason Group 3=Gleason score 4+3=7, Gleason Group 4=Gleason score 8, Gleason Group 5=Gleason scores 9 and 10) have a higher chance of progressing to advanced disease (<76% 5 year survival).

As used herein, the term "high-risk cancer" refers to cancer that has an increased likelihood of a negative outcome (e.g., progression, increase in tumor volume, metastasis, recurrence, reversal of remission, or mortality) within a short period of time (e.g., within 6 months, within 1 year, within 2 years, within 3 years, within 4 years, within 5 years). High-risk cancer may also refer to cancer that is likely to recur after intent-to-cure or apparently curative therapy (e.g., surgery, radiation therapy, chemotherapy). A diagnosis of high-risk cancer may indicate that radical therapy (e.g., surgery, radiation therapy, chemotherapy) is necessary for treatment. High-risk prostate cancer includes patients with Gleason Group 4 and 5 prostate cancer as well as patients having Gleason Group 2 (Gleason Score 3+4) and Gleason Group 3 (Gleason Score 4+3) prostate cancer.

As used herein, the term "low-risk cancer" refers to cancer that has a low likelihood of a negative outcome. Low-risk cancer is cancer that is unlikely to progress, spread, or increase in tumor volume, and subjects with low-risk cancer will have a longer time to recurrence post-treatment and greater longevity (e.g., 5 years or more, e.g., 5, 10, 15, or 20 years or more before cancer recurs or causes mortality). Subjects with low-risk cancer do not require aggressive treatment and can undergo monitoring (e.g., active surveillance) with repeated testing over time to determine whether there is any change in disease state.

As used herein, the terms "monitor" and "monitoring" refer to observation of a disease over time. Monitoring of a subject's disease state can be performed by continuously measuring certain parameters and/or performing a medical test repeatedly. A subject's disease state can be monitored by obtaining bodily fluid samples repeatedly, assaying the samples using the methods disclosed herein and comparing assay results with one another and with reference values to identify any change in the subject's disease state.

As used herein, the terms "polysialic acid" and "polySia" refer to a carbohydrate glycan moiety that is a post-translational modification of specific receptors, such as neuronal cell adhesion molecule (NCAM). PolySia is a linear polymer of up to 400 sialic α2,8-linked N-acetylneuraminic acid (NeuAc) residues. Its large size and negative charge reduce interactions with adjacent membranes and impart a migratory phenotype. In healthy adults, polySia expression appears to be limited to the nervous and immune systems, where it is crucial for neurite outgrowth, axon formation, synaptogenesis, and migration of activated dendritic NK and T cells. PolySia can be detected in the methods described herein using polySia-specific antibodies and measured using nanoscale flow cytometry, immunohistochemistry, and confocal microscopy.

As used herein, the terms "prognostic" and "prognosis" refer to predicting the probable course or outcome of a disease (e.g., cancer). The prognosis can include the presence, outcome, or aggressiveness of the disease (e.g., likelihood that cancer will progress, increase in volume, recur, metastasize, or lead to mortality).

As used herein, the terms "prostate cancer extracellular vesicle," and "PCEV" refer to an extracellular vesicle (e.g., a microvesicle or microparticle) between 50 nm-1400 nm (e.g., 100 nm-1400 nm) in size that expresses prostate tissue-specific markers (e.g., prostate specific membrane antigen (PSMA) and six transmembrane epithelial antigen of the prostate 1 (STEAP1)). PCEVs may express one or more (e.g., 1, 2 or more) prostate tissue-specific markers. PCEVs are extracellular vesicles that are fragments of prostate cancer cells, and they may also express cancer-specific biomarkers, which can differ depending on whether the cancer is indolent or aggressive, as will be appreciated by one of skill in the art. As described herein, triple positive PCEVs (PSMA+ve STEAP+ve polySia+ve) are abundant in high-risk and non-indolent prostate patient plasma samples. As used herein, the terms "prostate cancer microparticle" and "prostate cancer microvesicle" are synonymous and refer to types of PCEVs.

As used herein, the term "sample" refers to a specimen (e.g., blood, blood component (e.g., serum or plasma), urine, saliva, sweat, semen, amniotic fluid, cerebrospinal fluid, tissue (e.g., prostate or breast), and cells) isolated from a subject.

As used herein, the terms "subject" or "patient" refer to an animal (e.g., a mammal, such as a human). A subject to be diagnosed or treated according to the methods described herein may be one who has been previously treated for cancer, previously monitored for cancer, previously diagnosed with cancer, or at risk of developing cancer. Initial diagnosis may be performed according to the methods described herein or by any method or technique known in the art. One skilled in the art will understand that a subject to be diagnosed or treated according to the present disclosure may have been subjected to standard tests or may have been identified, without examination, as one at risk due to the presence of one or more risk factors associated with the disease or condition.

As used herein, "treatment" and "treating" in reference to a disease or condition, refer to an approach for obtaining beneficial or desired results, e.g., clinical results. Beneficial or desired results can include, but are not limited to, alleviation or amelioration of one or more symptoms or conditions; diminishment of extent of disease or condition; stabilized (i.e., not worsening) state of disease, disorder, or condition; preventing spread of disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

BRIEF DESCRIPTION OF THE DRAWINGS

FIGS. 3A and 3B are a series of graphs depicting PSMA and polysialic acid levels in prostate cancer extracellular vesicles. Bivariate plots from patient plasma samples represented. Patient plasmas were incubated with antibodies specific to prostate-specific membrane antigen (PSMA) conjugated to phycoerythrin and antibodies specific for polySia conjugated to FITC for 30 min at room temperature protected from light. Plasma was diluted 1:30 with dH2O and analyzed by nanoscale flow cytometry. Left column represents the total extracellular vesicle population (exosomes+ microvesicles) present in 20 μL of patient plasma. Noise is outlined in bottom-most circle representing particles less than 100 nm, which is below the detectable limit of the cytometer. Extracellular vesicles (outlined rectangular area in graphs on left) were gated based on sizing standards (liposomes of known sizes) and output to the right column. The outlined area in the right column was manually selected to exclude background noise and non-specific signal as determined by IgG controls and represents extracellular vesicles positive for both PSMA and polysialic acid (FIG. 3A). Bivariate plots representing only the dual-positive population from Gleason Group 2 and Gleason Group 4 in (A) to show the size of the dual-positive population, ranging from about 100-400 nm. *Dual Positive events are between 100-1400 nm in diameter. A fraction of dual positive events can be seen in the outlined noise area, possibly representing exosomes which are characterized as been being smaller than microvesicles (30-100 nm) (FIG. 3B). LALS and SALS refer to large and small angle light scattering respectively, which in combination indicate the size of analyzed events.

FIGS. 4A and 4B are a series of graphs depicting PSMA and polysialic acid levels in prostate cancer extracellular vesicles. One hundred fifteen patient plasmas were analyzed by nanoscale flow cytometry and dual-positive extracellular vesicle levels were graphed as a percentage of total plasma extracellular vesicles. The upper graph represents individual patients grouped by Gleason Group score (GGS). Benign refers to benign prostatic hyperplasia, Gleason Group 1 is 3+3, Gleason Group 2 is 3+4, Gleason Group 3 is 4+3, and 4+4, 4+5, 5+4 are Gleason Group 4/5. The cutoff was arbitrarily chosen so that the false-positive rate in healthy patients was less than 15% (FIG. 4A). Statistical analysis of the data in panel A was performed using Sigma Plot. There were significantly more dual-positive events for Gleason Group 4/5 compared to healthy or benign plasmas (p<0.05). Although there was a trend of increased dual-positive events in Gleason Groups 2 and 3, it was not found to be significantly different from any other category, possibly due to low sample size. Different letters represent statistically significant differences (FIG. 4B).

FIG. 7 are a flow chart and schematic demonstrating that nanoscale flow cytometry can be used to detect extracellular vesicles, such as microvesicles. Preparation of samples for analysis by nanoscale flow cytometry requires calibration of the instrument with beads of known sizes/diameters. Using silica based calibration beads of known sizes (110, 179, 235, 304, 585, 880, 1300 nm), analysis reveals distinct subpopulations when plotted on LALS vs. SALS (long angle light scatter, short angle light scatter). Analysis of samples for detection of biomarkers requires staining the sample separately with isotype controls of the actual antibodies of interest and analysis on the nanoscale flow cytometer prior to analysis of the experimentally stained plasma sample. The isotype control sample will indicate the number of non-specific binding extracellular vesicles present in the sample and this value is subtracted from the experimentally stained sample.

FIGS. 8A-8G are a series of graphs depicting STEAP1-positive extracellular vesicles and demonstrating that they are present at detectable levels in healthy and PCa plasmas, as determined by nanoscale flow cytometry. STEAP1 extracellular vesicles were detected using nanoscale flow cytometry (FIG. 8A). Bivariate plots from patient plasma samples are represented. Patient plasmas were incubated with six-transmembrane epithelial antigen of the prostate (STEAP1) conjugated to Alexa647 and analyzed on a nanoscale flow cytometer. The outlined area was manually selected to exclude background noise and non-specific signal as determined by IgG controls and represents extracellular vesicles positive for STEAP1. LALS=large angle light scatter. Quantification of STEAP1-extracellular vesicle levels in plasma samples as determined by nanoscale flow cytometry (FIG. 8B). Significantly higher levels were found in Group 3 and 5 compared to benign (p=0.018) and Group 5 (p=0.0034) and Group 5 compared to Group 1 (p=0.0318). Three hundred seventy eight plasma samples consisting of 27 healthy, 128 benign, 53 Group 1, 51 Group 2, 83 Group 3, 9 Group 4, and 27 Group 5 plasma were analyzed and the distribution is represented. STEAP1 extracellular vesicle levels were grouped and analyzed based on patient risk-stratification (FIG. 8C). Significantly higher levels were found in high-risk compared to healthy (p=0.0004) and benign/low risk (p=0.0069). Histochemical staining for STEAP1 was performed using benign and prostate cancer tissue cores (FIG. 8D). Representative images are shown. Analysis of 750 tissue cores for STEAP1 expression in prostate cancer by Group score (FIG. 8E) and risk level (FIG. 8F). Significantly higher expression was found in high-risk compared to benign and low-risk (p<0.05). Kaplan-Meier curves were generated to display time to recurrence for patients based on STEAP1 tissue expression levels (FIG. 8G). Different letters represent statistical significance (p<0.05). Data is shown as mean±standard deviation.

FIGS. 9A-9H are a series of graphs demonstrating that PSMA positive extracellular vesicles are present in all plasma samples, while dual-positive PSMA-STEAP1 extracellular vesicle levels are elevated in prostate cancer. PSMA extracellular vesicles, left column, and dual-positive PSMA-STEAP1 extracellular vesicles, right column, were detected using nanoscale flow cytometry (FIG. 9A). Bivariate plots from patient plasma samples are represented. The outlined area was manually selected to exclude background noise and non-specific signal as determined by IgG controls and represents extracellular vesicles positive for PSMA, left column, and PSMA-STEAP1, right column. PSMA-extracellular vesicle levels (FIG. 9B) and PSMA-STEAP1 extracellular vesicle levels (FIG. 9C) were analyzed in plasma samples using nanoscale flow cytometry. Three hundred seventy eight plasma samples consisting of 27 healthy, 128 benign, 53 Group 1, 51 Group 2, 83 Group 3, 9 Group 4, and 27 Group 5 plasma were analyzed and the distribution is represented. Significantly higher levels were found in Group 3 and 5 compared to healthy, benign, Group 1, and Group 2 ($p<0.02$). STEAP1-PSMA extracellular vesicle levels were analyzed based on patient risk-stratification (FIG. 9D). Significantly higher levels were found in high-risk compared to healthy and benign/low risk ($p<0.0001$). Histochemical staining for PSMA was performed in benign and prostate cancer tissue cores (FIG. 9E). Representative images are shown. Analysis of 750 tissue cores for PSMA expression in prostate cancer by Group score (FIG. 9F) and risk level (FIG. 9G). Significantly higher expression was found in high-risk compared to benign and low-risk ($p<0.05$). Kaplan-Meier curves were generated to display time to recurrence for patients based on PSMA tissue expression levels (FIG. 9H). Different numbers represent statistical significance ($p<0.05$). Data is shown as mean±standard deviation.

FIGS. 14A and 14B are a graph and table demonstrating that a triple-positive extracellular vesicle test outperforms PSA testing. A triple-positive extracellular vesicle test was evaluated to predict high-risk prostate cancer in relation to PSA testing using the area under receiver operating characteristic curve (AUC, FIG. 14A). The middle curve represents the performance characteristics for a triple positive extracellular vesicle test, the lower curve represents the performance characteristics of PSA testing (>4 ng/ml), and the upper-most curve represents a combination of triple positive extracellular vesicles (>2000 events/µl) and PSA (18 ng/ml) to report non-indolent disease. The diagonal line represents the reference line, AUC=0.5. False-positive discovery rate (FDR) and true-positive discovery rates (TDR) are represented for each method diagnosing prostate cancer (FIG. 14B).

FIGS. 16A and 16B are a graph and table demonstrating that a validated triple-positive extracellular vesicle test outperforms PSA testing. Evaluation of a triple-positive extracellular vesicle test was performed to predict high-risk prostate cancer in relation to PSA testing using the area under receiver operating characteristic curve (AUC, FIG. 16A). The middle curve represents the performance characteristics for a triple positive extracellular vesicle test, the lower curve represents the performance characteristics of PSA testing (>4 ng/ml), and the upper-most curve represents a combination of triple positive extracellular vesicles (>2000 events/µl) and PSA (18 ng/ml) to report non-indolent disease. The diagonal line represents the reference line, AUC=0.5. False-positive discovery rate (FDR) and true-positive discovery rates (TDR) are represented for each method diagnosing prostate cancer (FIG. 16B).

DETAILED DESCRIPTION

Figure 1:
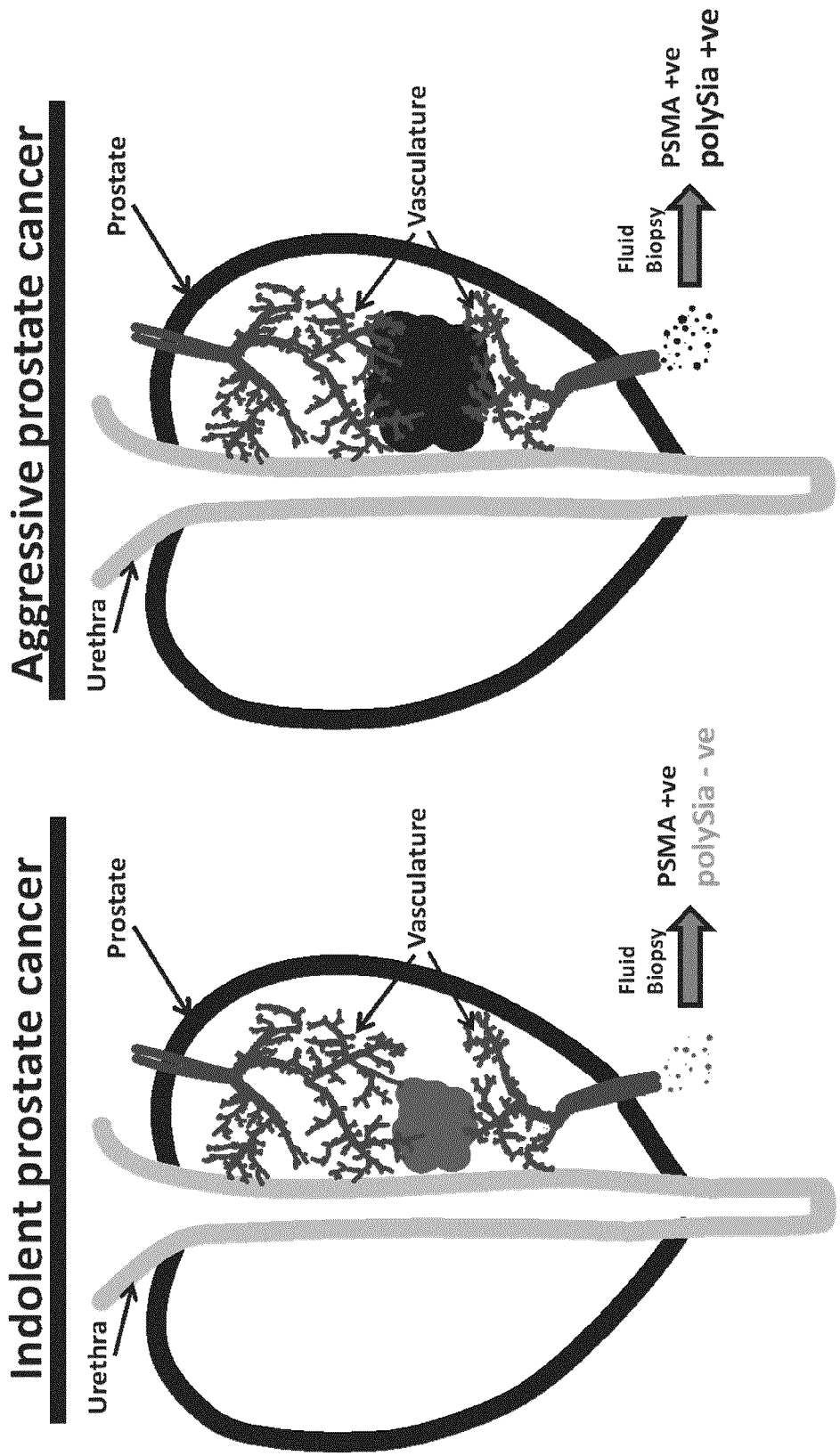
FIG. 1 is a schematic depicting use of polysialic acid (polySia), and one or more tissue-specific markers, as a biomarker for detecting high-risk prostate cancer. Extracellular vesicles in fluid samples from patients with indolent cancer will be positive for tissue-specific markers (e.g., prostate specific marker PSMA) and negative for cancer biomarker polySia (left). Extracellular vesicles from patients with high-risk, aggressive prostate cancer will be positive for tissue-specific markers, such as PSMA and STEAP1, and polySia.

Described herein are methods for diagnosing or identifying high-risk or non-indolent cancer in a subject (such as a mammalian subject, for instance, a human) by detecting polysialic acid (polySia) in a biological sample obtained from the subject. For instance, described herein are methods of diagnosing high-risk or non-indolent cancer (e.g., prostate cancer or breast cancer) by detecting polySia and one or more tissue-specific biomarkers on cancer extracellular vesicles, such as microvesicles, in a liquid biopsy (e.g., blood sample or semen sample) obtained from the subject. PolySia may also be used to diagnose high-risk or non-indolent cancer in tissue-biopsies from a subject through immunohistochemical staining. The methods described herein provide approaches to rapidly and non-invasively identify subjects with high-risk or non-indolent cancer and histologically identify subjects at risk of developing early cancer recurrence.

Cancer

Cancer is a chronic disease in which certain mutated cells in the body proliferate without restraint, but only becomes deadly when it acquires qualities that allow it to spread and colonize the rest of the body in a process known as metastasis. Cancer classified as indolent (e.g., slow growing) is considered low-risk cancer, while high-risk or non-indolent cancer is cancer that is likely to progress, increase in volume, recur, spread, or lead to mortality. Identifying whether cancer is low or high-risk is critically important in determining whether and how a subject with cancer is to be treated.

The ability to non-invasively diagnose and predict the biology of prostate cancer (PCa) or breast cancer for each patient is the most important step towards vastly improving the outcome for patients that may or may not require therapy for life-threatening disease and to refrain from treating patients with biologically insignificant cancer; ergo, low-risk cancer. For those with high-risk disease at diagnosis (i.e., Gleason Group 3-5), early intervention is required such as prostatectomy. For many low-risk PCa patients, (Prostate Specific Antigen<10 ng/mL, Gleason Group 1 and 2, and low volume on biopsy), active surveillance is a viable option with repeat biopsies every 6-12 months the only source of patient apprehension. This is because repeat biopsies submit patients to complications such as hematuria (66%), rectal bleeding (9%) and urinary tract infection (0.5%) with rare cases leading to mortality. Although biopsy of the prostate yields important histopathological data that is needed to guide patient management to determine if the cancer is low-grade (Gleason score Group 1 and 2) or high grade (Gleason Group 3-5), prostate needle biopsy yield and efficacy is not ideal, with as many as 1 in 5 prostate needle biopsies producing incorrect diagnoses that lead to either unnecessary prostatectomies or a lack of treatment for patients with high-risk PCa.

The methods described herein provide significant advantages over current diagnostic methods. First, subjects diagnosed using the methods described herein can be stratified as having low or high-risk (e.g., high-risk or non-indolent) cancer. The ability to risk stratify patients prior to or at the onset of treatment can reduce both overtreatment and unnecessary biopsies. This would reduce treatment costs and improve quality of life for patients, as biopsies are painful and invasive, and aggressive treatment (e.g., surgery or radiation therapy) can cause serious side effects, for example, the genitourinary, gastrointestinal, and sexual side effects that are experienced by prostate cancer patients receiving aggressive treatment. Second, the ability to use the methods described herein to diagnose patients based on extracellular vesicles, such as microvesicles, in liquid biopsies (e.g., blood samples or semen samples) means that testing for cancer can be non-invasive. As the methods described herein have been validated using liquid biopsies from patients with known diagnoses and histories, they can be used as an alternative to more invasive diagnostic methods. As these methods are not only non-invasive, but also relatively low cost compared to current methods, they can be used to routinely screen patients for cancer, even non-symptomatic patients, which would improve detection of cancers that typically evade detection until they are at a fairly advanced stage. Third, the methods described herein may produce more accurate results than existing diagnostic methods. A blood-based assay that detects tissue-specific tumor extracellular vesicles, such as microvesicles, overcomes the inherent variability associated with individual body chemistry and may be more representative of tumor heterogeneity than a single tumor biopsy. The ability to detect tumor-derived extracellular vesicles, such as microvesicles, from specific tissues also reduces off-target detection from other organs. Finally, the methods described herein also have prognostic value, as high levels of the cancer biomarker described herein are correlated with cancer recurrence.

The methods described herein can be used to identify or diagnose high-risk cancer (e.g., high-risk cancer or non-indolent cancer). The cancer may be classified as a high-risk or non-indolent cancer due to increased likelihood of a negative outcome (e.g., progression, increase in tumor volume, metastasis, reversal of remission, recurrence, or mortality). The types of cancer that can be diagnosed using the methods described herein include prostate cancer (e.g., adenocarcinoma, acinar adenocarcinoma, ductal adenocarcinoma, transitional cell (or urothelial) cancer, squamous cell cancer, small cell prostate cancer, sarcoma, small cell carcinoma, neuroendocrine tumors, and transitional cell carcinoma) and breast cancer (e.g., ductal carcinoma in situ, invasive ductal carcinoma, invasive lobular carcinoma, adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma, micropapillary carcinoma, mixed carcinoma, inflammatory breast cancer, lobular carcinoma in situ, male breast cancer, Luminal A breast cancer, Luminal B breast cancer, triple-negative/basal-like breast cancer, triple-positive breast cancer, HER2-positive breast cancer, HER2-negative breast cancer, estrogen receptor-positive breast cancer, estrogen receptor-negative breast cancer, progesterone receptor-positive breast cancer, progesterone receptor-negative breast cancer, normal-like breast cancer, Paget's disease of the nipple, Phyllodes tumors of the breast, angiosarcoma, and recurrent and metastatic breast cancer). The methods described herein may be used during active surveillance, and may be used to diagnose a naïve subject or a subject who has been previously treated for cancer (e.g., prostate or breast cancer), previously monitored for cancer (e.g., prostate or breast cancer), previously diagnosed with cancer (e.g., prostate or breast cancer), or is at risk of developing cancer (e.g., family history of prostate or breast cancer, exposure to carcinogens or known environmental risk factors, or due to advanced age).

Cancer Biomarkers

A biomarker that may be used as a cancer-specific biomarker in the methods described herein is polysialic acid (polySia). PolySia is a linear polymer of up to 400 sialic α2,8-linked N-acetylneuraminic acid (NeuAc) residues. Depending on developmental state, only a small fraction of cells have glycoproteins carrying polySia. The presence of polySia has profound consequences for the physiology of the cell; its large size and negative charge generate a large excluded volume which has been shown to reduce interactions with adjacent membranes and impart a migratory phenotype. In healthy adults, polySia expression appears to be limited to the nervous and immune systems, where it is crucial for neurite outgrowth, axon formation, synaptogenesis, and migration of activated dendritic NK and T cells. The most highly characterized expression of polySia is the elaboration of N-linked glycans of the neural cell adhesion molecule (NCAM or CD56), particularly in neurons. However, it has been found on SynCAM, CD36, and recently as part of mucin-type O-linked glycans on neuropilin-2.

The methods described herein can be used to diagnose or identify subjects with high-risk or non-indolent cancer based on polySia detection. Our data demonstrate that aggressive PCa cell lines contain polySia, and that polySia is present on PCa-derived extracellular vesicles, such as microvesicles (e.g., 0.05-1.4 µm extracellular vesicles, e.g., 0.1-1 µm extracellular vesicles released from PCa cells) obtained from in vivo models. Importantly, patient plasmas show a strong positive correlation between polySia-containing, PCa-derived extracellular vesicles, such as microvesicles and higher Gleason scores/Gleason group scores, indicating that a "liquid biopsy" (e.g., blood test) can be used to report the histology of a primary tumor and that polySia may be specific to high-risk or non-indolent cancer versus indolent cancer. This correlation is critical, as it indicates that polySia detection in liquid biopsies can be used in place of more invasive diagnostic methods, such as tissue biopsies. This correlation can be observed due to the use of tissue-specific biomarkers and nanoscale flow cytometry to detect extracellular vesicles, such as microvesicles, a technical advance that prevents polySia on other cells in the bloodstream (e.g., immune cells and other non-tumor cells) from interfering with diagnostic measurements. PolySia can be detected using polySia-specific lectins or polySia-specific antibodies, which can be combined with tissue- or cell-type-specific antibodies to identify or diagnose cancers of specific tissue types (e.g., prostate or breast).

PolySia can also be used as a prognostic marker for cancer (e.g., prostate or breast cancer) that will recur in the patient even after treatment (e.g., surgery, radiation therapy, or chemotherapy), as our data showed a positive correlation between increased polySia levels in tissue biopsies and increased polySia extracellular vesicles in plasma from patients with recurrent cancer. The methods described herein can be used to predict risk of cancer recurrence based on immunohistochemical staining of prostate tissue biopsies and whole mount resected prostates (e.g., tissue from needle-based biopsies and prostatectomies) with polySia specific antibodies, or based on measuring polySia-positive extracellular vesicles, such as microvesicles, in liquid biopsies. Subjects predicted to have a high risk of cancer recurrence based on measurements of polySia staining or polySia-positive extracellular vesicles can then be screened more frequently for the development of cancer using the methods described herein or other screening methods (e.g., PSA screening, DRE, mammogram, ultrasound, magnetic resonance imaging, or tissue biopsy), and can be treated using more aggressive therapies (e.g., using metastasis inhibitors or single or double mastectomy). The methods described herein can also be used to perform risk stratification of subjects prior to cancer treatment. Subjects that may be diagnosed using the methods described herein include subjects not previously screened for cancer, subjects undergoing active surveillance, and subjects previously treated for cancer (e.g., subjects who received intent-to-cure treatment, including surgical treatment, radiation therapy, or chemotherapy). The diagnostic methods described herein can also be combined with traditional diagnostic methods for prostate cancer (e.g., DRE, prostate specific antigen (PSA) blood test, or tissue biopsy) and breast cancer (e.g., mammogram, ultrasound, MRI, or tissue biopsy). A diagnosis of high-risk or non-indolent cancer based on the methods described herein can be used to direct patient treatment. For example, a determination that a subject has high-risk cancer using the methods described herein can lead to immediate, aggressive treatment (e.g., radical prostatectomy or mastectomy). A subject diagnosed with high-risk or non-indolent cancer using the methods described herein may undergo additional diagnostic testing and/or cancer treatment (e.g., surgery, radiation therapy, or chemotherapy).

Extracellular Vesicles

The methods described herein use extracellular vesicles as one means of diagnosis. Extracellular vesicles comprise a family of subcellular entities that includes microparticles/microvesicles, ectosomes, oncosomes, and exosomes. Cancer extracellular vesicles (CEVs) are essentially fragments of tumor cells released at the cell membrane during necrosis, cell activation, or apoptosis and their levels in patient serum/plasma can be correlated to tumor burden. In some cases, CEVs can continue to express membrane based biomarkers or antigens, reflecting their origin of release at the cell membrane. CEVs are present in the blood, semen, and other body fluids. Using monoclonal antibodies specific to the extracellular portion of cell-specific and cancer-specific antigens, CEVs can be readily detected in cancer patient serum/plasma.

Extracellular vesicles for use in the methods described herein include prostate cancer extracellular vesicles (PCEVs) and breast cancer extracellular vesicles (BCEVs). PCEVs can be detected using nanoscale flow cytometry as events exhibiting a size range between 50 nm-1400 nm (e.g., 100 nm-1400 nm), that simultaneously express tissue-specific markers (e.g., prostate specific membrane antigen (PSMA) and six transmembrane epithelial antigen of the prostate 1 (STEAP1)). Size range of extracellular vesicles is determined based on nanoscale flow cytometry parameters. PCEVs may be detected using one or more (e.g., 1, 2, 3, or more) prostate-specific biomarkers. Triple positive PCEVs (PSMA+ve STEAP1+ve polySia+ve) are abundant in high-risk PCa patient plasma samples. BCEVs can be detected using nanoscale flow cytometry as events exhibiting a size range between 50 nm-1400 nm (e.g., 100 nm-1400 nm) that simultaneously express breast specific antigens (e.g., Mammaglobin A). Double positive BCEVs (Mammaglobin A+ve polySia+ve) may be indicative of high-risk or non-indolent breast cancer. Nanoscale flow cytometry can be used to enumerate CEVs in patient liquid biopsy samples in a multi-parametric and high throughput manner. Simultaneous detection of the co-expression of a tissue-specific marker(s) and a cancer specific marker on the surface of extracellular vesicles is not possible by conventional methods such as ELISA, immunoblots, or dynamic light scattering technology since they do not allow for the vesicle size and presence of biomarker(s) to be simultaneously correlated. Nanoscale flow cytometry can be performed with the Apogee A50-Micro instrument (Apogee FlowSystems Inc.) or with the Beckman Coulter Cytoflex instrument (Beckman Coulter Inc.), both of which enable 6 channel based flow cytometric analysis of events between 50 nm-1400 nm (e.g., 100 nm-1400 nm) in diameter. Using an additional cancer-specific biomarker (e.g., polySia), patients with benign prostatic hyperplasia (BPH) can be distinguished from patients with high-risk prostate cancer with ~85% accuracy. This is an improvement over assays based on evaluation of STEAP1 and/or PSMA positive extracellular vesicles, as STEAP1 and PSMA positive extracellular vesicles are also elevated in subjects with BPH.

Extracellular vesicles, such as microvesicles, may be detected using a "liquid biopsy" (e.g., blood or semen sample) to enumerate the number of CEVs present in patient blood (e.g., blood plasma) or semen samples that simultaneously express tissue specific biomarkers (e.g., PSMA and STEAP1 for prostate cancer; Mammaglobin A for breast cancer) and a cancer biomarker (e.g., polysialic acid). Extracellular vesicles for use in the methods of the present invention can be obtained from any bodily fluid (e.g., blood, serum, plasma, urine, breast milk, colostrum, saliva, tears, synovial fluid, cerebrospinal fluid, lymph, tears, aqueous humor, vitreous humor, mucus, semen, vaginal lubrication, interstitial fluid, endolymph, peritoneal fluid, perspiration, feces, perilymph, or pericardial fluid). A blood-based assay that detects extracellular vesicles released by the tumor overcomes the inherent variability associated with individual body chemistry and may be more representative of tumor heterogeneity than a single tumor biopsy. A liquid biopsy is also a less invasive means for detailed patient monitoring than traditional tissue biopsies used for cancer diagnosis. The ability to detect tumor-derived extracellular vesicles from specific tissues also reduces off-target detection from other organs. The liquid biopsy described herein will have an accuracy of 68% or greater (e.g., 68%, 70%, 75%, 80%, 85%, 90%, 95%, 97%, 98%, 99%, or more) in identifying patients whose cancer evolves to a high-risk or non-indolent phenotype whilst on active surveillance, thus requiring intent-to-cure therapy (e.g., surgery, radiation therapy, chemotherapy). Liquid biopsies provide an opportunity to reduce overtreatment and unnecessary biopsies.

Current Diagnostic Approaches

The methods described herein may be combined with or compared to current approaches used to diagnose cancer. Many of the current approaches used to diagnose cancer rely on tissue biopsies. Prostate cancer biopsies are performed by obtaining 11-13 needle cores from the prostate with the aid of ultrasound or MRI imaging to guide tissue collection. Tissue samples may also be obtained after prostatectomy. After successful biopsy, the tumor is evaluated using the Gleason score (GS) system, a histological grading scale that determines prostate cancer risk by assessing morphological parameters of tumor cells in histological sections of a needle biopsy or whole mount prostate specimen. It consists of two numbers (1-5, differentiated to least differentiated state) that describe the two main lesions most abundant in the prostate biopsy/section. Prostate cancer is typically Gleason Group 1 and can also include Gleason Group 2 and higher (e.g., Gleason Group scores 3-5, which represent a more invasive disease), although inclusion of Gleason Group 1 as part of the 'cancer' definition may soon change.

There is consistent and longstanding evidence that GS is a powerful prognosticator for survival, failure, and/or progression for patients with histologically proven prostate cancer. For example, patients who have a Gleason Group Score 1 (commonly Gleason score (GS) 3+3; Gleason patterns of 4+2 are rare) at initial diagnosis are unlikely to progress and die from their cancer within 10-15 years (>95% 5 year survival rate), whereas patients with a GS ≥7 (GS 3+4, Gleason Group 2; 4+3, Gleason Group 3; GS4+4, Gleason Group 4; or 5+4/4+5 is Gleason Group 5) have a higher chance of progressing to advanced disease, with Gleason score 4+3 the higher between the two. As a result, low-risk prostate cancer patients on active surveillance tend to maintain their low-risk status, but a minority of patients (~15-20%) will have tumors that will progress by exhibiting an increase in Gleason score/Gleason Group Score (i.e., from GS 3+3 (Gleason Group 1) to GS 3+4 (Gleason Group 2)) which is also known as "upgrading," and are finally recommended radical therapy. However, GS upgrading is purely dependent on needle biopsy accuracy (80% accuracy rate), which submits 3% of patients to complications such as urosepsis, acute urinary retention and gross hematuria during their time on active surveillance. There is a need for a non-invasive method to determine GS upgrading in the prostate, especially since biopsy can sometimes "miss" tumor when performed or provide an inconsistent sample. As PCEVs are correlated with higher Gleason scores, liquid biopsies may be used to complement or replace traditional tissue biopsies.

Breast cancer can also be diagnosed based on tissue biopsy, and genetic tests are available to distinguish indolent and aggressive cancers in specific cases. Clinically validated markers used in breast cancer biopsies (ER, PR, and HER2) have well-established predictive value capable of directing therapy, but cannot identify individuals at high-risk of recurrence. In breast cancer that is node negative, estrogen receptor positive, and characterized as early stage, Oncotype Dx genetic analysis (Genomic Health Inc.) can distinguish between indolent and aggressive cancers in tissue biopsy samples, however, its use is limited to early stage, hormone receptor-positive disease. Breast cancer may also be diagnosed by mammogram, ultrasound, or magnetic resonance imaging (MRI), although these methods are primarily performed prior to biopsy and not used to determine whether cancer is indolent or aggressive.

The methods described herein can be used as a diagnostic approach before more invasive testing (e.g., liquid biopsy prior to prostate or breast tissue biopsy) or they may follow another diagnostic approach (e.g., liquid or tissue biopsy to detect polySia after mammogram, ultrasound, MRI, tissue biopsy, PSA blood test, DRE, or genetic testing) to provide additional information or clarify unclear results. Immunohistochemical staining for polySia may be performed using tissue biopsies collected for other diagnostic approaches (e.g., tissue biopsies collected for Gleason scoring, genetic analysis, or biomarker analysis), and polySia staining may be performed before, concurrently, or after the other diagnostic approaches are performed. Staining may also be performed on resected tumors (e.g., tissue biopsies, prostatectomies) removed during therapy (e.g., surgery) to provide prognostic information about the risk of cancer recurrence. The methods described herein may also be used in place of other diagnostic approaches (e.g., liquid biopsy instead of tissue biopsy for prostate cancer or breast cancer, or polySia immunohistochemical analysis instead of Gleason scoring or genetic testing). When other diagnostic approaches are used before, after, or concurrently with the methods described herein to diagnose high-risk or non-indolent cancer, the results of multiple approaches (e.g., 2, 3, 4, or more approaches) may be considered as a whole to make a diagnosis. If the liquid biopsy indicates high-risk or non-indolent cancer based on the methods described herein but Gleason score does not, this may indicate that the tumor was not sampled adequately during the tissue biopsy.

Information obtained using the methods described herein may be used to direct patient treatment. If polySia is not detected in liquid or tissue biopsies, one of skill in the art may conclude that the subject does not have high-risk cancer, and does not require radical therapy (e.g., surgery, radiation therapy, chemotherapy). For example, a subject having low levels of triple-positive PCEVs (e.g., polySia-PSMA-STEAP1 positive extracellular vesicles, e.g., less than 2,000 triple-positive events/µl) would not receive a radical prostatectomy or a needle biopsy. Similarly, a subject having low levels of dual-positive BCEVs (e.g., polySia-Mammaglobin A positive extracellular vesicles, e.g., less than 2,000 dual-positive events/µl) would not receive a mastectomy. Subjects not diagnosed with high-risk or non-indolent cancer when tested using the methods described herein can undergo monitoring (e.g. active surveillance) and be tested again using the methods described herein 6 months later (e.g., 6 months, 1 year, 2 years, 3 years or more after the previous liquid biopsy). Subjects not diagnosed with high-risk or non-indolent cancer when tested using the methods described herein can also undergo other diagnostic tests (e.g., tissue biopsy followed by Gleason scoring, diagnostic imaging (e.g., a mammogram), genetic testing, or biomarker analysis) at about the same time (e.g., the same day, the same week, the same month) or during later monitoring (e.g., 6 months, 1 year, 2 years, or 3 years later). If a subject is diagnosed with high-risk or non-indolent cancer using the methods described herein, additional diagnostic testing may be performed to confirm results or further characterize the cancer prior to treatment (e.g., Gleason scoring, genetic testing, or biomarker analysis). A subject diagnosed with high-risk or non-indolent cancer using the methods described herein may also be tested to determine whether the cancer has metastasized using existing approaches (e.g., blood test, bone scan, X-ray, CT scan, PET scan). If the methods described herein indicate that a subject has high-risk cancer, one of skill in the art may recommend that the subject undergo radical therapy (e.g., surgery, radiation therapy, or chemotherapy).

Assays

In some embodiments, blood can be collected using a standard EDTA blood collection tube to extract any volume of blood greater than 1 ml. Standard hospital blood collection methods are sufficient to perform the methods described herein, and may include EDTA-blood tube collection followed by centrifugation for 10 minutes at 1,000-2,000×g using a refrigerated centrifuge or centrifugation for 15 minutes at 2,000×g. Centrifugation can occur at any time post blood sample collection (e.g., immediately, 15 minutes, 30 minutes, 45 minutes, 1 hr, 2 hrs, 3 hrs, or 4 hrs after collection, or longer if stored at −80° C.). Blood plasma is the yellow fraction above the cell pellet, gently removed and stored at −80° C. for long term storage. Short-term storage may occur at 4° C. for short time intervals of 5 min to 4 hours.

To detect extracellular vesicles, plasma is incubated with antibodies specific for tissue markers and polysialic acid, with another aliquot stained with isotype antibodies as immunostaining controls. The amount of plasma incubated can be 5 µl to 100 µl (e.g., 5 µl, 10 µl, 20 µl, 30 µl, 40 µl, 50 µl, 60 µl, 70 µl, 80 µl, 90 µl, or 100 µl). The concentration of antibody used for detection can be 1 µl of 0.2 µg/ml. Commercially available antibodies that bind to the extracellular domain of the tissue specific markers and polySia can be used in the methods described herein. These antibodies include the J2D2 clone, AA 106-155 (ABIN610692), and/or Middle-region (ABIN1031108) for STEAP1; J591, and/or 3E7 for PSMA; 3C8 for Mammaglobin-A; and Ab735 for polySia. Antibodies and plasma can be incubated for 30 min. Plasma and antibody can be diluted in phosphate buffered saline and the volume can be 300 µl. Diluted sample can be run and analyzed on a flow cytometer capable of small particle detection, such as the Apogee A50MicroPlus and the CytoFlex. Flow cytometry gates for acquiring sample number can be generated using control samples, such as isotype controls, plasma, and healthy volunteer plasma. The number of extracellular vesicles positive for tissue specific markers and polySia can be acquired and results can be distributed to medical staff (e.g., doctors, nurses, and/or pharmacists). The total time from blood collection to test results can be 1 hour. The methods described herein can be performed in a hospital setting or by an outside testing company. In some embodiments, the methods described herein may be performed using a test kit that includes a mixture of fluorescently labeled antibodies, e.g., antibodies against tissue specific markers, polySia, and isotype controls. The test kit can further include an analysis template with pre-set gates, which can be selection gates to isolate the population of interest, and gates to combine populations of interest, or gates to exclude populations which can be from healthy, plasma, and isotype controls. Testing of diluted samples can also occur through application of sample onto coverslips and fluorescent base analysis of fluorescent intensities and co-localization of fluorescence on extracellular vesicles.

Methods of Use

The methods described herein can be used to diagnose high-risk cancer (e.g., high-risk or non-indolent cancer) by detecting polySia in a liquid biopsy (e.g., blood, serum, plasma, urine, breast milk, colostrum, saliva, tears, sweat, synovial fluid, cerebrospinal fluid, lymph, tears, aqueous humor, vitreous humor, mucus, semen, vaginal lubrication, interstitial fluid, endolymph, peritoneal fluid, perspiration, feces, perilymph, or pericardial fluid sample) or a tissue biopsy (e.g., needle biopsy, whole mount tumor section, or resected tumor). The methods described herein may be used to diagnose cancer that has an increased likelihood of a negative outcome (e.g., progression, metastasis, increase in tumor volume, reversal of remission, recurrence, or mortality). Subjects that may be diagnosed using the methods described herein include subjects not previously screened for cancer, subjects not previously treated for cancer, subjects undergoing active surveillance, subjects previously treated for cancer (e.g., subjects who received intent-to-cure treatment, including surgical treatment, radiation therapy, or chemotherapy), subjects previously monitored for cancer (e.g., prostate or breast cancer) using the methods described herein, subjects previously monitored for cancer (e.g., prostate or breast cancer) using other diagnostic methods, subjects previously diagnosed with cancer (e.g., prostate or breast cancer), or subjects at risk of developing cancer (e.g., related to family history of prostate or breast cancer, exposure to carcinogens or known environmental risk factors, or advanced age).

The methods described herein may be performed one or more times to diagnose a subject (e.g., 1, 2, 3, 4, 5, 6, 7, 8, 9, 10 or more times). Subjects may be repeatedly diagnosed using the methods described herein during active surveillance. The methods described herein may be used to diagnose a subject once every three months, once every six months, once a year, once every two years, or once every three years. Subjects may be diagnosed as having high-risk or non-indolent cancer if polySia is detected in a liquid or tissue biopsy obtained from the subject. Diagnosis may be performed by measuring polySia in the sample obtained from the subject and comparing it to a known cutoff value (e.g., at least 2,000 polySia-STEAP1-PSMA positive (e.g., triple-positive) events/µl for high-risk or non-indolent prostate cancer; at least 2,000 polySia-Mammaglobin-A positive (e.g., dual-positive) events/µl for high-risk or non-indolent breast cancer) or to one or more reference values. Reference values may be obtained by measuring polySia in biological samples from patients diagnosed with low-risk cancer, high-risk cancer, and/or intermediate-risk cancer. Reference samples may be categorized as low-risk, high-risk, or intermediate-risk based on patient history or outcomes (e.g., progression, change in tumor volume, metastasis, recurrence, reversal of remission, or mortality), or based on other diagnostic methods (e.g., Gleason score, genetic testing, or biomarker analysis). Samples used for measuring reference values should be of the same tumor type as that of the subject undergoing diagnosis. Liquid biopsies may be evaluated by comparing the number of extracellular vesicles (e.g., PCEVs or BCEVs), such as microvesicles, positive for polySia and one or more tissue-specific biomarkers per unit volume (e.g., concentration) in the biological sample obtained from the subject to a known cutoff value (e.g., at least 2,000 triple-positive events/µl for high-risk or non-indolent prostate cancer; at least 2,000 dual-positive events for high-risk breast or non-indolent cancer) or to one or more reference values (e.g., 1, 2, 3, or more reference values). Liquid biopsies may also be evaluated based on measuring polySia levels in extracellular vesicles (e.g., PCEVs and BCEVs), such as microvesicles, and comparing them to those measured in reference samples. Tissue biopsies may be evaluated by comparing polySia staining intensity or staining pattern to one or more reference values (e.g., 1, 2, 3, or more reference values). Biological samples from the subject may be compared to a reference value from low-risk cancer or high-risk cancer, to reference values from both low-risk cancer and high-risk cancer, or to reference values from low-risk cancer, high-risk cancer, and intermediate-risk cancer. A subject may be categorized as having low-risk cancer if polySia measurements place the subject within one standard deviation of the low-risk reference value or below the low-risk reference value. A subject may be categorized as having high-risk cancer if polySia measurements place the subject within one standard deviation of the high-risk reference sample or above the high-risk reference sample.

Reference values may be obtained from samples from patients with known cancer diagnoses (e.g., low or high-risk) and outcomes (e.g., progression, metastasis, and recurrence data), and may be derived from a single patient sample or from pooled patient samples. Reference values may also be obtained from samples from healthy volunteers or patients with BPH. Reference values may be obtained using samples from various cancer-based biorepositories, which may also have information regarding patient outcomes (e.g., cancer recurrence or mortality) and whether patient cancers were low or high-risk. For the liquid biopsy, at least 2,000 triple positive (e.g., PSMA+ve, STEAP1+ve, polySia+ve) extracellular vesicles per microliter of sample (e.g., 2,000, 2,500, 3,000, 3,5000, 4,000, 4,500, 5,000 triple-positive events/µl or more) is indicative of high-risk or non-indolent prostate cancer; and at least 2,000 dual-positive (e.g., Mammaglobin-A+ve, polySia+ve) extracellular vesicles per microliter of sample (e.g., 2,000, 2,500, 3,000, 3,5000, 4,000, 4,500, 5,000 dual-positive events/µl or more) is indicative of high-risk or non-indolent breast cancer.

A diagnosis based on the methods described herein may be used to direct patient treatment. A diagnosis of high-risk cancer based on the methods described herein may lead to a recommendation for immediate performance of a radical therapy (e.g., surgery, such as prostatectomy or mastectomy, radiation therapy, or chemotherapy). A diagnosis of low-risk cancer based on the methods described herein may lead to a recommendation for monitoring (e.g., active surveillance) and repeated testing in 6 months or more (e.g., 6 months, 1 year, 2 years or more), or a recommendation for a non-aggressive therapy with fewer side effects (e.g., therapeutic approaches that do not involve prostatectomy or mastectomy). For example, if a subject tested for prostate cancer has less than 2,000 triple-positive events/µl (e.g., less than 2,000, less than 1,500, less than 1,000, less than 500 triple-positive events/µl or fewer), a needle biopsy of the prostate should not be performed. A subject determined to have high-risk or non-indolent prostate cancer (e.g., at least 2,000 triple positive events per microliter of sample, e.g., 2,000, 2,500, 3,000, 3,5000, 4,000, 4,500, 5,000 triple-positive events/µl or more) using the methods described herein may be recommended an initial needle core biopsy and/or an aggressive therapy, such as radical prostatectomy, radiation therapy (e.g., external beam radiation or brachytherapy), hormone therapy, chemotherapy, cryotherapy, or an anti-cancer vaccine. A subject determined to have low-risk prostate cancer (e.g., less than 2,000 triple-positive events/µl, e.g., less than 2,000, less than 1,500, less than 1,000, less than 500 triple-positive events/µl or fewer) using the methods described herein may be recommended active surveillance, which could include a blood test to measure PCEVs or other prostate cancer biomarkers and a digital rectal exam with clinical follow up. Active surveillance can include monitoring every 6 months or longer (e.g., every 6 months, 1 year, 2 years, or longer). A subject determined to have high-risk or non-indolent breast cancer using the methods described herein (e.g., at least 2,000 dual-positive events per microliter of sample, e.g., 2,000, 2,500, 3,000, 3,5000, 4,000, 4,500, 5,000 dual-positive events/µl or more) may be recommended an aggressive therapy, such as surgery (e.g., breast conserving surgery or mastectomy), radiation therapy (e.g., external beam radiation or brachytherapy), lymph node removal, chemotherapy and/or hormone therapy, HER2-targeted therapy, or cryotherapy. A subject determined to have low-risk breast cancer using the methods described herein (e.g., less than 2,000 dual-positive events/µl, e.g., less than 2,000, less than 1,500, less than 1,000, less than 500 dual-positive events/µl or fewer) may be recommended a therapy of breast conserving surgery or active surveillance using mammography and dual-positive extracellular vesicle testing. Active surveillance can include monitoring every 6 months or longer (e.g., every 6 months, 1 year, 2 years, or longer).

The methods described herein can also be used to predict and treat cancer with a high-risk of metastatic recurrence. Breast cancer patients with greater than 4,000 dual-positive extracellular vesicle events prior to treatment (e.g., greater than 4,000 dual-positive events per microliter of sample, e.g., greater than 4,000, 4,500, 5,000, 5,500, 6,000, 6,500, 7,000 dual-positive events/µl or more) would be diagnosed as having a high-risk of metastatic recurrence, and would be recommended a clinical trial therapy involving metastatic inhibitors and/or a single or double mastectomy. Prostate cancer patients with greater than 4,000 triple-positive extracellular vesicle events prior to treatment (e.g., greater than 4,000 triple-positive events per microliter of sample, e.g., greater than 4,000, 4,500, 5,000, 5,500, 6,000, 6,500, 7,000 triple-positive events/µl or more) would be diagnosed as having a high-risk of metastatic recurrence, and would be recommended a clinical trial therapy involving metastatic inhibitors.

The methods described herein can also be used in a screening assay. As liquid biopsies are low cost, they can be performed on patients undergoing monitoring for cancer, as a routine test on patients in certain demographics at risk for cancer (e.g., patients with family histories of cancer, patients in professions with an increased risk of developing cancer, patients at risk for cancers due to advanced age, e.g., increased risk of breast cancer in women over 50), or alongside other blood work as part of a yearly physical exam. As little as 1 ml of blood is needed to perform the assay, and can be collected using standard blood collection methods using EDTA blood collection tubes. Plasma can be extracted and stored at −80° C., or shipped on dry ice for storage at a secondary location. Liquid biopsies can be obtained from subjects and screened via the methods described herein. The assay would comprise analyzing a liquid biopsy from a subject (e.g., a blood sample) to detect polySia and one or more tissue-specific biomarkers depending on the cancer of interest (e.g., Mammaglobin A if screening for breast cancer; PSMA and STEAP1 if screening for prostate cancer), measuring polySia levels or the concentration of polySia-positive extracellular vesicles, such as microvesicles, and comparing the polySia measurement to a known cutoff value (e.g., at least 2,000 triple-positive events/µl for high-risk or non-indolent prostate cancer, or at least 2,000 dual-positive events/µl for high-risk or non-indolent breast cancer) or to one or more reference values. A diagnosis can then be made on the basis of the comparison, and treatment may be recommended based on the results. Reference values for use in a screening assay include reference values from age-matched healthy controls, reference values from patients with low-risk cancer of the type of cancer (e.g., prostate or breast cancer) being screened in the subject, and reference values from patients with high-risk cancer of the type of cancer being screened in the subject (e.g., prostate or breast cancer). If polySia measurements fall within one standard deviation of the high-risk cancer reference values, the subject may be diagnosed with high-risk cancer and undergo additional diagnostic testing (e.g., tissue biopsy, or genetic testing) or receive aggressive treatment. If the If polySia measurements fall within one standard deviation of the low-risk cancer reference values, the subject may be diagnosed with low-risk cancer and/or undergo additional diagnostic testing. Subjects diagnosed with low-risk cancer based on the screening assay may also undergo monitoring and repeated testing every six months to one year, or may begin a non-aggressive treatment with few side effects. If polySia measurements fall within the range of reference values observed in healthy patients, the subject may again be screened using the methods described herein during routine hospital visits. Subjects who undergo repeated testing using the methods described herein may also be evaluated to determine whether their polySia measurements change over time by comparing previous measurements to measurements obtained during subsequent testing. Increased polySia measurements over time can also be used as a measure of increased risk.

The methods described herein may be used to diagnose a subject with high-risk or non-indolent cancer, or to risk stratify subjects prior to treatment. The methods described herein may also be used to monitor a subject with cancer (e.g., a subject undergoing active surveillance). A subject monitored using the methods described herein may be initially diagnosed as having low-risk cancer based on the methods described herein, and then diagnosed using the methods described herein every six months (e.g., once every six months, or once a year) to determine whether the cancer is "upgrading" or progressing as compared to results from previous diagnoses (e.g., polySia measured in a biological sample obtained from a subject will be compared to one or more reference values and to the previous measurements obtained from the subject). Cancer in a subject may be deemed to have upgraded or increased in risk if polySia measured in a biological sample from the subject is observed to increase over time compared to the subject's previous measurements, or if the polySia measured in a biological sample from the subject was initially below or within one standard deviation of the low-risk reference value and is later found to be higher than one standard deviation from the low-risk reference value. The methods described herein may also be used to evaluate the efficacy of cancer treatment in a subject. A subject treated for cancer may be diagnosed using the methods described herein during or after treatment to determine whether the treatment is effective. A subject may be diagnosed using the methods described herein before treatment, in which case polySia measurements obtained during or after treatment using the methods described herein can be compared to the pre-treatment values to determine treatment efficacy. Reduced polySia values during or post-treatment would indicate treatment efficacy, while similar or higher values would indicate that treatment may not be working, and could lead to a recommendation that treatment be adjusted or changed. If a subject was diagnosed as high-risk before treatment based on another method (e.g., Gleason score, genetic testing, or biomarker analysis), then the subject can be diagnosed using the methods described herein during or after treatment to determine if disease status has changed (e.g., if the subject is still diagnosed as high-risk or has downgraded to intermediate or low-risk).

The methods described herein can be used in combination with other diagnostic approaches to more accurately risk-stratify subjects with cancer. One diagnostic method that can be combined with the methods described herein is the PSA test. The PSA test can detect prostate cancer in subjects having PSA levels of 18 ng/ml or higher, but has poor diagnostic accuracy in the range of 4-18 ng/ml. In some embodiments, subject found to have a PSA level of >2-4 ng/ml (depending on age and race) and <18 ng/ml using the PSA test (e.g., 2, 3, 4, 5, 6, 7, 8, 9, 10, 11, 12, 13, 14, 15, 16, or 17 ng/ml, e.g., >2 to <18 ng/ml, >4 to <10 ng/ml, or ≥10 to <18 ng/ml) is further evaluated using a liquid biopsy described herein (e.g., a liquid biopsy for polySia and one or more (e.g., 1, 2, 3, or more) prostate-specific biomarkers (e.g., STEAP1 and/or PSMA)). If the subject has at least 2,000 triple-positive extracellular vesicles per microliter of sample (e.g., 2,000, 2,500, 3,000, 3,500, 4,000, 4,500, 5,000 triple-positive events/µl or more) the subject can be diagnosed as having high-risk or non-indolent prostate cancer and recommended for immediate, aggressive therapy (e.g., prostatectomy or radiation therapy). If the subject has less than 2,000 triple-positive events/µl (e.g., less than 2,000, less than 1,500, less than 1,000, less than 500 events/µl or fewer) and a PSA level of ≥2 and <18 ng/ml, it is indicative of low or no disease burden, a needle biopsy of the prostate is not performed, and the subject is placed on active surveillance. In some embodiments, a diagnosis of prostate cancer risk can be performed based on both the PSA test and the liquid biopsy described herein. For example, if a subject has PSA levels of ≥18 ng/ml and at least 2,000 triple-positive extracellular vesicles per microliter of sample (e.g., 2,000, 2,500, 3,000, 3,500, 4,000, 4,500, 5,000 triple-positive events/µl or more) in a liquid biopsy described herein, the subject can be can be diagnosed as having high-risk or non-indolent prostate cancer and recommended for immediate, aggressive therapy (e.g., prostatectomy or radiation therapy). Combining these two assays may reduce the number of false negatives (e.g., the number of subjects with high-risk cancer who are not categorized as high risk when only one assay is used).

The methods described herein provide a high level of accuracy in diagnosing high-risk or non-indolent cancer. The liquid biopsy described herein will have an accuracy of 68% or greater (e.g., 68%, 70%, 75%, 80%, 85%, 90%, 95%, 97%, 98%, 99%, or more) in identifying patients whose cancer evolves to a high-risk phenotype whilst on active surveillance, thus requiring intent-to-cure therapy (e.g., surgery, radiation therapy, chemotherapy). The methods described herein may provide results that are at least 5% more accurate (5%, 10%, 15%, 20%, 25%, 30%, 40%, 50%, 75%, or 90% or more accurate) than results obtained using other diagnostic methods (e.g., diagnosis based on PSA or Gleason score).

The methods described herein can be performed within 10 minutes of a liquid biopsy (e.g., blood or semen collection) (e.g., within 10, 15, 20, 30, 45, 60, 120, 180, 240, 300, 360, 420, or 480 minutes of a liquid biopsy). The methods described herein can also be performed within 1, 2, 3, 4, 5, 6, or 7 days of a liquid biopsy (e.g., blood or semen collection). Cancer extracellular vesicles are cell fragments and will not be destroyed by freeze-thaw cycles, therefore, the methods described herein can be performed at any time after liquid biopsy as long as samples are properly maintained (e.g., 6 months, 1 year, 2 years, 3 years, 5 years, 10 years, 20 years or more after blood or semen collection). Thus, the methods described herein can provide rapid diagnostic results to direct patient treatment and retrospective diagnostic results that may aid in understanding patient history and performing longitudinal or scientific studies.

Kits

The methods described herein may be performed using a kit for use in diagnosing high-risk or non-indolent cancer. The kit may include cancer-specific (e.g., polySia) and tissue-specific (e.g., PSMA and STEAP1, or Mammaglobin A) antibodies and isotype control antibodies. The kit can further include a package insert that instructs a user of the kit, such as a pathologist or pathology lab technician, to perform the methods described herein. Kits for use in nanoscale flow cytometry may also include beads to help establish sizing gates.

EXAMPLES

The following examples are put forth so as to provide those of ordinary skill in the art with a description of how the methods described herein may be used, performed, and evaluated, and are intended to be purely exemplary of the invention and are not intended to limit the scope of what the inventors regard as their invention.

Figure 3A:
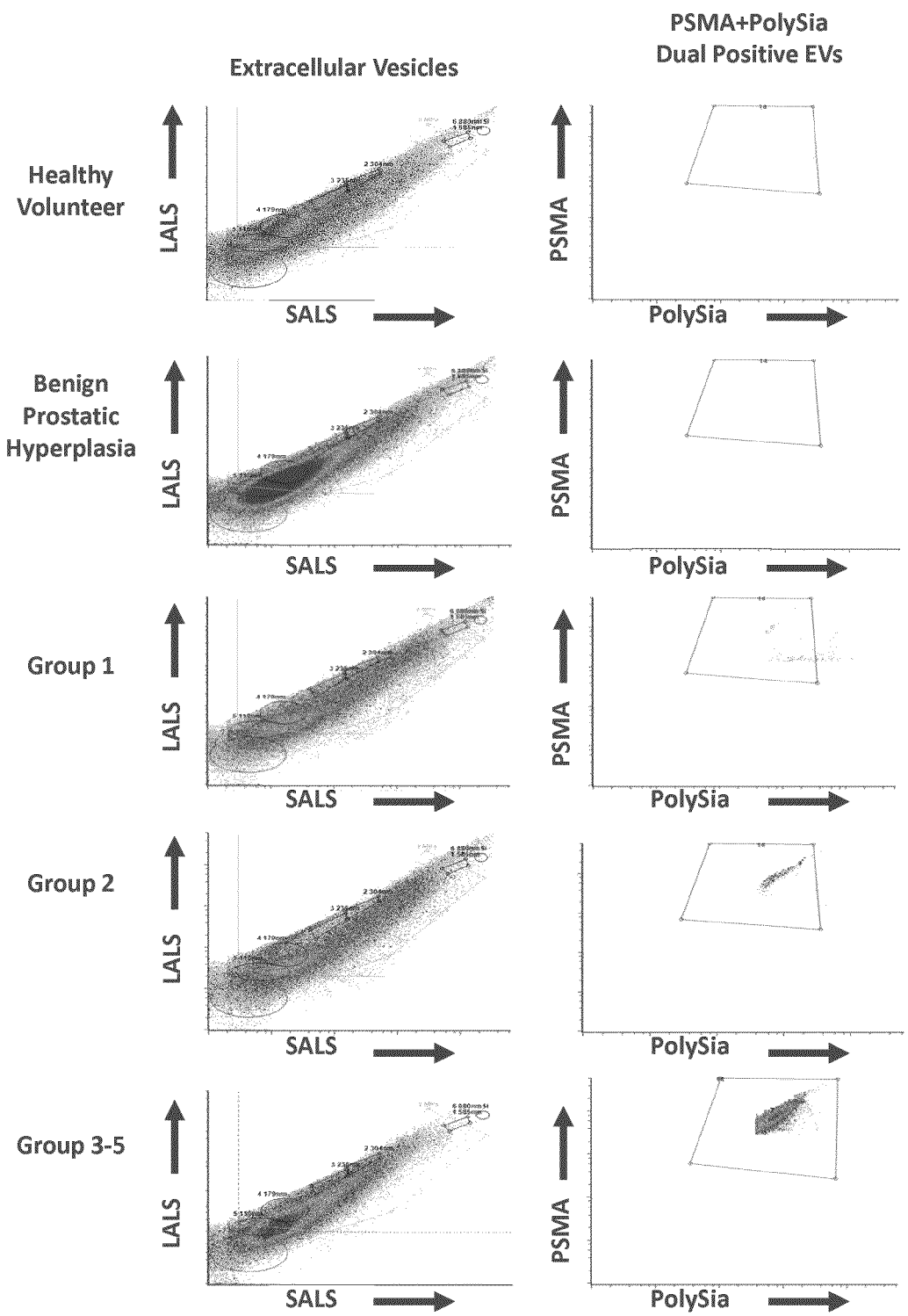

Example 1. PSMA-polySia Dual-Positive Extracellular Vesicles Positively Correlate with Gleason Score Plasma samples from 14 healthy controls, 20 benign prostate hyperplasia (BPH), and 81 patients with PCa, of which 28 are low-risk (GGS: 1), 29 intermediate-risk (GGS: 2), and 24 high-risk (GGS: 3-5) were immunostained with an antibody for the extracellular domain of prostate specific membrane antigen (PSMA) and a lectin-GFP fusion protein which binds polySia (GFP-EndoNDM). The endosialidase (EndoN) comes from an $E.$ $coli$ K1-specific bacteriophage and specifically hydrolyzes $\alpha 2,8$-linked polySia. The catalytically inactive enzyme, EndoNDM, serves as a lectin that binds polySia with a Kd of $10^{-8}$ M and has been used to detect polySia in cells. The population of PSMA-polySia dual-positive extracellular vesicles were found to positively correlate with Gleason Group score (GGS) (FIG. 1, FIGS. 3A-3B). Healthy controls and BPH patients exhibited the lowest number of dual positive PMP levels in plasma. Most importantly, PSMA-polySia extracellular vesicle counts increased as GGS pattern increased from GGS 1-2 (low-risk PCa) to GGS 3-5 (high-risk PCa) ($P<0.05$), revealing the nature of polySia expression over a cancer progression continuum (FIGS. 3A-3B). The rate of false positives was less than 15% in healthy volunteers, BPH and GGS 1 (threshold value set at 0.10). When compared to an estimated false positive rate of 19.8% using the PSA test, this method yields a substantial improvement in diagnostic accuracy. Our data identify high-risk individuals based on their GGS at time of biopsy and show a correlation between GGS and liquid biopsy results.

Example 2. polySia is Expressed in Prostate Cancer Cell Lines

Figure 2:
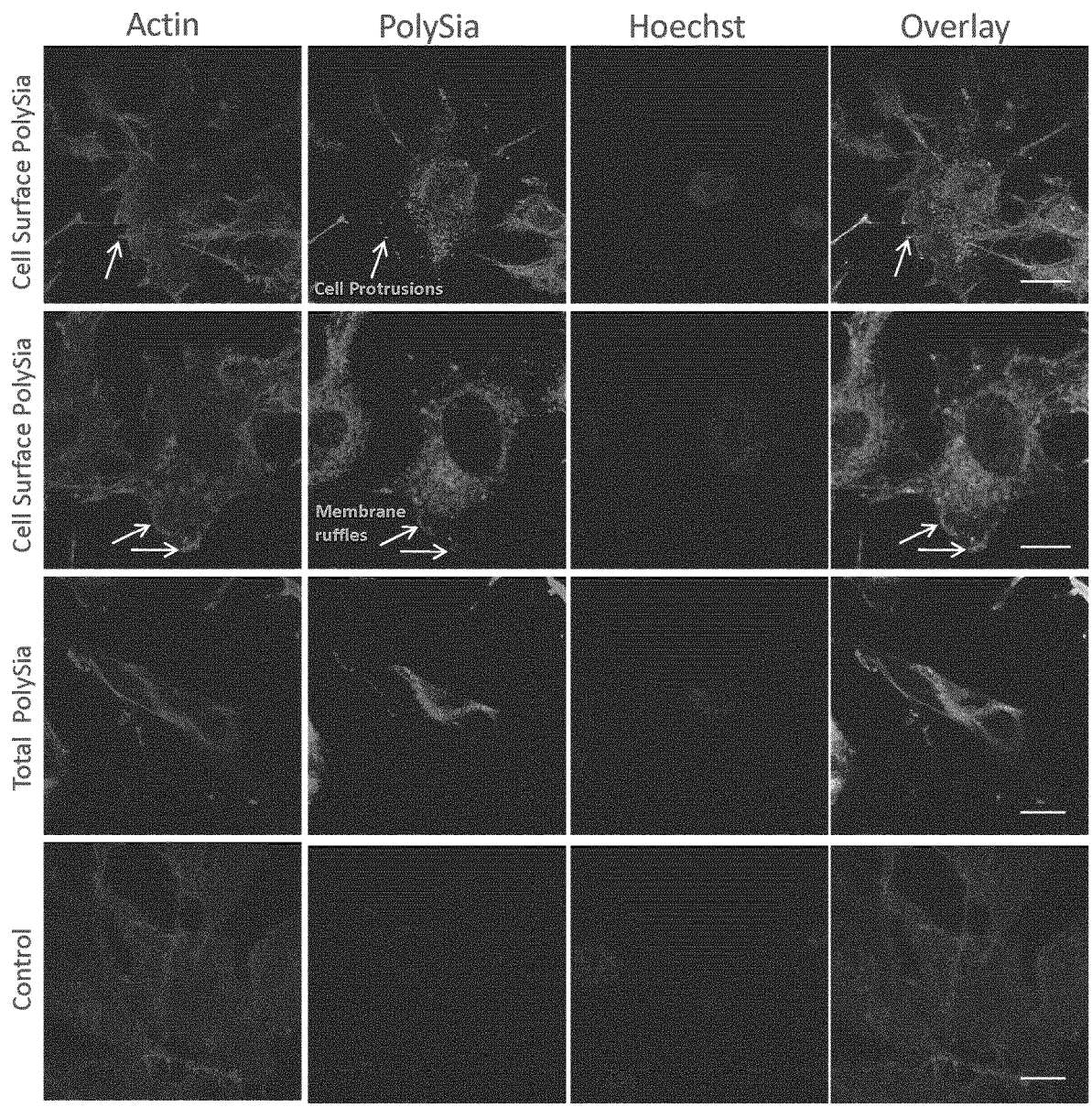
FIG. 2 is a series of images demonstrating that polysialic acid is present on the aggressive prostate cancer cell line PC3MLN4. Cell surface polySia was observed in PC3MLN4 cells by incubating with a catalytically inactive enzyme with specific binding to polySia—GFP-EndoN$_{DM}$ for 30 min, followed by fixation, permeabilization and labeling of actin with rhodamine phalloidin (1st and 2nd row). Total polySia was observed by fixing and permeabilizing cells, followed by incubating with GFP-EndoN$_{DM}$ and rhodamine phalloidin (3rd row). As a negative control, cells were treated with active EndoN endosialidase to hydrolyze polySia for 1 h prior to fixation, followed by staining with GFP-EndoN$_{DM}$ and rhodamine phalloidin (4th row). Arrows in row 1 indicate membrane punctate staining of polySia. Arrows in row 2 show polySia localizing to membrane ruffles. Row 4 shows a lack of GFP-EndoN$_{DM}$, indicating efficient sialidase cleavage and specific polySia signal in rows 1-3. Cells were imaged using confocal microscopy. Scale bar represents 10 μm.
Figure 5:
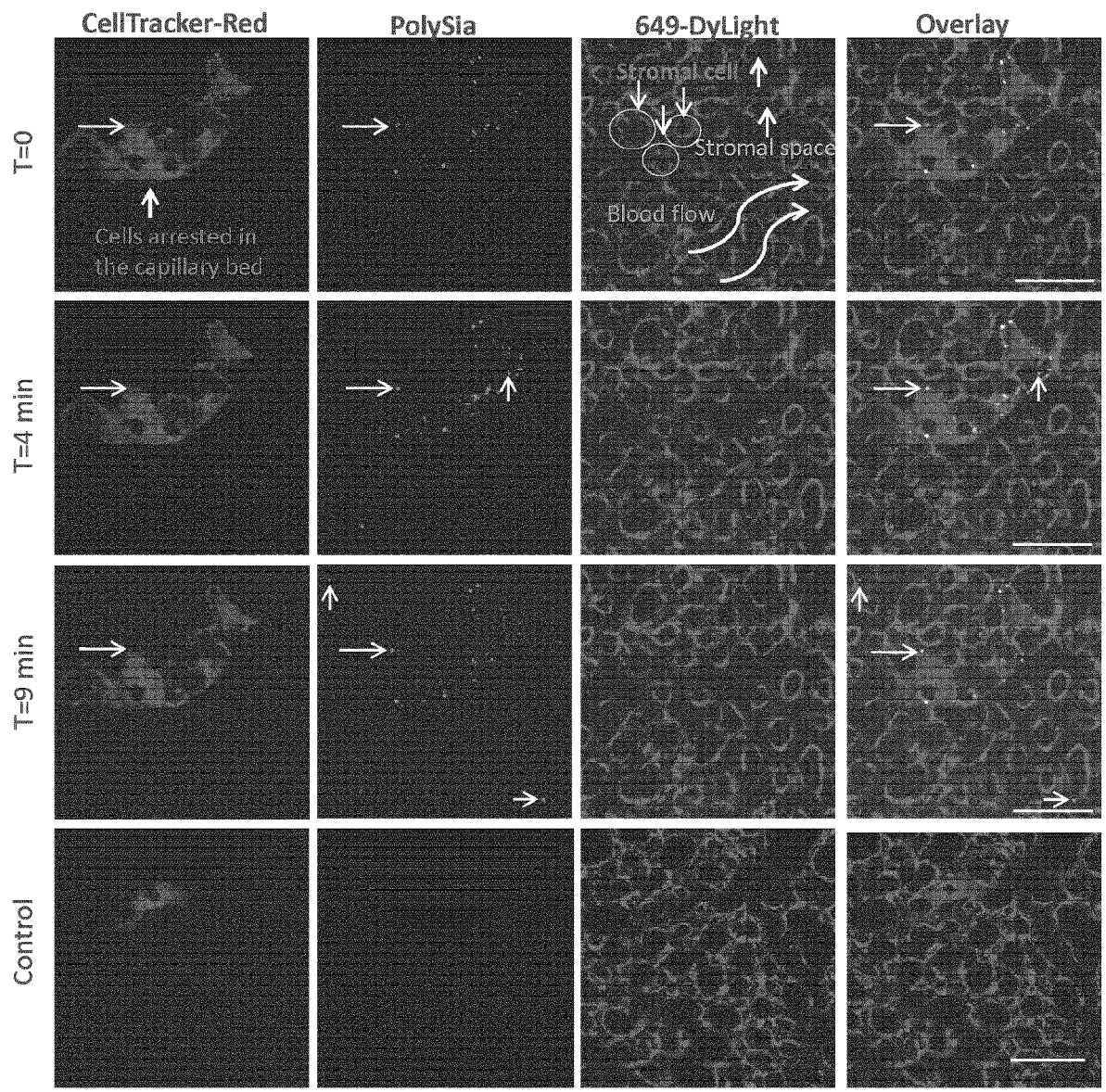
FIG. 5 is a series of images depicting polysialic acid extracellular vesicles release from PC3MLN4 cells. PC3MLN4 cells were incubated with GFP-EndoN$_{DM}$ for 30 min and cells were labeled with CellTracker-Red. The cells were extensively washed and injected into a vein within the chorioallantoic membrane (CAM) of the avian embryo. Two hours post-cell injection, embryos were injected with 649-DyeLight, a lectin which binds to the vascular endothelial cells. Real-time imaging of cells in the vasculature of the CAM was performed using confocal microscopy. Represented cells are arrested in the capillary bed and the stromal cells are seen in magenta (red circles on top row). To give an indication of blood flow in the capillary bed, curved arrows are drawn in the first row to aid in visualization. Top 3 rows represent images taken during a time course. The long arrow shows polySia on the cell surface ($1^{st}$ row), which moves to the periphery of the cell (2nd row) before being released at the plasma membrane ($3^{rd}$ row). Short arrows show extracellular vesicles which have been released from the cells and are in the vasculature. As a negative control ($4^{th}$ row), polySia was cleaved with EndoN endosialidase prior to labeling with GFPEndoN$_{DM}$ and CellTracker-Red. These cells were injected into the CAM, and processed as above. The lack of GFP-EndoN$_{DM}$ signal is due to efficient endosialidase cleavage of polySia. Scale bar represents 20 µm.
Figure 6:
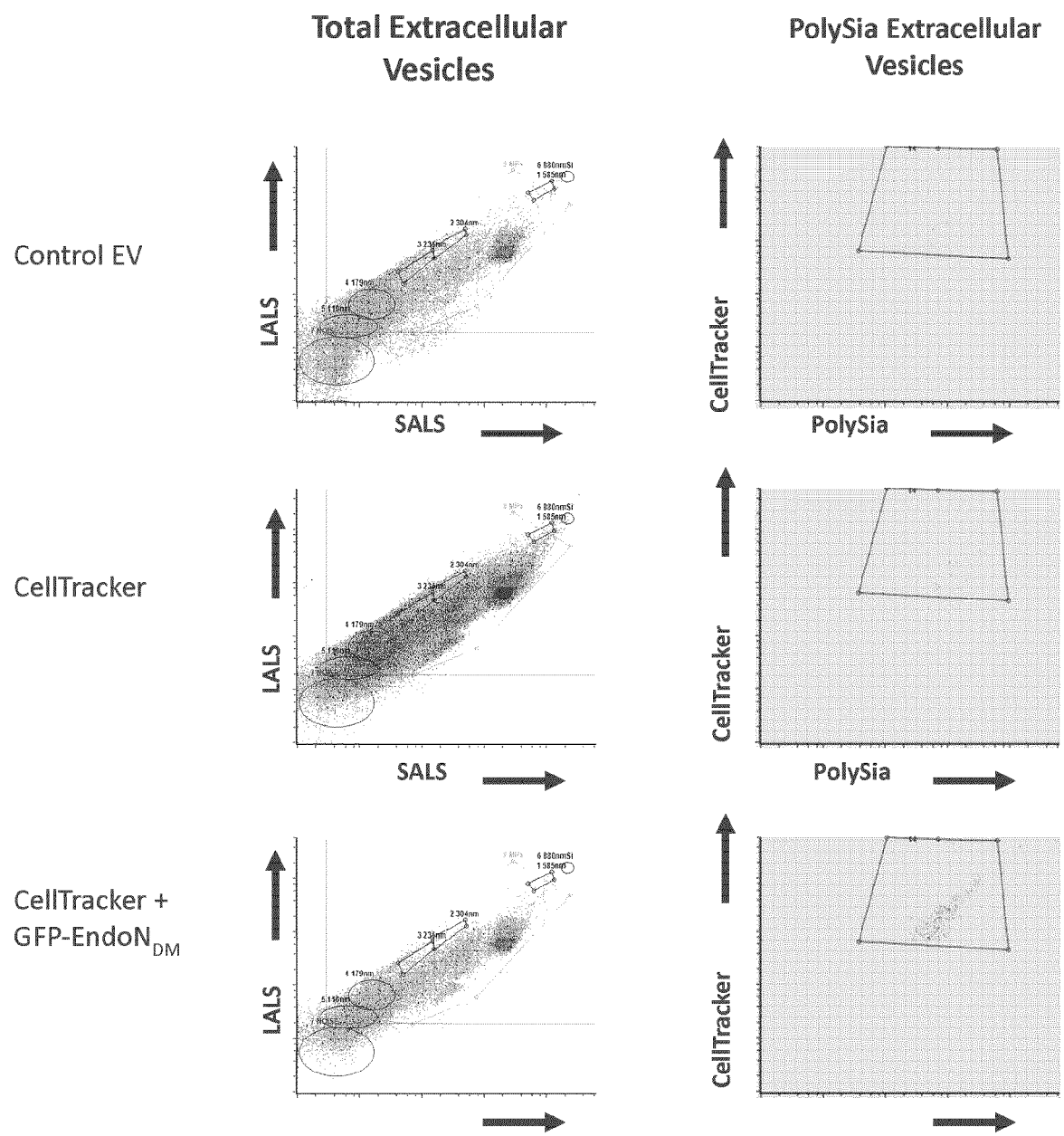
FIG. 6 is a series of graphs demonstrating that extracellular vesicles or extracellular vesicles released by cultured PC3MLN4 are polysialylated in vitro. PC3MLN4 cells were either left untreated ($1^{st}$ row), treated with CellTracker-Red ($2^{nd}$ row) or CellTracker-Red and GFP-EndoN$_{DM}$ ($3^{rd}$ row). Cells were cultured for 24 h and extracellular vesicles where collected by removal of cell culture media. 20 µL of cell culture media was diluted 1:7 in dH$_2$O and analyzed by nanoscale flow cytometry. Bivariate plots of representative samples are shown. Left column represents the total extracellular vesicle population (extracellular vesicles). Extracellular vesicles (outlined rectangular area in graphs on left) were gated based on sizing standards and output to the right column. The outlined area in the right column represents extracellular vesicles positive for both CellTracker-Red and polySia. 1st row represents extracellular vesicles from untreated PC3MLN4 cells showing no signal in the selected regions (red outlined areas). $2^{nd}$ row represents extracellular vesicles from PC3MLN4 cells treated with CellTracker red only. $3^{rd}$ row represents cell extracellular vesicles from PC3MLN4 cells treated with CellTracker-Red and GFP-EndoN$_{DM}$. A dual-positive population is clearly identifiable in the selected region (red outlined area).

The presence of polySia on PCa cell lines has not been reported. Expression of polySia on the PC3MLN4 human metastatic prostate cell line was found with anti-polySia IgG and fluorescence confocal microscopy (FIG. 2). PolySia exhibits a punctate distribution on the plasma membrane, which is in contrast to its more uniform distribution observed across the entire cell surface of neuronal cells, suggesting that different proteins may be polysialylated in PC3MLN4 cells. The localization of polySia to membrane protrusions and ruffles (FIG. 2, first and second row, respectively) in PC3MLN4 cells is intriguing as these are rich in lipid rafts and have important roles in cell signaling, potentially implicating polySia in a functional role in aggressive cancers. PC3MLN4 cells were also evaluated for their ability to produce polysialylated extracellular vesicles in vivo. Using an established avian embryo model, PC3MLN4 cells were pre-treated with GFP-EndoNDM and polySia was observed on the surface of the PC3MLN4 cells arrested within capillary beds and on extracellular vesicles released by individual tumor cells when intravenously injected into the chorioallantoic membrane and intravitally imaged using real-time confocal microscopy (FIG. 5). Detection of poly-Sia extracellular vesicles from PC3MLN4 cells was also confirmed by nanoscale flow cytometry (FIG. 6). Overall, these data strongly suggest the analysis of polySia on extracellular vesicles derived from PCa cells can form the basis of a novel assay for diagnosis and monitoring of PCa. This assay has the potential to be a general platform for stratification of other high-risk cancers, such as breast cancer.

Example 3. Powered Retrospective Analyses of Prostate Cancer Patient Plasmas

We can perform a fully powered retrospective analysis of randomized and de-identified patient plasmas to eliminate processing bias. To power a study in which the desired AUC curve (specificity vs. sensitivity) is 85% accurate across the Gleason score ≥8 patient cohort requires greater than 76 patients in each Gleason category, where 65 patients will be accurately identified in our assay for high-risk PCa. We anticipate an AUC 95% confidence interval of 0.79-0.96 under these conditions. In total, we will require 456 patient plasmas which can be obtained from ProCURE foundation, QC, which has all of these patient plasmas with at least 3 years of clinical follow-up for each sample. An additional cohort of patient plasmas collected at baseline prior to radical therapy (prostatectomy, radiation therapy, N≥76) from patients who exhibited early cancer recurrence (<3 years) can also be obtained from various cancer based biorepositories and analyzed. This represents an important cohort of plasmas from patients with cancer that recurred independent of the Gleason score of the primary tumor.

Example 4. Identification of polySia on Breast Cancer Extracellular Vesicles

Figure 18:
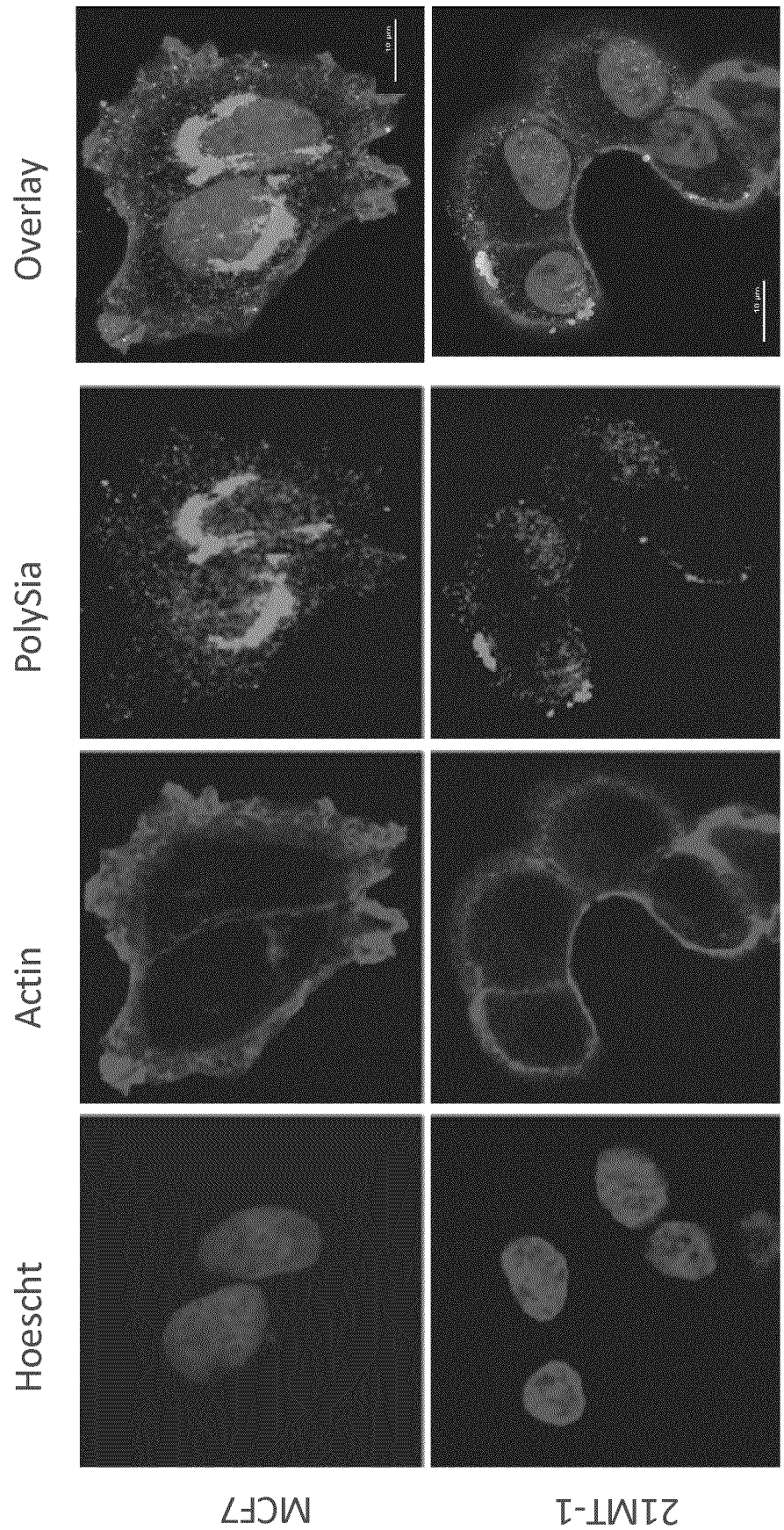
FIG. 18 is a series of images demonstrating that polysialic acid is present on the breast cancer cell lines 21MT-1 and MCF-7. Total polySia was observed by fixing and permeabilizing cells, followed by incubating with anti-polySia antibodies, followed by Alexa488 secondary antibodies and rhodamine phalloidin to stain actin. Cells were imaged using confocal microscopy. Scale bar represents 10 µm.

Breast cancer cell lines (21MT-1 and MCF7) were treated with anti-polySia and imaged with confocal microscopy to determine the presence of polySia. Identification of the presence of polysialylated breast-derived extracellular vesicles was done from the cell culture media. Breast cancer patient plasmas were obtained from Dr. Chambers of the London Regional Cancer Program and analyzed to correlate polySia levels on extracellular vesicles with the stage of disease (FIG. 18).

Example 5. Prostate Cancer Extracellular Vesicles as a Biomarker Platform for "Liquid Biopsies"

Our group is the first to develop techniques and instrumentation for the enumeration of biomarker-decorated tumor extracellular vesicles, such as microvesicles, in patient plasmas. We recently demonstrated that extracellular vesicle events which express prostate specific membrane antigen (PSMA), a prostate tissue specific biomarker, are abundant in plasmas from patients with benign prostatic hyperplasia (BPH, enlarged prostate gland and PSA>4 ng/mL), Gleason Group 1-5 prostate cancer, and metastatic prostate cancer (naïve treated and castrate resistant patient cohorts). While this first generation "liquid biopsy" was unsuccessful due to its inability to distinguish healthy volunteers and patients with BPH from localized PCa, it revealed that patients with GGS ≥3 disease have the highest levels of PSMA+ve extracellular vesicles in their plasma. To improve on this, we have recently developed a next generation version of this "liquid biopsy" in which we now define prostate cancer extracellular vesicles (PCEVs) as co-expressing two prostate tissue biomarkers, PSMA and STEAP1 (six transmembrane epithelial antigen of the prostate 1), and polysialic acid, a cancer biomarker. To enumerate these triple positive extracellular vesicle events in patient plasma samples, we use nanoscale flow cytometry (Apogee FlowSystems Inc.), which is a specialized form of flow cytometry originally intended to analyze air for airborne pathogens. This instrument has three lasers (405 nm, 488 nm, 643 nm) and 5 different filter-based PMT detectors that permit multi-parametric analyses with commonly used fluorescent dyes such as FITC, R-PE, Alexa based dyes, and Hoechst. The sizing resolution of this instrument is impressive, it enables us to resolve extracellular vesicle subpopulations to within 50 nm, and can analyze ~20,000 events/second over an event diameter range of 100 nm to 1,200 nm. Our analyses have revealed that PCEVs are typically between 250 nm to 550 nm in diameter (FIG. 7). Analysis of each sample, when analyzed with its isotype stained negative control, only takes 4 minutes for analysis (~5×10$^6$ events/run), and provides data in an event/μL of plasma format. Equally important is that each analysis only consumes 20 μL of plasma, and since this technique is microscaled, only nanogram quantities of tissue-specific antibodies and cancer-specific antibodies are required, making high-throughput and large scale experiments logistically and economically feasible. Moreover, because extracellular vesicles are essentially cell fragments that can no longer undergo further degradation by multiple freeze-thaw cycles, large scale retrospective analyses of biobank collections of patient sera or plasma samples can be analyzed in a relatively short time frame.

The polySia-based "liquid biopsy" blood test has been optimized and standardized to become a CLIA-certified test. First, the amount of sera/plasma consumed per test is 40 μL. Half of this is incubated with negative isotype control antibodies, mouse IgG-Alexa488 (610 ng/sample) and mouse IgG2a-RPE (280 ng/sample). The other half is incubated with anti-PolySia mouse IgG1-Alexa488 antibody (610 ng/sample), anti-STEAP1 mouse IgG1-Alexa647 (150 ng/sample, in-house hybridoma) and anti-PSMA IgG2a (280 ng/sample; clone 3E/7, in-house hybridoma). Both sets of stained samples are incubated in the dark for 15 minutes, then 600 μL of ddH2O is added as diluent and then the entire sample is analyzed by the A50-Micro Nanoscale Flow Cytometry instrument (Apogee FlowSystems Inc., UK). The isotype sample is always analyzed first to establish gates, whereby the Alexa647 vs. RPE scatterplot has the rectangular gate positioned such that minimal dual-positive events are present in it but the gate itself is immediately above the other two populations of extracellular vesicles that do not exhibit significant Alexa647/RPE signal. Dual positive events are then gated to determine the number of events that also express Alexa488 (polySia) signal. These triple positive events are defined as PCEVs. Calibration silica beads (110, 180, 230, 350, 450, 600, 880, 1200 nm) are analyzed as a forward scatter flow check. A standardized sample of extracellular vesicles from prostate cancer cell line LNCaP is analyzed prior to the batch of samples. This is performed to ensure that the amount of antibody is proportionate and controlled for all samples analyzed for any comparison to be made. After the batch run, ddH2O is analyzed to ensure that no residual samples are analyzed. Every attempt is made to ensure that the same micropipettes, tips, antibody lots, diluent lots, and calibration bead lots are used for experiments.

Example 6. Clinical Validation of the polySia Biomarker for Use in Active Surveillance To compare the utility of MRI and the "liquid biopsy" to current standards of care (e.g., PSA blood test, tissue biopsy) and determine which method is most accurate in identifying patients whose PCa becomes upgraded during active surveillance, we can perform a clinical study. Patient plasmas are to be collected at baseline and then collected in the majority of enrolled patients (Sunnybrook Hospital, London Health Sciences Centre are two key sites) at every clinical visit, with an anticipated drop-out rate of 20%. To date, >60 patients have been enrolled with >300 plasma/sera samples biobanked. This is a unique opportunity to identify patients who actually have high-risk PCa disease and should not be on AS as early as possible, as well as an opportunity to identify patients that were originally low-risk but progressed to a high-risk phenotype. There is no intervention permitted for this study regardless of the result for any patient. We can also perform immunostaining on prostate biopsies from patients recruited into this study that have also provided serial sets of plasma samples. Immunostaining can be performed on annual biopsies collected from the same patients whose initial biopsies are polySia+ve at baseline. Sets of plasma samples from patients that exhibit an increasing number of polySia+ve PCEVs over time but had a biopsy that was polySia negative can have the rest of their biopsies immunostained for polySia expression to confirm if induction of polySia expression occurred during AS or if the tumor is not amenable to biopsy thus contributing to the 20-25% error rate in biopsy. This is clinical study will provide a blood-based readout of prostate cancer progression for patients who have deferred prostatectomy in favor of an imaging (MRI) and biopsy-based monitoring program known as active surveillance, and can indicate if liquid biopsies are sensitive and accurate enough to replace needle-based biopsies for diagnosis of prostate cancer.

Example 7. Clinical Validation of the polySia Liquid Biopsy in Patients Suspected to have Prostate Cancer Patient blood samples can be obtained prior to transrectal ultrasound (TRUS)-based biopsy of the prostate. Two vacutainers (EDTA-K2 10 mL volume) are to be collected at least 30 minutes prior to needle core biopsy of the prostate, essentially making this a paired collection of whole blood and tissue biopsies at the same time. These samples can be used to determine if our liquid biopsy (e.g., blood test) is able to accurately identify all patients that are Gleason Group 3-5 (Gleason score ≥4+3) as determined by the tissue biopsy. These samples can also be used to identify patients who are positive for the polySia-based "liquid biopsy" but whose final pathology report via tissue biopsy suggests a Gleason Group 1 or 2 (Gleason score ≤3+4 tumor). Analysis of patient plasmas will be done on a batch basis. This experiment can provide a correlation between the liquid biopsy results and the tissue biopsy results.

Example 8. Clinical Validation of the polySia Biomarker for Use in a Tissue Biopsy Format Tissue microarrays (TMAs) generated from tissue biopsies from subjects having or suspected of having prostate cancer can be used to determine the predictive ability of the polySia biomarker in identifying high-risk prostate cancer patients that will exhibit early cancer recurrence after prostatectomy (less than 3-5 years). Tissue microarrays are excellent tools for evaluating biomarker specificity because they enable the user to simultaneously immunostain hundreds of tissue sections. Typically, a "core" smaller than 1 mm in diameter is removed from a specific part of a tissue block, in this case, the prostate cancer, and then is embedded like many others into a very tight, grid arrangement in a much larger paraffin-based block. In this manner, hundreds of tissue cores representing clinical outcomes (early cancer recurrence or no recurrence) or risk-types of prostate cancer along with negative control tissue cores can be organized and sections with hundreds of tiny portions of different cancers from different patients can be produced and laid out in an anonymized fashion, eliminating bias during immunostaining. Therefore, the benefit of using a TMA is that a single preparation of primary/second antibody can be laid onto individual tissue sections from this assembled TMA, which significantly reduces any variability of antibody treatment being applied to the tissue sections. Such a TMA also reduces and resources spent on tissue, antibody, sectioning of individual tissue blocks, ensuring that these sources of technical variability are minimized as well.

Example 9. Isolating Cancer Extracellular Vesicles from a Liquid Biopsy

A liquid biopsy (e.g., blood sample) can be obtained from a subject with cancer (e.g., prostate cancer) using standard methods employed by those skilled in the art. The blood sample (e.g., 20 μL of the blood sample) can be stained for a cancer-specific biomarker (e.g., polySia) and tissue-specific biomarkers (e.g., PSMA and STEAP1) using fluorescent antibodies. The blood sample (e.g., 20 μL of the remaining un-stained blood sample) can also be stained for isotype control antibodies. The stained samples can then be analyzed using nanoscale flow cytometry to visualize events corresponding to cancer extracellular vesicles (e.g., prostate cancer extracellular vesicles) and the extracellular vesicles can be collected and isolated using fluorescence activated cell sorting (FACS).

Statistical Analyses

Each hypothesis has a specific target true positive population. For example, the true positive population in the both hypotheses is patients that exhibited early biochemical recurrence within 5 years of prostatectomy and/or Gleason Groups 3-5 PCa. Accuracy of the anti-PolySia mAb can be evaluated by =(true positives+true negatives)/total population. Sensitivity (true positive rate) can be determined by =true positives/actual number of positives. The accuracy and sensitivity rates can be compared to the CPCBN biomarker panel for aggressive PCa, which describes four different subtypes of PCa risk in the form of DNA-based signatures, leading to an AUC of 0.68 (95% confidence interval of 0.63-0.73) when used to identify patients at risk of early biochemical recurrence within 18 months from two independent validation cohorts from MSKCC and Cambridge.

Figure 8A:
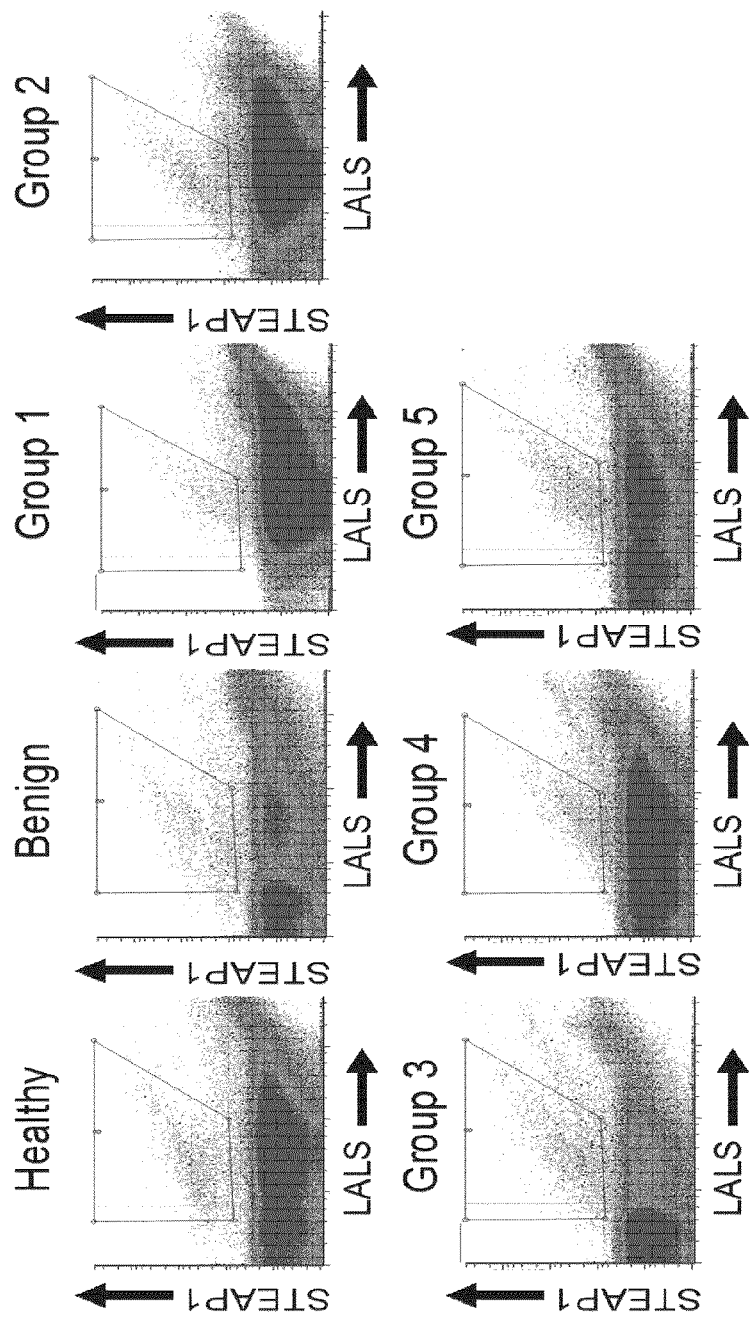
Figure 8B:
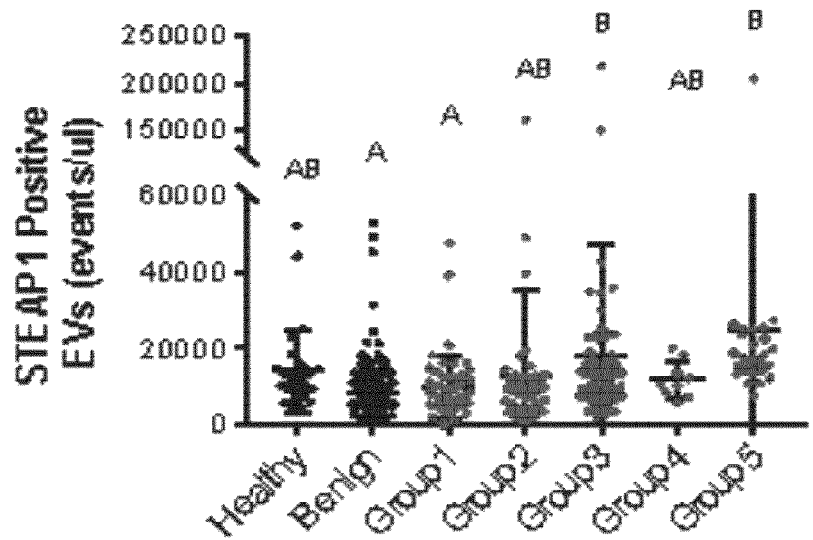
Figure 8C:
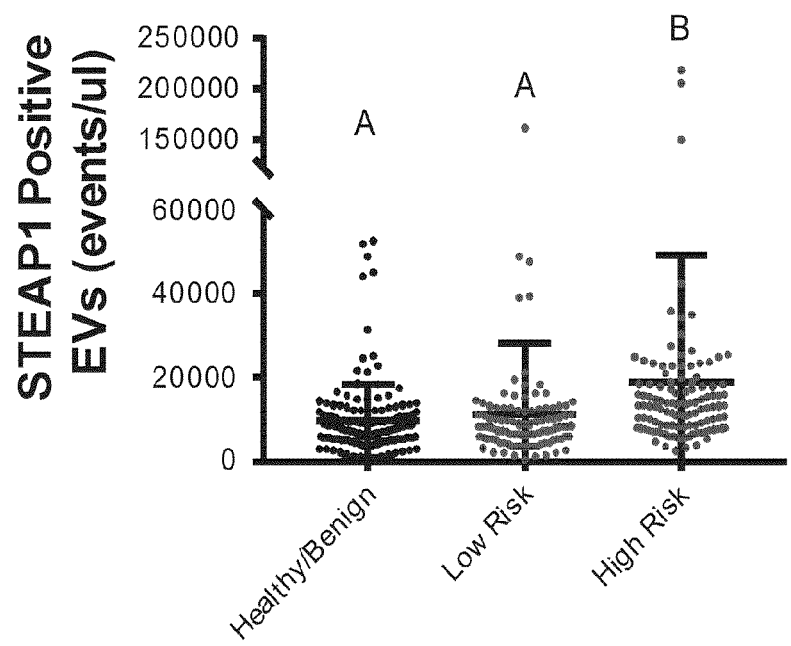

Example 10. STEAP1 Expression Levels on Extracellular Vesicles and Prostate Cancer Tissue Identification and analysis of STEAP1 positive extracellular vesicles was performed using nanoscale flow cytometry. We have previously described this technique for enumerating extracellular vesicles in plasma samples. To assess STEAP1 extracellular vesicle levels in prostate cancer a discovery cohort of 378 plasma samples was obtained and analyzed by nanoscale flow cytometry. The discovery cohort consisted of: 27 healthy, 128 benign, 53 Group 1, 51 Group 2, 83 Group 3, 9 Group 4, and 27 Group 5 plasma samples. All patients had histologically validated Gleason scores derived from prostatectomy specimens and all plasma samples were collected prior to surgery. STEAP1-positive extracellular vesicles were readily detected in all plasma samples and the number of events/μl of plasma increased from healthy to Group 5 (Mean values: healthy-8726, benign-9905, Group 1-5: 12679, 18091, 11852, and 24764, respectively) (FIGS. 8A-8B). STEAP1 extracellular vesicle levels were found to be significantly higher in Groups 3 and 5 compared to Benign and Group 1 ($p<0.05$) (FIG. 8B). Risk stratification of patients into low-risk (Group 1 and 2) versus high-risk (Group 3-5) showed that high-risk individuals had significantly elevated STEAP1 extracellular vesicle levels compared to low-risk ($p=0.0069$) and healthy/benign ($p=0.0004$) individuals (FIG. 8C).

Figure 8D:
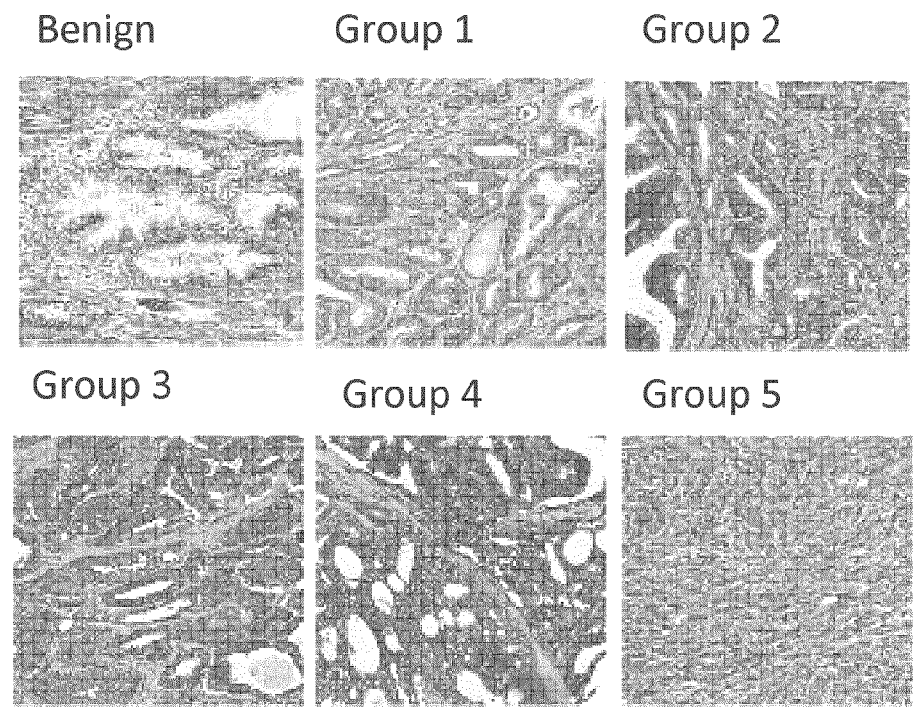
Figure 8E:
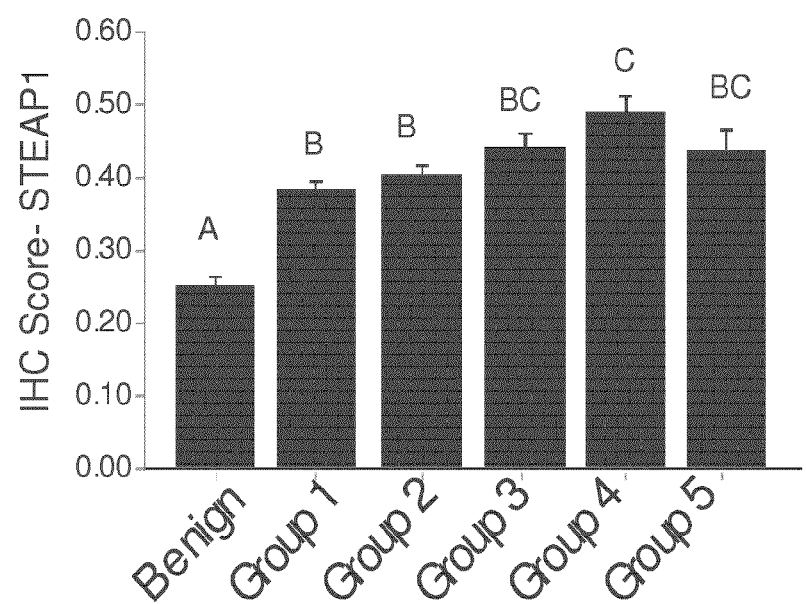
Figure 8F:
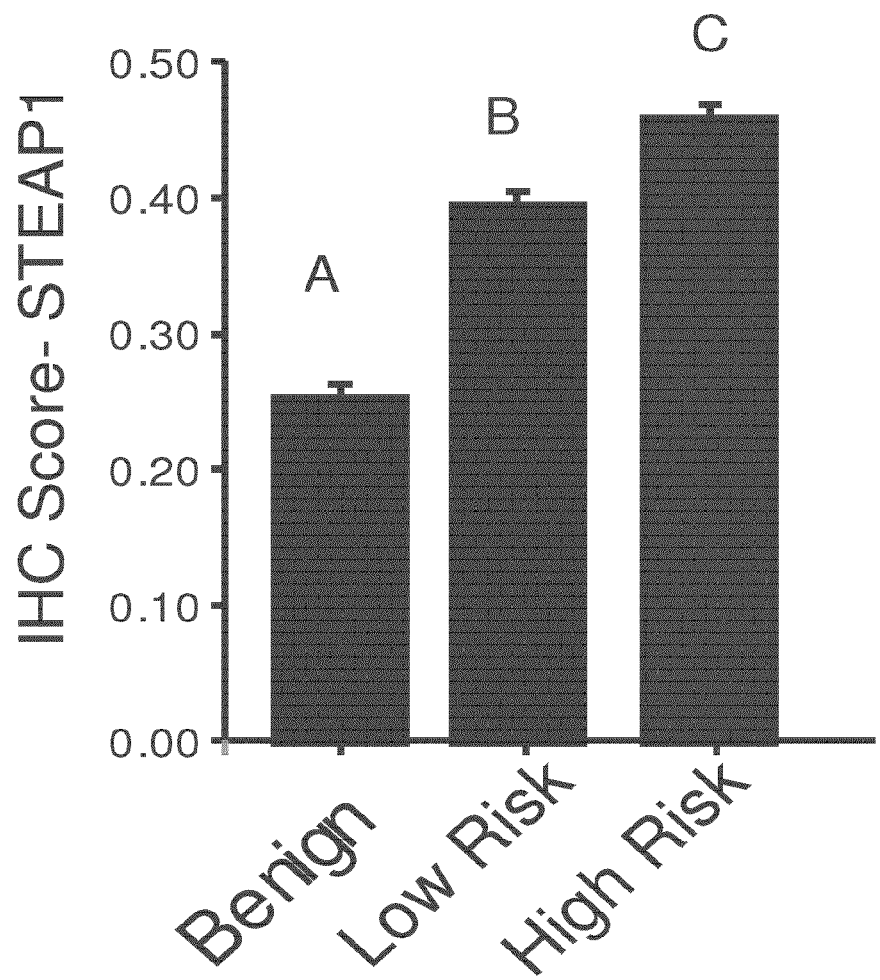

To determine if STEAP1-extracellular vesicle levels correlated with STEAP1 expression levels in prostate cancer, a tissue microarray (TMA) consisting of 1091 cores was stained and analyzed (FIG. 8D). Prostate cores from 218 benign, 326 Group 1, 217 Group 2, 128 Group 3, 135 Group 4 and 67 Group 5 were represented in the TMA. STEAP1 levels on tissue cores were found to increase with Group score, with Benign tissue have significantly lower expression levels compared to Group 1-5 ($p<0.001$) (FIG. 8E). Risk stratification of patients into low-risk and high-risk groups demonstrated that high-risk individuals had significantly higher STEAP1 expression levels compared to low-risk and benign ($p<0.01$) (FIG. 8F). Elevated levels of STEAP1 were found on both tissue and extracellular vesicles, suggesting that STEAP1 may be a negative prognostic factor. To determine if STEAP1 expression levels correlate with disease progression a Cox regression analysis was performed. Greater than 10 years of clinical follow-up data was available for all patients and patient outcome was matched to their corresponding tissue core. Analysis of STEAP1 levels showed a significant reduction in recurrence free survival for individuals with high STEAP1 expression levels ($p=0.01$), further validating STEAP1 as a biomarker for aggressive, high-risk, prostate cancer (FIG. 8G).

Figure 9A:
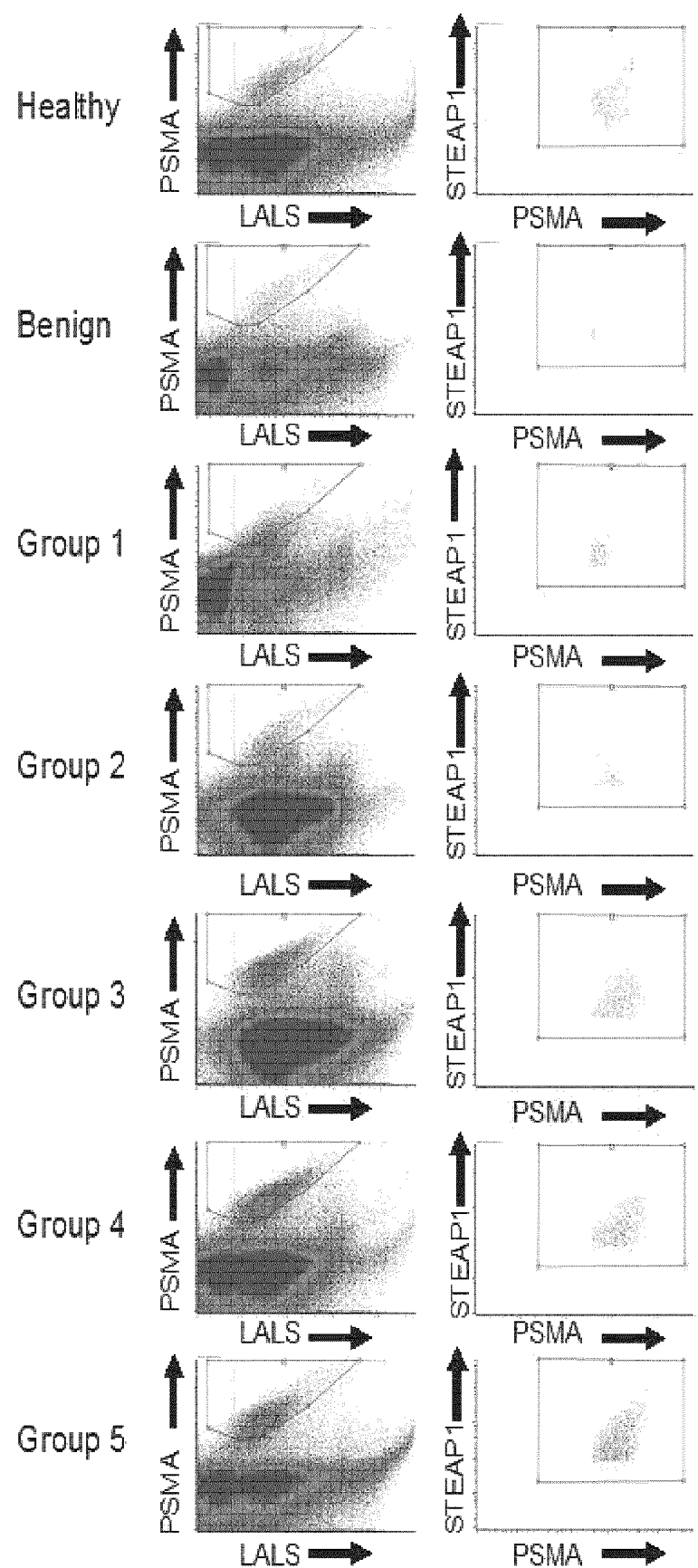
Figure 9B:
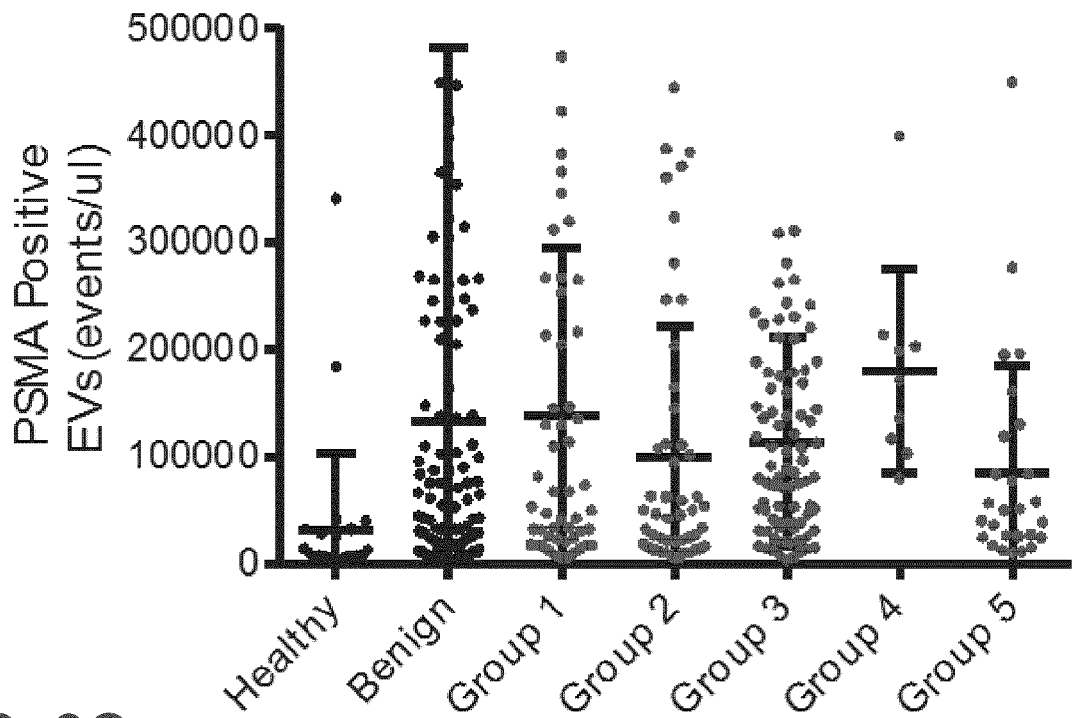
Figure 9C:
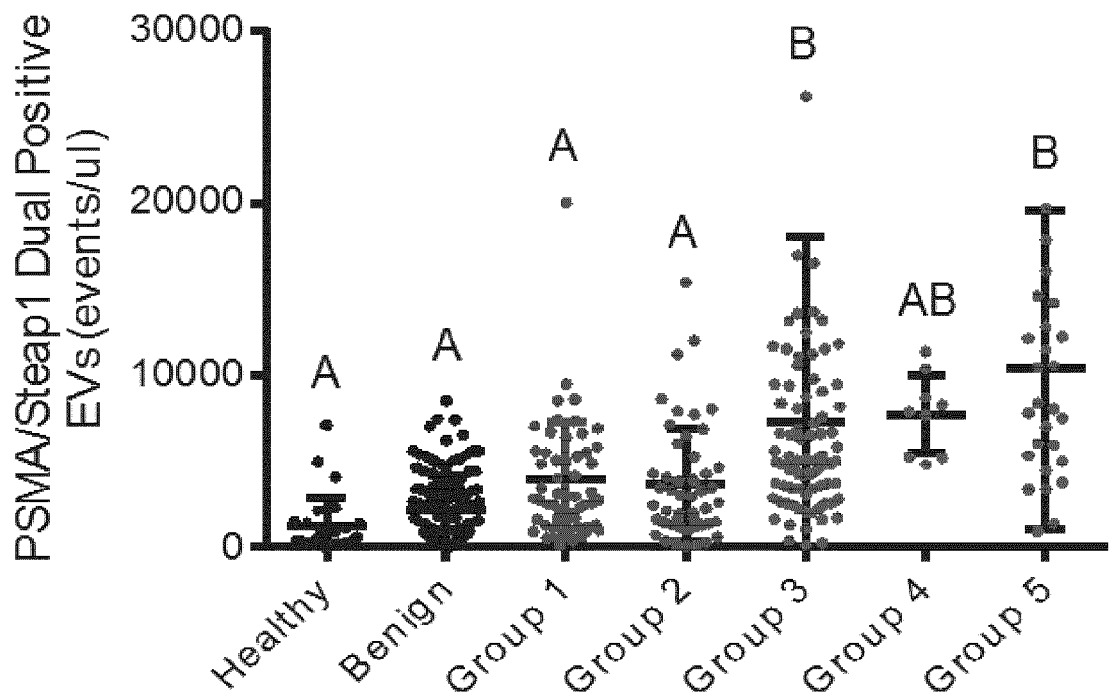
Figure 9D:
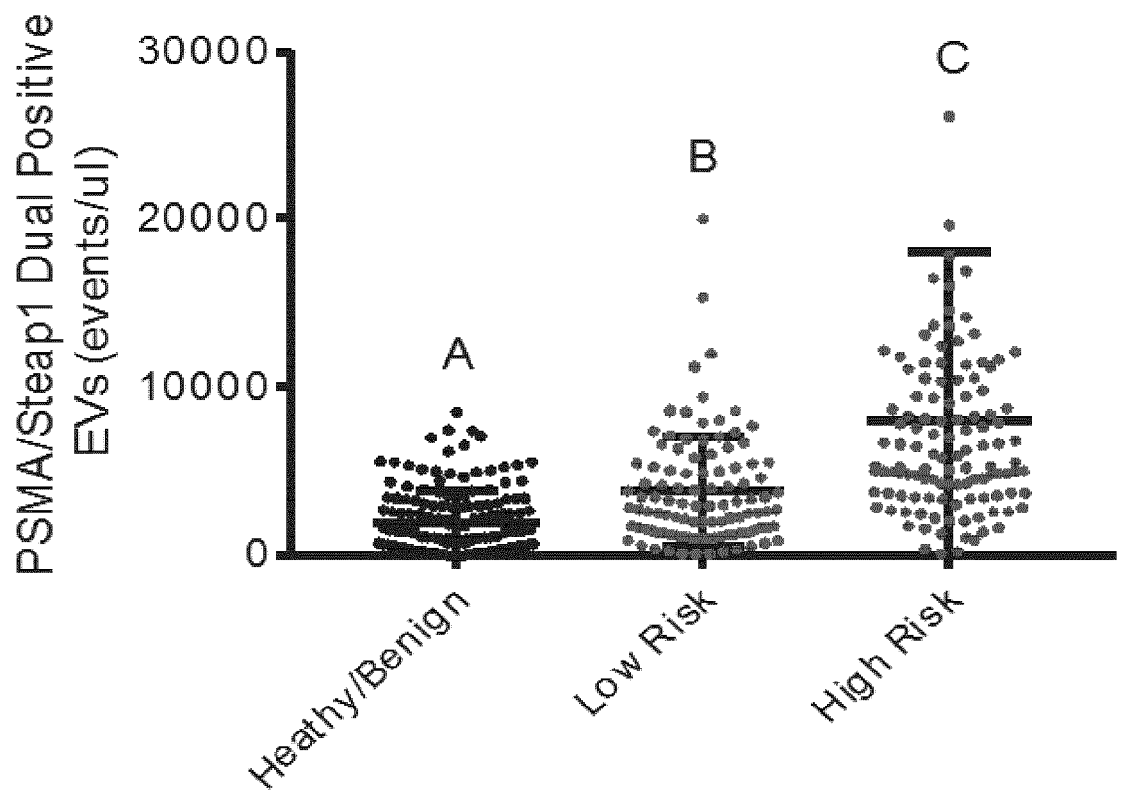

Example 11. STEAP1-PSMA Extracellular Vesicle Levels are Elevated in Prostate Cancer PSMA is expressed by cells of the prostate and elevated expression levels are associated with lethal prostate cancer (PMCID: PMC3893763). In addition, increased PSMA levels on circulating tumor cells correlates with increased Gleason grade (PMID: 27145459) and PSMA-positive extracellular vesicle levels are elevated in prostate cancer patients. PSMA-positive extracellular vesicles were readily detected by nanoscale flow cytometry (FIG. 9A, left column, and FIG. 9B). We then assessed if PSMA-positive extracellular vesicles were also positive for STEAP1. Dual-positive PSMA-STEAP1 extracellular vesicles were readily detected by nanoscale flow cytometry (FIG. 9B, right column, and FIG. 9C). Elevated levels were found in Groups 3-5 and Group 3 and 5 were found to have significantly higher levels of dual-positive extracellular vesicles compared to healthy, benign, and Groups 1-2 ($p \leq 0.01$) (FIG. 9C). Analysis of risk-stratified patients found elevated levels of dual-positive extracellular vesicles in high-risk individuals compared to healthy/benign and low risk ($p<0.0001$) (FIG. 9D). We also found that low-risk individuals had significantly increased dual-positive extracellular vesicles compared to healthy/benign (p=0.01) (FIG. 9D).

Figure 9E:
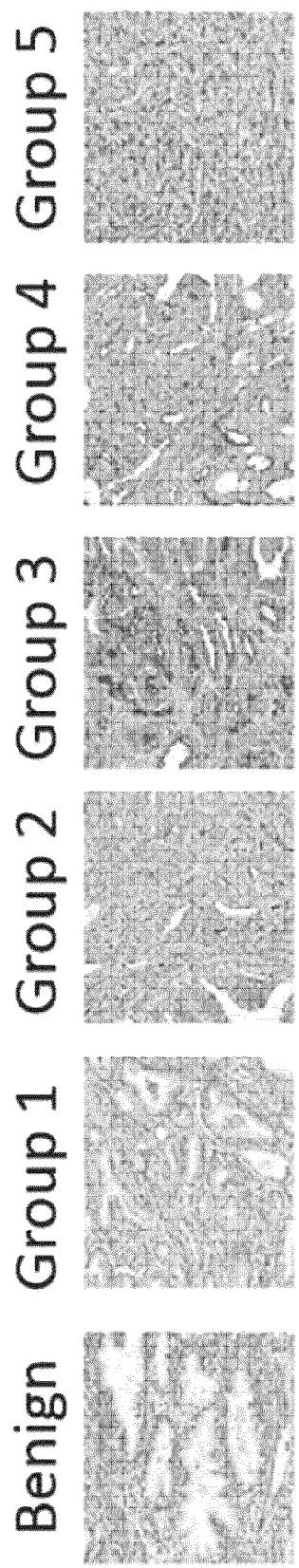
Figure 9F:
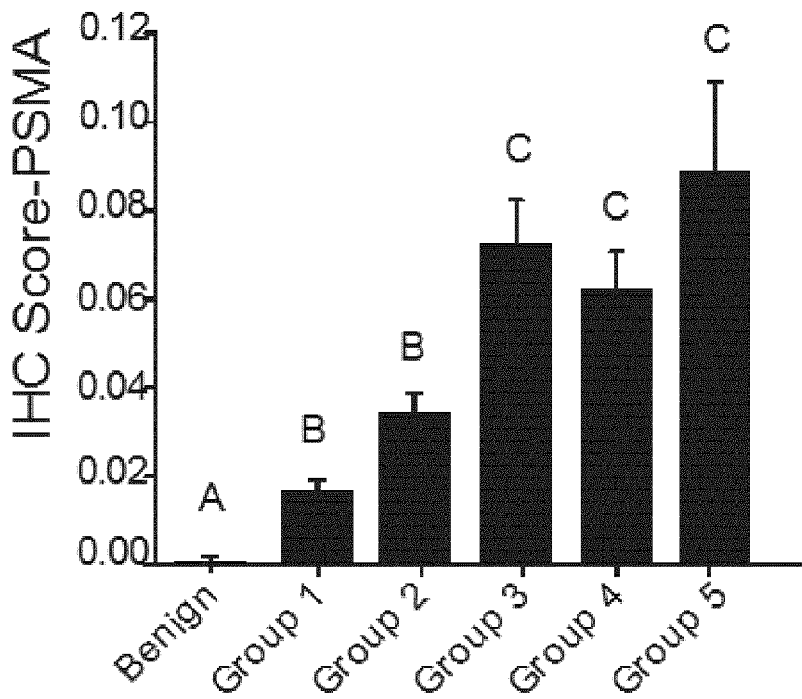
Figure 9G:
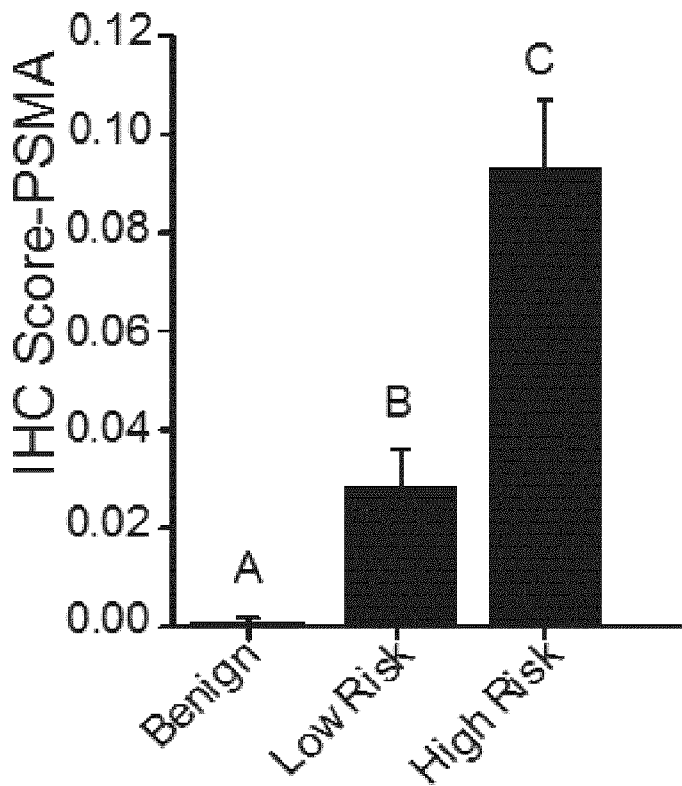

PSMA expression levels on tissue cores of the TMA were also assessed (FIG. 9E). PSMA was nearly undetectable on benign tissue samples and significantly increased in Groups 1-5 (p<0.0001). PSMA expression levels were significantly increased in Groups 3-5 compared to benign and Groups 1-2 (p<0.001) (FIG. 9F). Risk stratification of patients into low-risk and high-risk groups demonstrated that high-risk individuals had significantly higher PSMA expression levels compared to low-risk and benign (p<0.001), and low-risk had significantly higher PSMA levels than benign (p<0.001) (FIG. 9G). While tissue-PSMA expression was significantly elevated in Groups 3-5, extracellular vesicle-PSMA was not (FIGS. 9B and 9E), most likely due to PSMA-extracellular vesicles being shed from other tissues. However, dual-positive PSMA-STEAP1 extracellular vesicle levels were found to be identical to the results of tissue-PSMA expression levels, as both show significantly increased levels in high-risk compared to control (FIGS. 9C and 9E) suggesting that these extracellular vesicles are derived primarily from prostate tissue. PSMA expression in PCa is a known negative prognostic factor and Cox regression analysis of PSMA levels on our TMA further validates this as we found a significant reduction in recurrence free survival for individuals with high PSMA expression levels (p=0.001) (FIG. 9H).

Figure 10A:
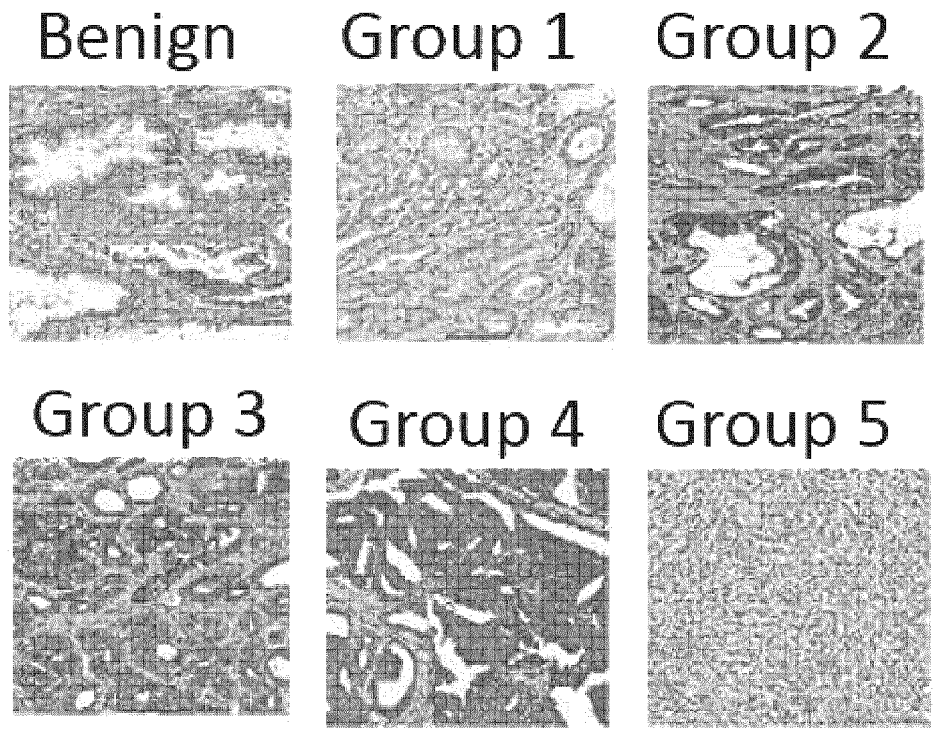
FIGS. 10A-10D are images and graphs demonstrating that polysialic acid is expressed in prostate cancer. Histochemical staining was performed for polysialic acid in benign and prostate cancer tissue cores (FIG. 10A). Representative images are shown. Analysis of 750 tissue cores was performed for polysialic acid expression in prostate cancer by Group score (FIG. 10B). Different letters represent statistical significance ($p<0.05$). Significantly higher expression were found in Groups 2, 3 and 4 compared to benign, Group 1 and 5 ($p<0.05$). Data is shown as mean±standard deviation. PolySia can identify men whose prostate cancer will eventually recur. With the clinical follow-up data accompanying the prostate cancer tissue specimens in the tissue microarray in FIG. 10A, tissues that had moderate and strong signal exhibited earlier times to cancer recurrence. * denotes 1.8% probability that survival curves are due to chance (Log Rank Mantel-Cox test). Number of patient deaths due to prostate cancer was correlated to polysialic acid staining (FIG. 10D).
Figure 10B:
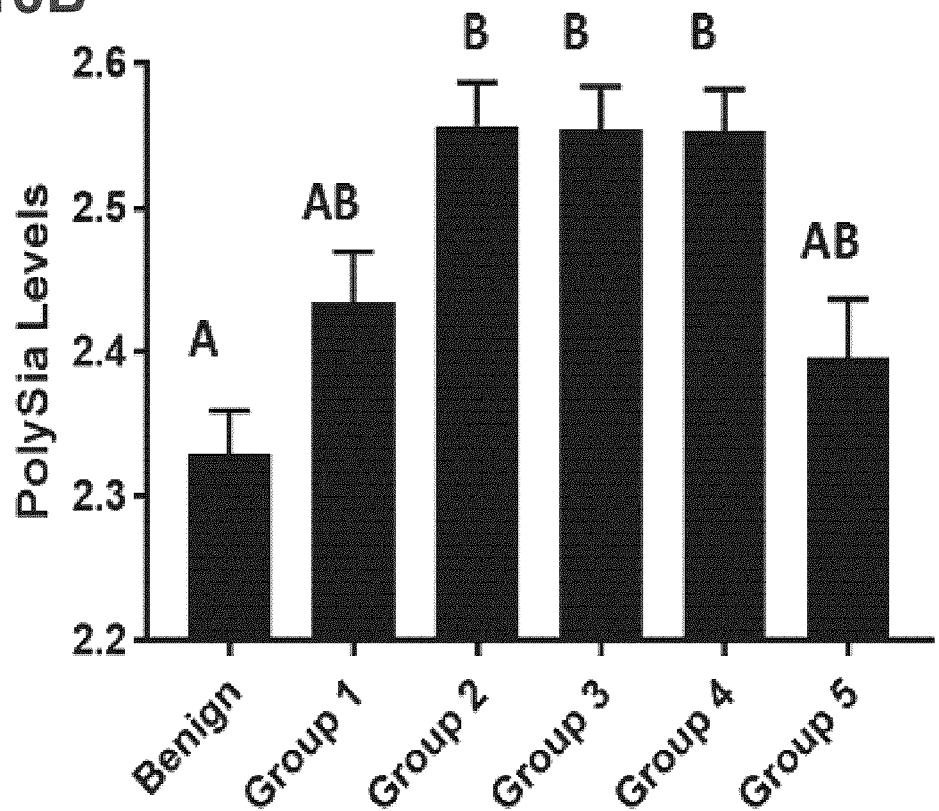
Figure 10C:
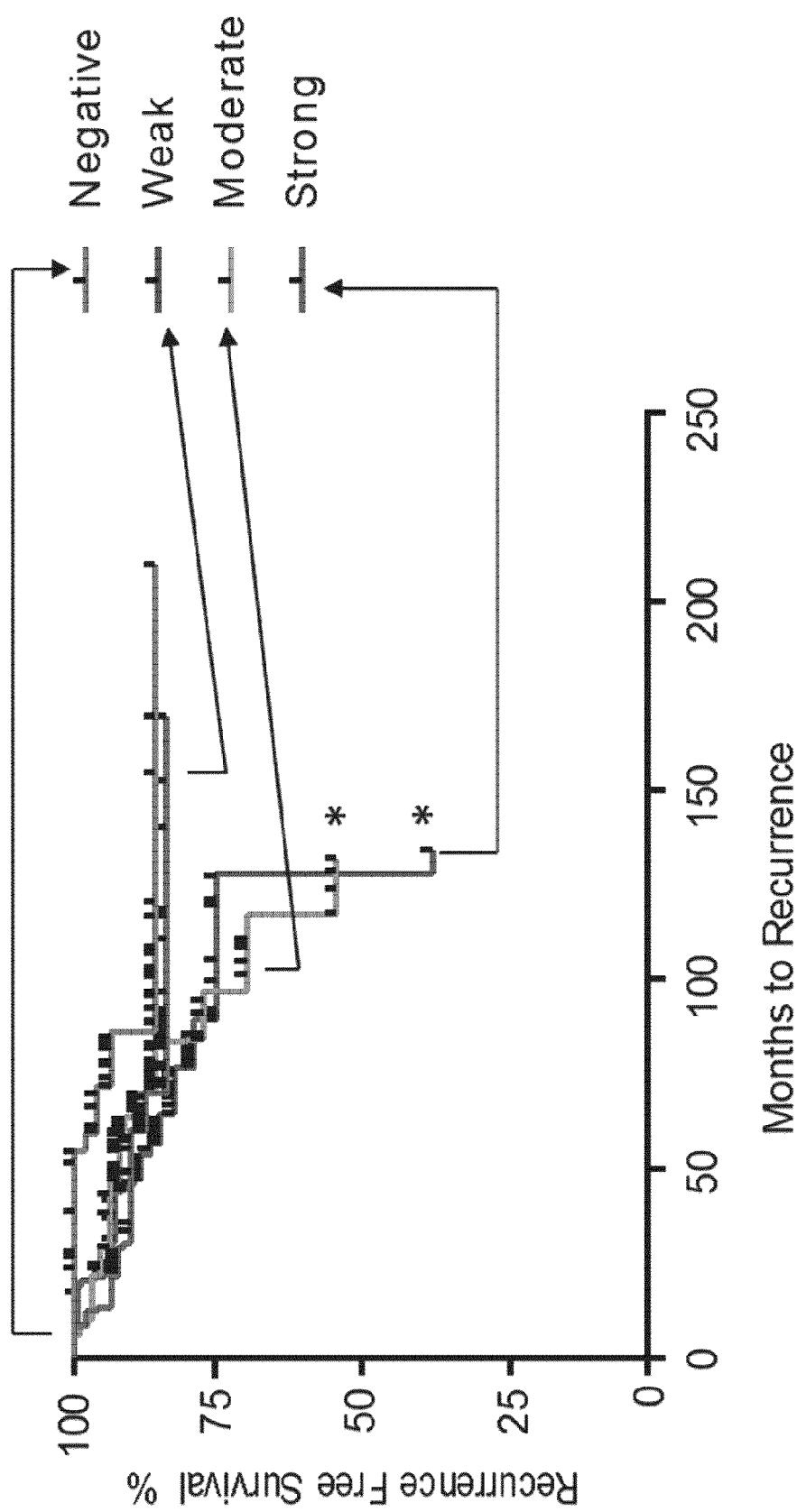
Figure 10D:
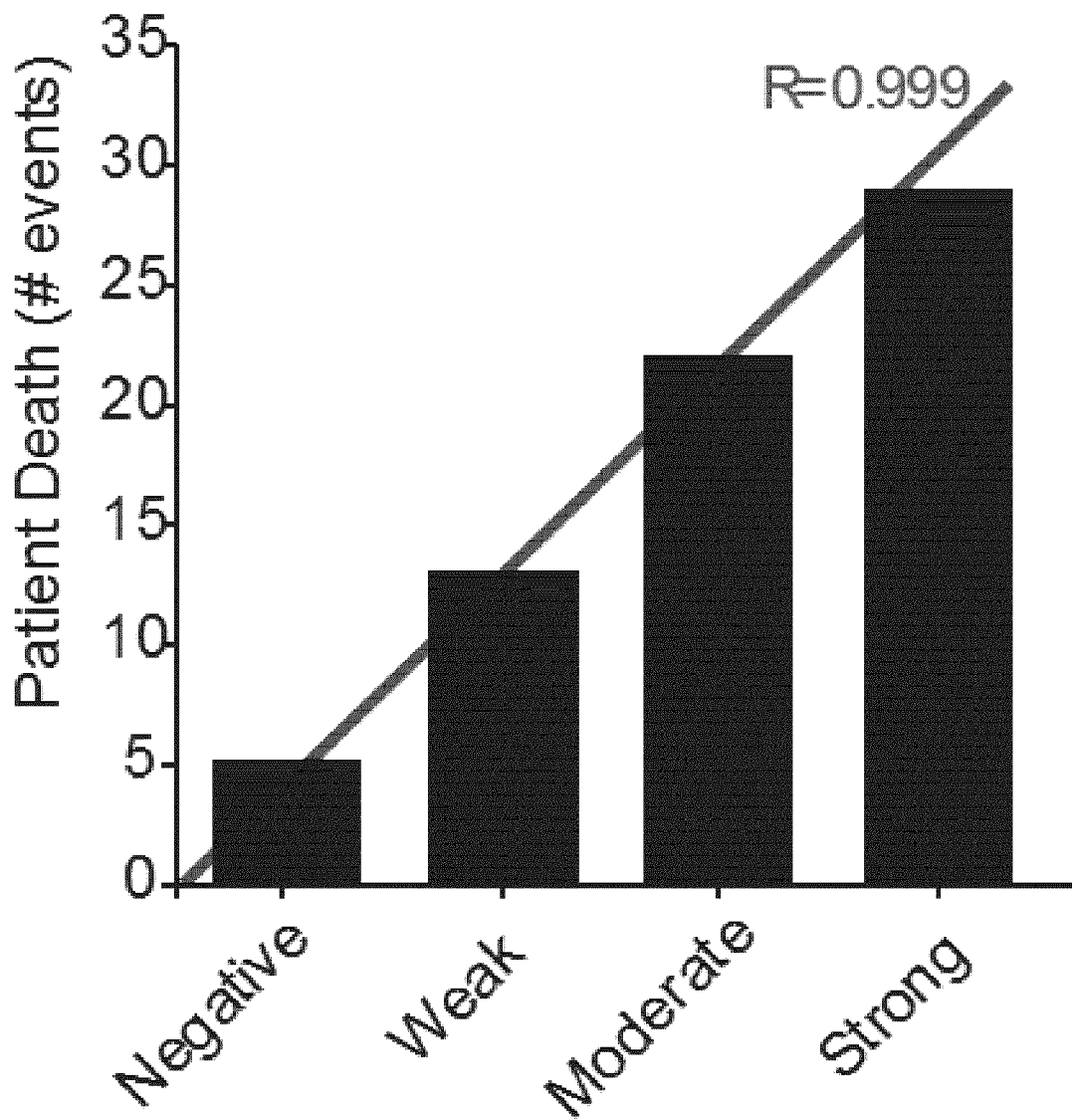
Figure 19:
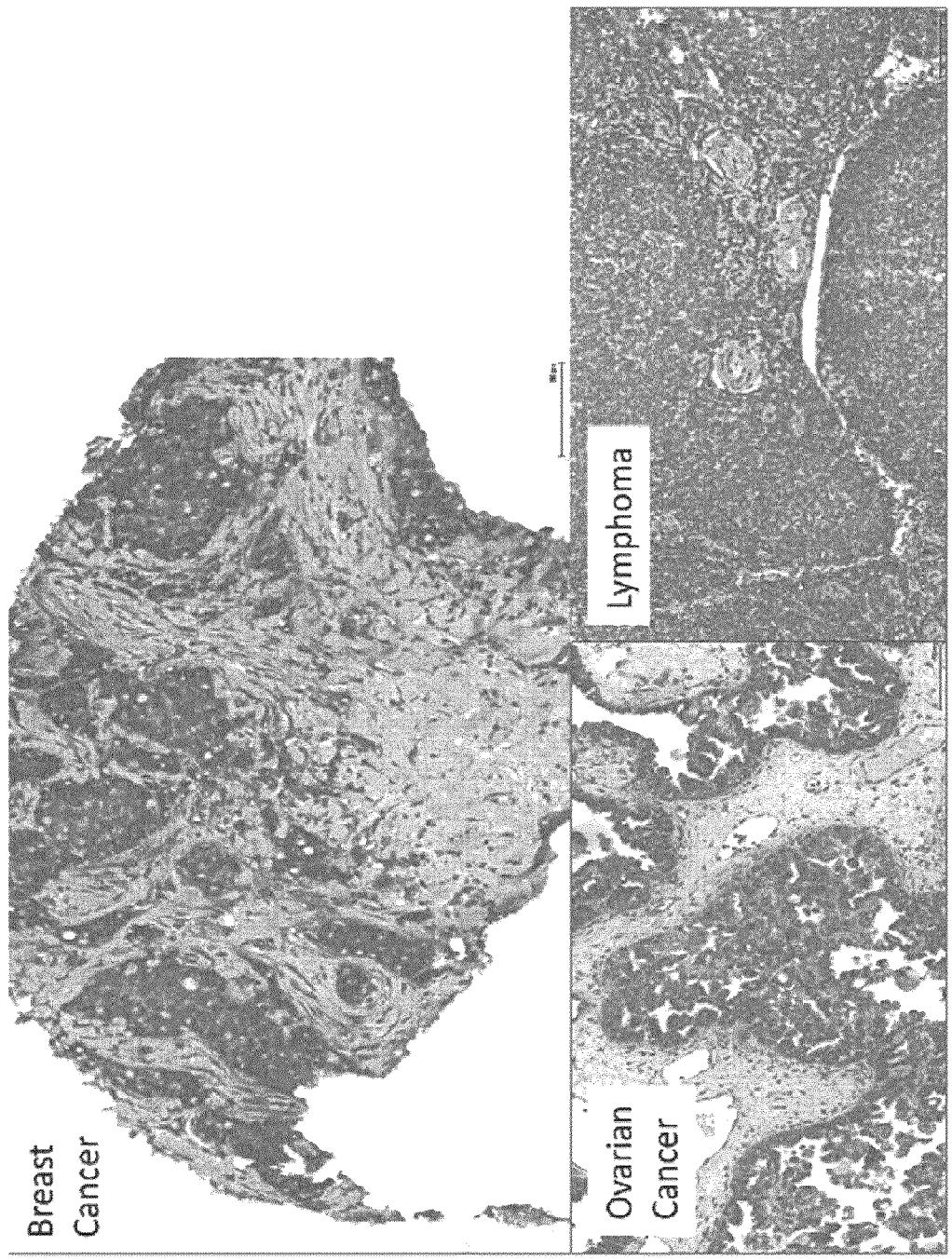
FIG. 19 is a series of images depicting that polySia is cytoplasmically expressed in other types of cancer. Cytoplasmic expression was also observed in breast cancer tissue biopsies, ovarian cancer tissue and lymphoma tissue. Immunostaining performed with anti-polySia specific antibody.

Example 12. Polysialic Acid is Present on Prostate Tumor Cores and Correlates with Aggressive Disease Aberrant expression of polySia has been documented for multiple cancers such as neuroblastoma, non- and small cell lung carcinoma, and leukemia, and is associated with poor patient outcome. To explore if polySia is present on prostate tumor cells we stained and analyzed our TMA for polySia expression. We found that tumor cores did express polySia and that levels of polySia were increased in prostate cancer with a significant increase in expression levels in Groups 2-4 compared to benign (p<0.01) (FIGS. 10A-10B). To determine if elevated polySia expression increased an individual's risk for disease progression, progression free survival outcomes were evaluated. Progression free survival was significantly reduced in patients with moderate and strong polySia staining (p<0.001) (FIG. 10C). In addition, there was a high correlation between the number of deaths and polySia expression levels (correlation coefficient=0.99893) (FIG. 10D). Taken together, these results demonstrate that polySia is expressed in prostate cancer and elevated levels are associated with an aggressive disease and poor patient outcome. We also performed polySia staining on tissue samples from other types of cancer, and observed polySia in tissue from breast cancer, ovarian cancer, and lymphoma (FIG. 19).

Figure 4A:
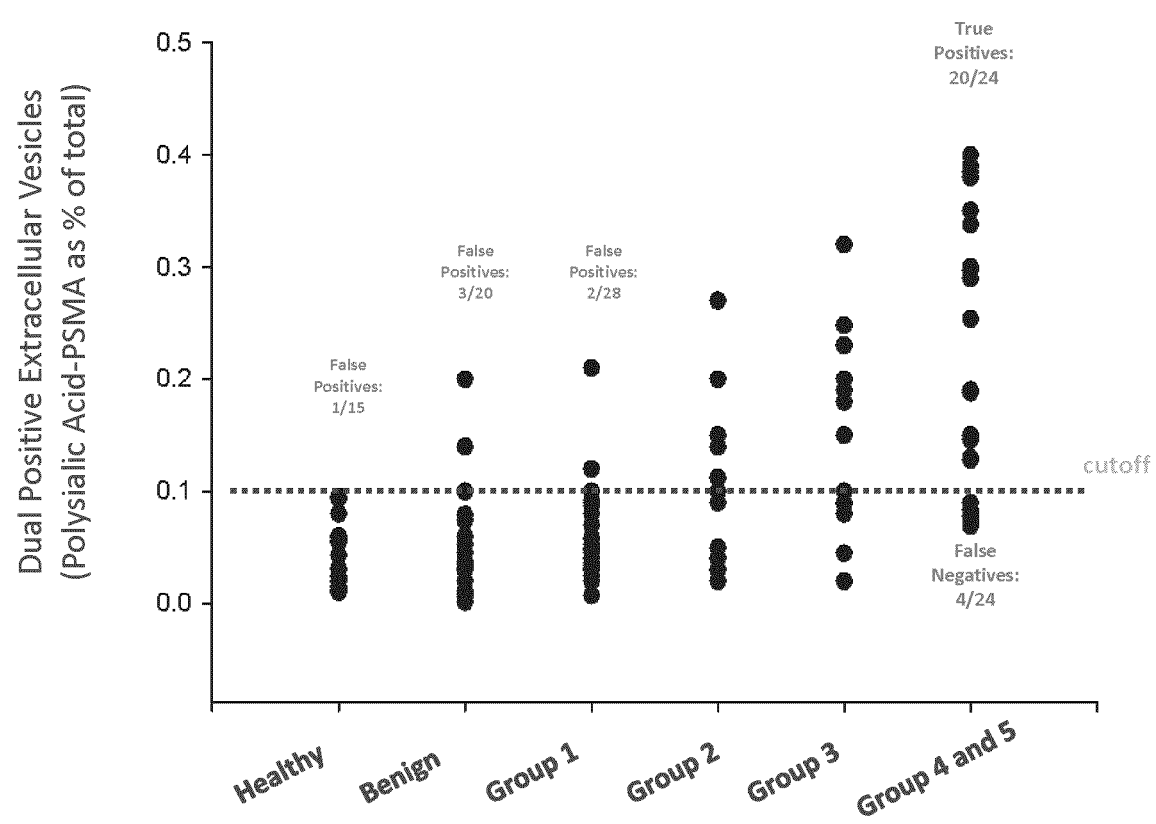
Figure 11A:
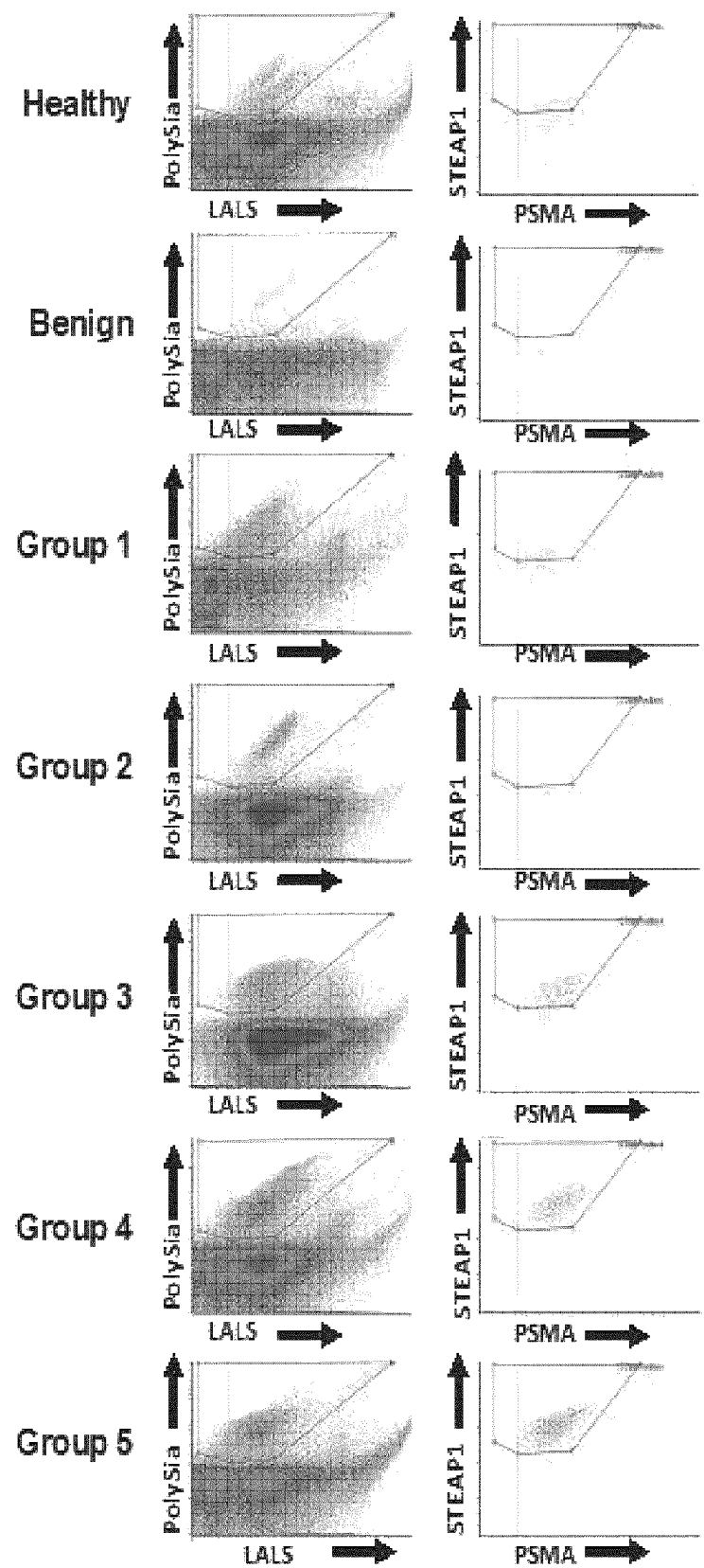
FIGS. 11A-11E are a series of graphs demonstrating that polysialic acid-STEAP1-PSMA positive extracellular vesicle levels are elevated in non-indolent prostate cancer. Polysialic acid extracellular vesicles, left column, and triple-positive polysialic acid-PSMA-STEAP1 extracellular vesicles, right column, were detected using nanoscale flow cytometry (FIG. 11A). Bivariate plots from patient plasma samples are represented. The outlined area in the graphs on the left was manually selected to exclude background noise and non-specific signal as determined by IgG controls and represents extracellular vesicles positive for polysialic acid, left column, and polysialic acid-PSMA-STEAP1, right column. Polysialic acid-extracellular vesicle levels (FIG. 11B) and polysialic acid-PSMA-STEAP1 extracellular vesicle levels (FIG. 11C) in plasma samples were analyzed by nanoscale flow cytometry. Three hundred seventy eight plasma samples consisting of 27 healthy, 128 benign, 53 Group 1, 51 Group 2, 83 Group 3, 9 Group 4, and 27 Group 5 plasma were analyzed and the distribution is represented. Significantly higher levels were found in Group 5, Group 4 and Group 3 compared to healthy, benign, Group 1, and Group 2 ($p<0.002$). Analysis of polysialic acid-STEAP1-PSMA extracellular vesicle levels was performed based on patient risk-stratification (FIG. 11D). Different numbers represent statistical significance ($p<0.0001$). Data is shown as mean±standard deviation. A triple-positive extracellular vesicle test detects non-indolent prostate cancer (FIG. 11E). To determine how well triple-positive extracellular vesicle levels predict high-risk prostate cancer, an area under receiver operating characteristic curve was generated (AUC, FIG. 11E). The curve represents the true-positive rate (sensitivity) and false positive rate (100%-specificity) demonstrating the performance characteristics for a triple positive extracellular vesicle test to report non-indolent disease. A triple-positive extracellular vesicle test for prostate cancer detection generated an AUC=0.854 (Confidence Interval: 0.812, 0.894). Under the same conditions, Prostate-specific antigen testing generated an AUC=0.694. The diagonal line represents the reference line, AUC=0.5.
Figure 11B:
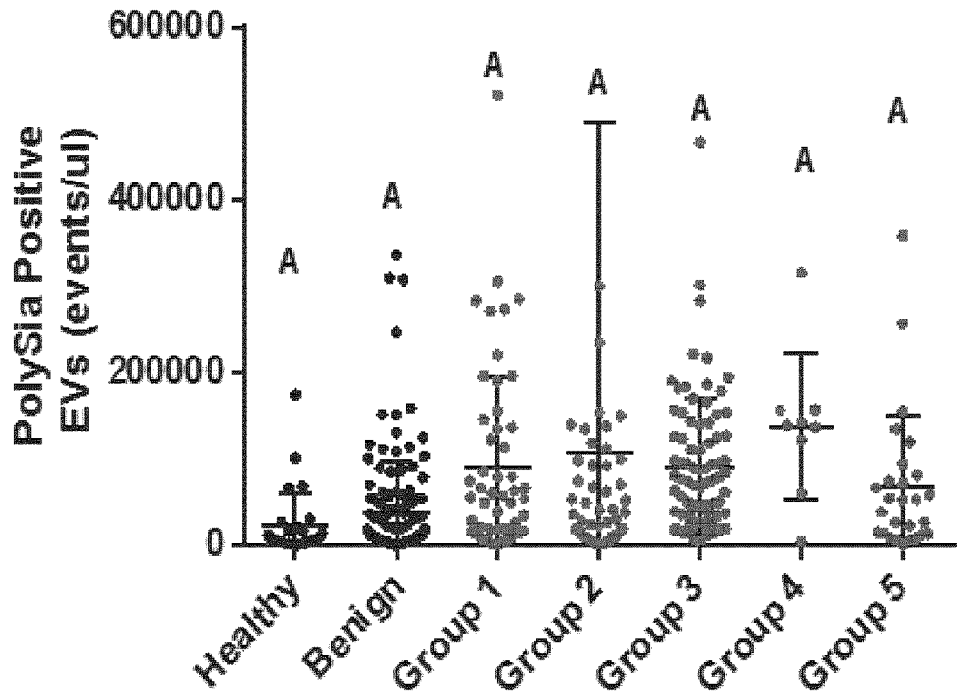
Figure 11C:
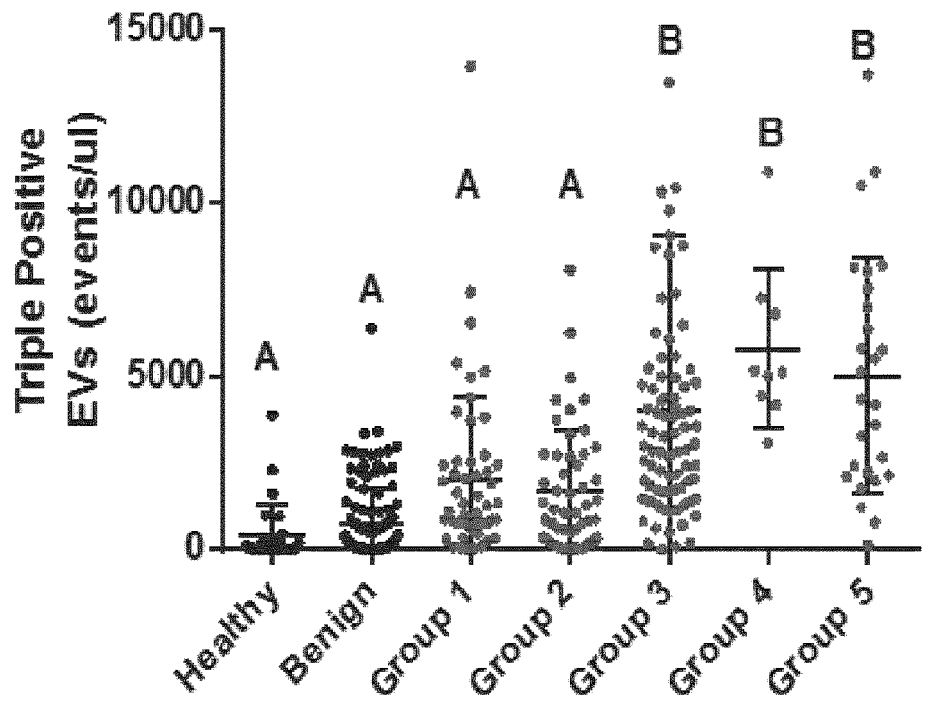
Figure 11D:
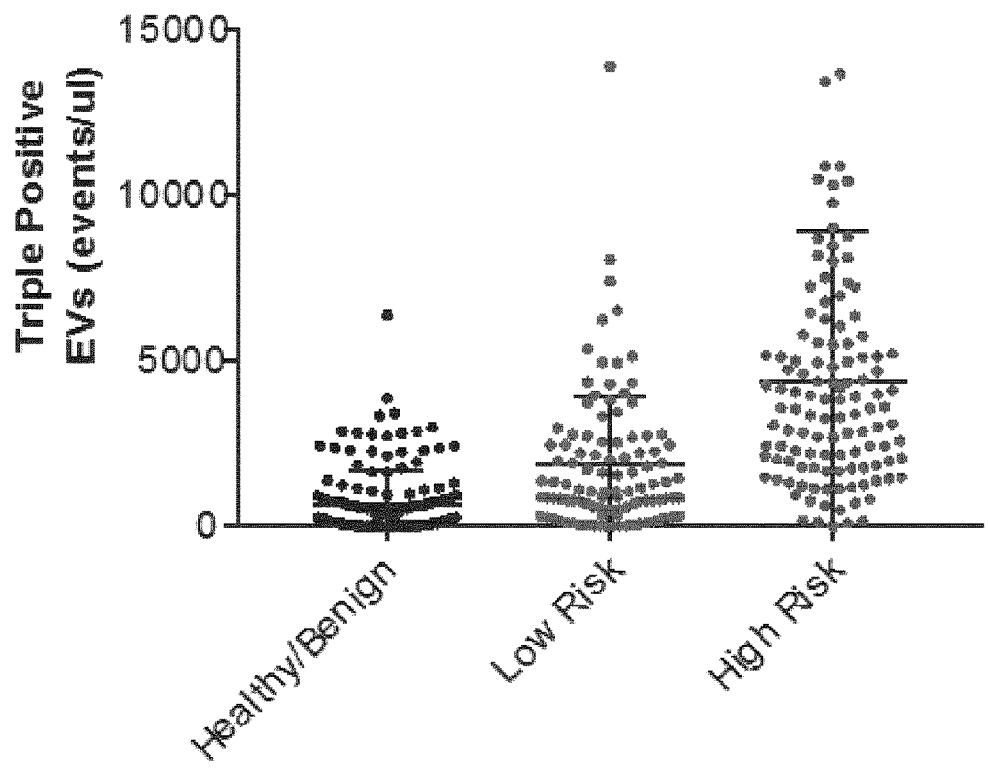
Figure 11E:
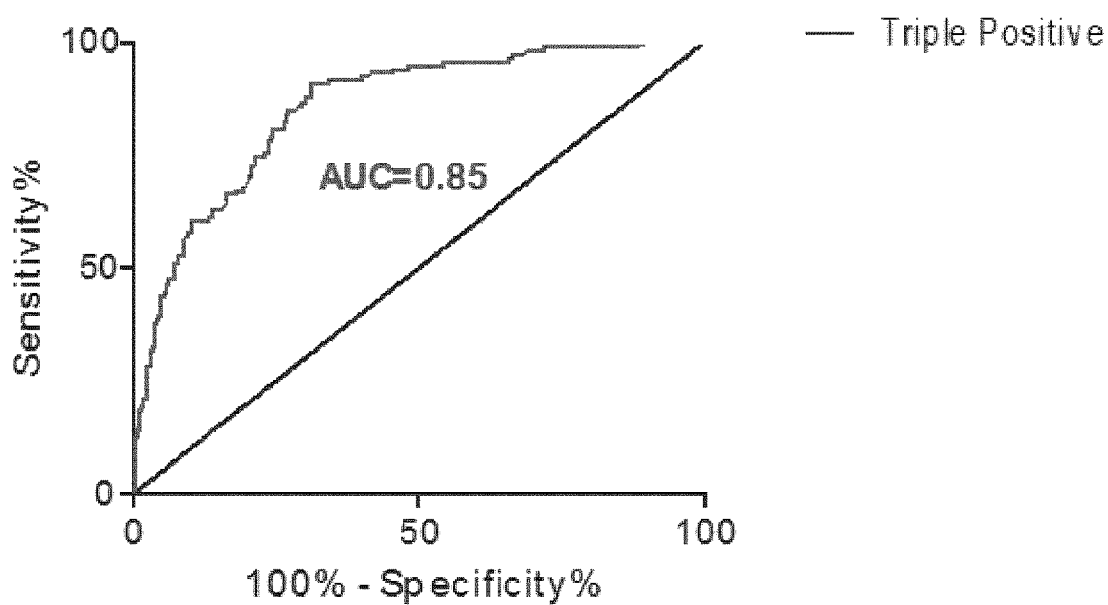
Figure 12:
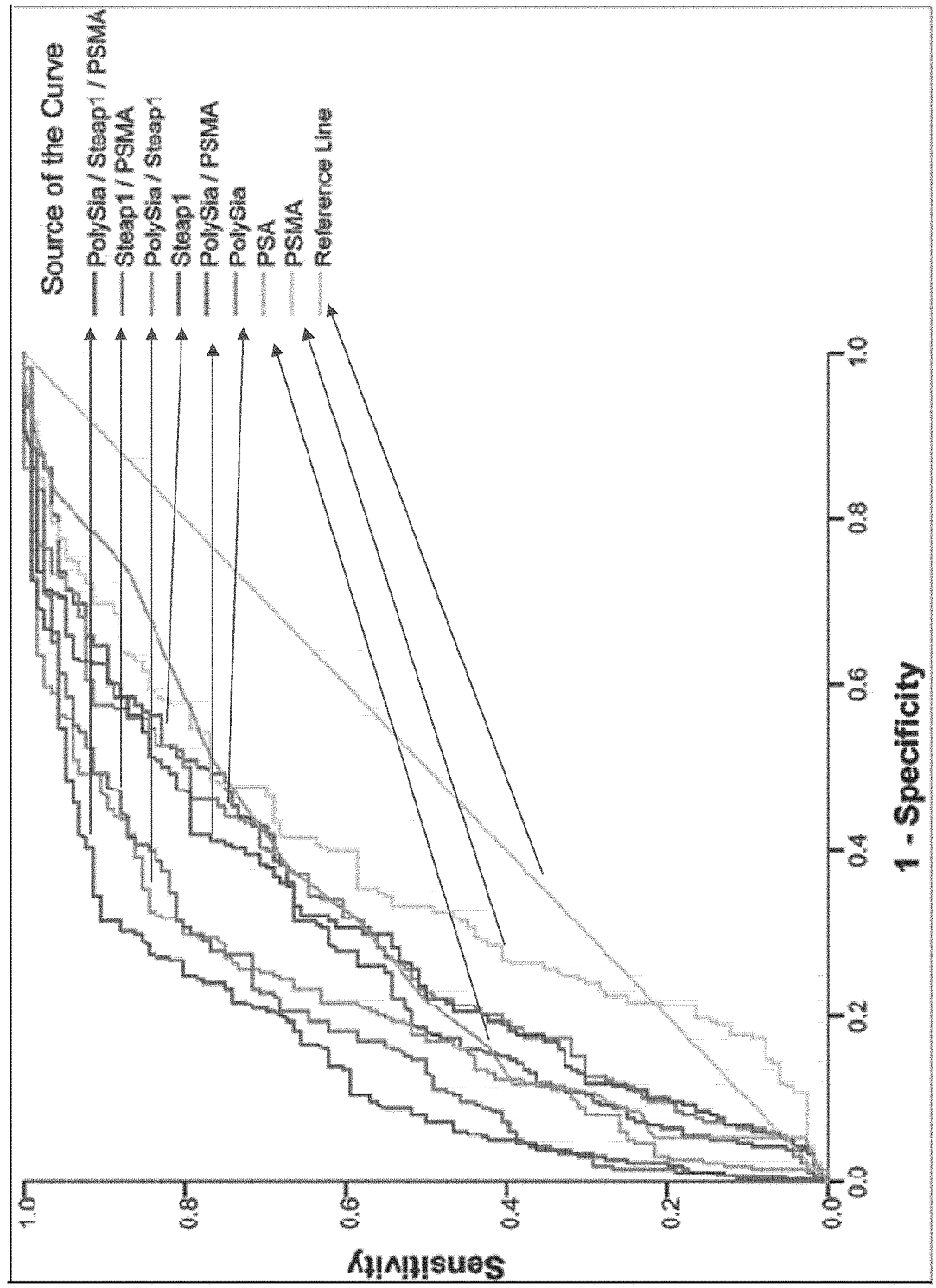
FIG. 12 is a graph depicting the Area Under the Curves (AUCs) generated from all possible combinations of bio-markers showing that triple-positive events generate better test parameters than all other possible combinations. PolySia/PSMA/STEAP1 AUC=0.854 CI: 0.812, 0.894. STEAP1/PSMA AUC=0.812, CI: 0.766:0.858. PolySia/STEAP1 AUC=0.797, CI: 0.752, 0.842. PolySia/PSMA AUC=0.711, CI: 0.659:0.764. PolySia AUC=0.702, CI: 0.648, 0.755. PSMA=0.622 CI: 0.566:0.679. STEAP1 AUC=0.716, CI: 0.662:0.771.

Example 13. Polysialic Acid on Prostate-Derived Extracellular Vesicles Risk Stratifies PCa Patients PolySia extracellular vesicles were readily detectable by nanoscale flow cytometry (FIG. 11A, left column). Analysis of polySia extracellular vesicles revealed an increase in the mean number of polySia-extracellular vesicles in prostate cancer patient plasma (healthy: 22356; Benign: 38388; Group 1-5: 107969, 90504, 137230, 67524); however, this was not statistically significant between Groups (FIGS. 11A-11B). To determine if these polySia extracellular vesicles were positive for STEAP1 and PSMA, we analyzed polySia events for dual staining with STEAP1 and PSMA (FIG. 11A, right column). PolySia-PSMA-STEAP1 extracellular vesicles were detected by nanoscale flow cytometry and levels of triple positive particles in patient plasma were assessed. Triple positive extracellular vesicle events were found to be significantly elevated in Groups 3-5 compared to healthy (p<0.0001), benign (p<0.0001), and Groups 1-2 (p<0.001) (FIG. 11C). Analysis of risk-stratified patients found elevated levels of triple-positive extracellular vesicles in high-risk individuals compared to healthy/benign and low risk (p<0.0001) (FIG. 11D). We also found that low-risk individuals had significantly increased triple-positive extracellular vesicles compared to healthy/benign (p=0.002) (FIG. 11D). Considering that polySia-STEAP1-PSMA triple positive events were statistically different between high risk Groups 3-5 compared to low risk Groups 1-2, benign, and healthy, ROC analysis was further conducted to examine the diagnostic ability of triple positive extracellular vesicle test to predict PCa. ROC analysis resulted in an Area Under the Curve (AUC) of 0.85 (p<0.0001) and a 95% Confidence interval of 0.811 to 0.891 (FIG. 11E). Based on analysis of triple positive event rates and their corresponding false discover rate (FDR), the cutoff value of for healthy versus PCa was set at 2000 events/µl. With a cutoff value of 2000 events/µl, a triple positive extracellular vesicle test had a false positive prostate cancer detection rate of 3.7% for healthy, and 7.8% for benign, and prostate cancer detection rates of 24.5% for Group 1, 34.4% for Group 2, 64.8% for Group 3, 100% for Group 4 and 85.7% for Group 5. In terms of size, we found that polysia+ve PCEVs are a very discrete subpopulation ranging between 250-480 nm in diameter. We also generated AUCs from all possible combinations of biomarkers showing that triple-positive events generate better test parameters than all other possible combinations. PolySia/PSMA/STEAP1 AUC=0.854 CI: 0.812, 0.894; STEAP1/PSMA AUC=0.812, CI: 0.766:0.858; PolySia/STEAP1 AUC=0.797, CI: 0.752, 0.842; PolySia/PSMA AUC=0.711, CI: 0.659:0.764 (measurement of dual-positive macrovesicles also shown in FIGS. 4A-4B); PolySia AUC=0.702, CI: 0.648, 0.755; PSMA=0.622 CI: 0.566: 0.679; STEAP1 AUC=0.716, CI: 0.662:0.771 (FIG. 12).

Figure 13A:
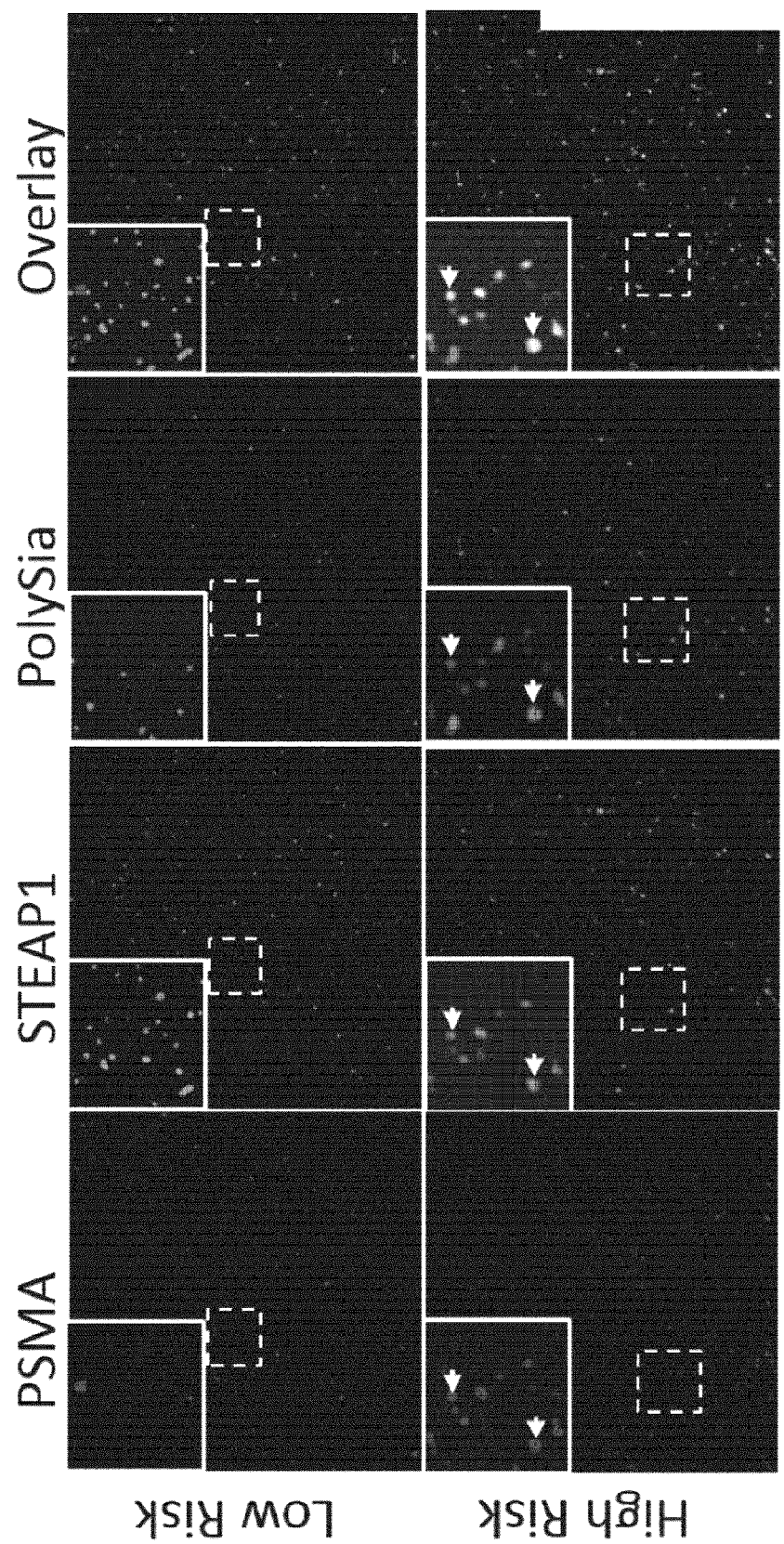
FIGS. 13A and 13B are fluorescent images from super-resolution confocal microscopy of extracellular vesicles. Patient plasmas were immunostained with Alexa594-PSMA, Alexa647-STEAP1 and FITC-polysialic acid. Extracellular vesicles were dried on coverslips and imaged using super-resolution fluorescence microscopy. Wide field imaging was used to visualize particles and staining patterns of PSMA, STEAP1, and polysialic acid in low risk and high risk patient plasmas (FIG. 13A). Arrows in high risk images point to colocalization of all three markers. Zooms of single particles from FIG. 13A (arrows) show clusters of extracellular vesicles as represented by a single X-Y slice (top row) and a z-stack volume (bottom row, FIG. 13B). Scale bar=1 µm.
Figure 13B:
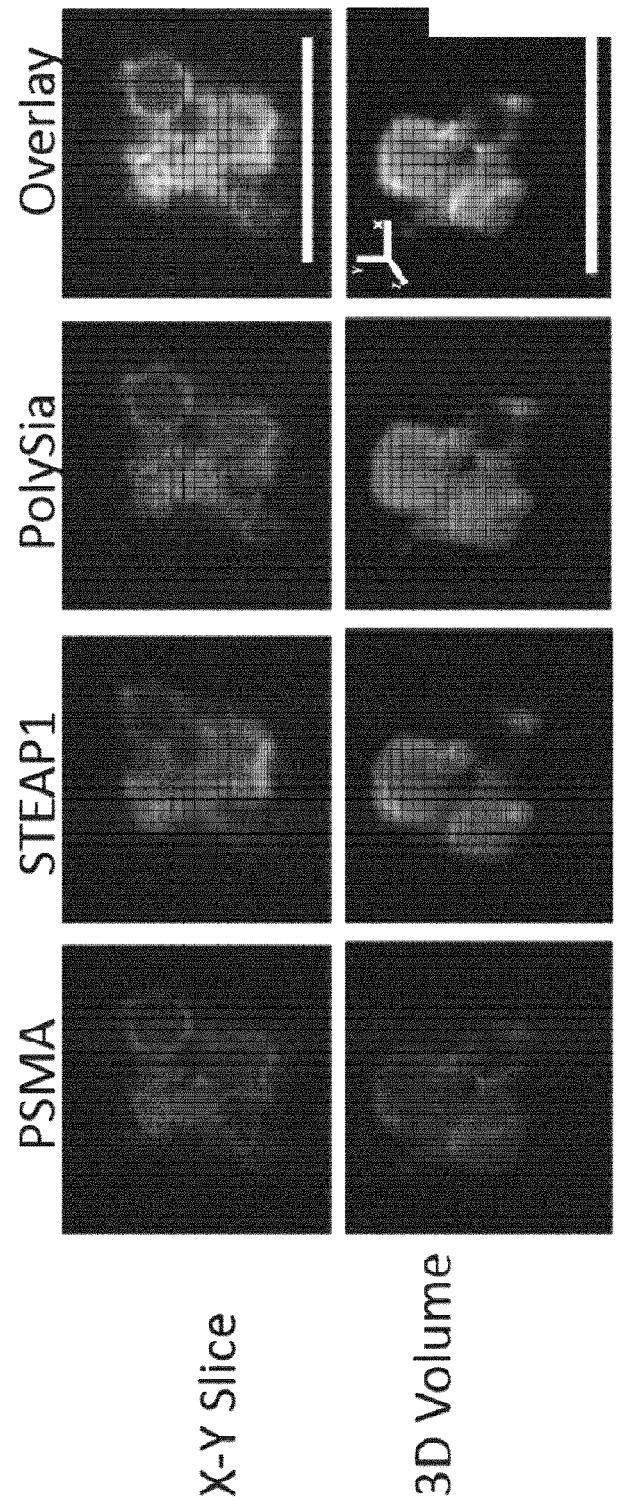

To visualize extracellular vesicles present in patient plasma, super resolved fluorescence microscopy was performed. Extracellular vesicles in low-risk and high-risk patient plasmas were stained for PSMA, STEAP1 and polySia (FIG. 13). Small particles were found to be positive for PSMA, STEAP1 and polySia, and particles positive for all three markers were readily detectable in high-risk samples (FIG. 13A). High resolution zooms on single particles showed extracellular vesicles with membranous staining for PSMA, STEAP1 and polySia (FIG. 13B, top row). Three dimensional reconstruction from total volume is also shown (FIG. 13B, bottom row).

Figure 14A:
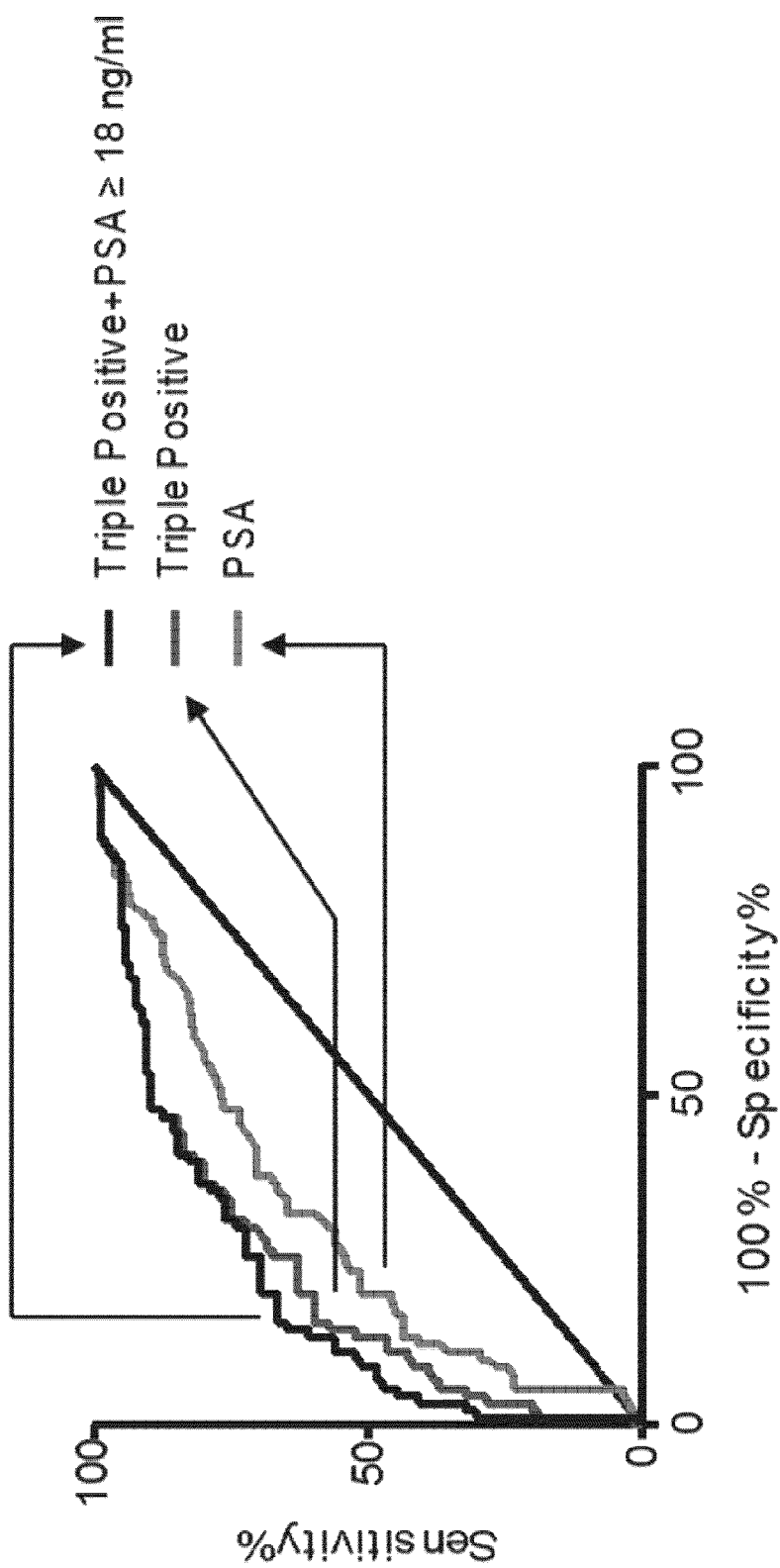

Example 14. A Triple-Positive EV Test Outperforms Prostate Specific Antigen Testing Analysis of PSA levels is a common method used in the diagnosis of prostate cancer; however, it has a high rate of false discovery and detection of indolent disease, Groups 1 and 2, leading to a significant level of overtreatment in prostate cancer. To compare the test parameters of a PSA test or Triple-positive extracellular vesicle test to risk-stratify between Groups 1-2 and Groups 3-5, we generated an AUC using only the patients who had a recorded PSA score (FIG. 14A). PSA testing generated an AUC of 0.69 (95% CI: 0.61, 0.76) and a Triple-positive test generated an AUC of 0.78 (95% CI: 0.72, 0.85). Based on our PSA AUC, we found that while PSA testing is highly sensitive at detecting prostate cancer at 4 ng/ml (Sensitivity=86.8%) it was not specific (Specificity=35.3%); however the specificity significantly improves if PSA levels are ≥18 ng/ml (Specificity=96.5%), but sensitive is lost (Sensitivity=10.5%). To incorporate the high level of PSA Specificity at 18 ng/ml we generated an AUC combining our Triple-positive test with PSA≥18 ng/ml. The test parameters were set to give a diagnosis of prostate cancer if Triple-positive levels were ≥2000 event/µl or PSA was ≥18 ng/ml. The AUC for a Triple-positive/PSA≥18 ng/ml was 0.80 (95% CI 0.75 to 0.87). A direct comparison of the false discovery rate (FDR) and true discovery rate (TDR) for these testing platforms found PSA testing at 24 ng/ml had a 77.5% FDR of cancer in low-risk groups and missed cancer in 6.3% of high-risk patients (FIG. 14B). A triple-positive extracellular vesicle test at ≥2000 events/µl had a 28% FDR of cancer and missed cancer in 17.3% of high-risk patients. Combination of PSA≥18 ng/ml and triple-positive ≥2000 events/µl had a 28% FDR of cancer and missed cancer in 12.6% of high-risk patients.

Figure 15A:
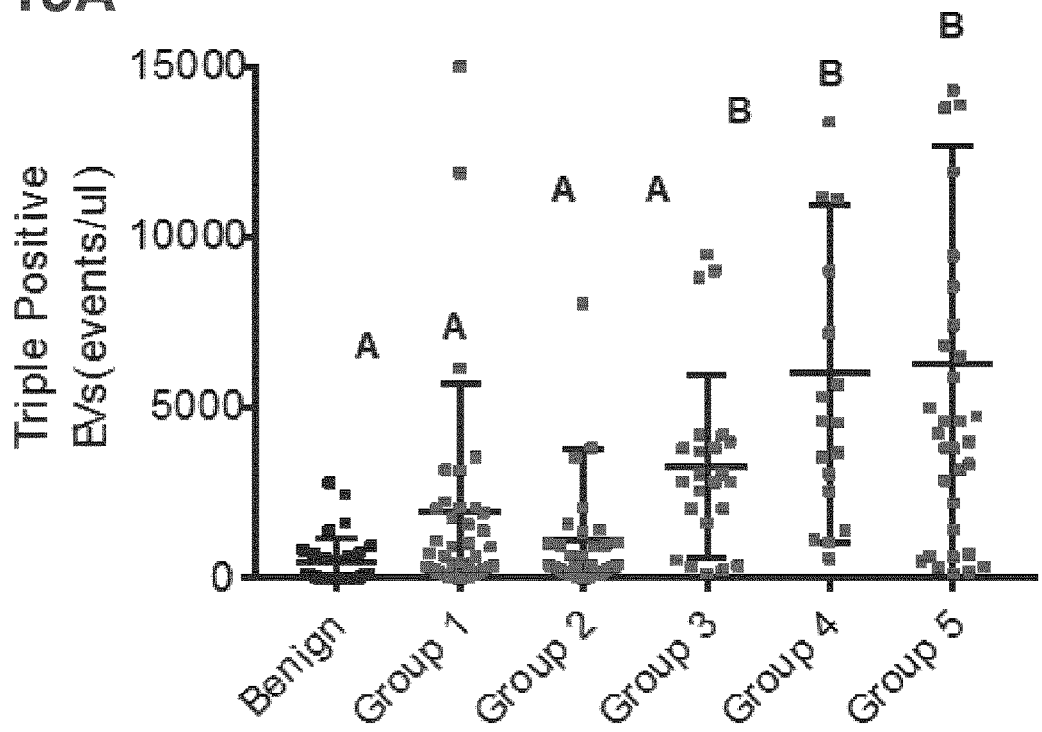
FIGS. 15A-15C are a series of graphs depicting a validation patient cohort for determining the test characteristic of a triple positive extracellular vesicle test to diagnose non-indolent prostate cancer. Polysialic acid-PSMA-STEAP1 extracellular vesicle levels were measured in a validation patient cohort containing 195 plasma samples from benign and prostate cancer patients. Analysis of triple-positive levels was performed based on Group score (FIG. 15A) and risk stratification (FIG. 15B). Evaluation of a triple-positive extracellular vesicle test was performed to predict high-risk prostate cancer using the area under receiver operating characteristic curve (AUC=0.81, CI: 0.74, 0.87, FIG. 15C). The curve represents the performance characteristics for a triple positive extracellular vesicle test to report non-indolent disease. The diagonal line represents the reference line, AUC=0.5. Under the same conditions, Prostate-specific antigen testing generated an AUC=0.68. Different numbers represent statistical significance ($p<0.05$). Data is shown as mean±standard deviation.
Figure 15B:
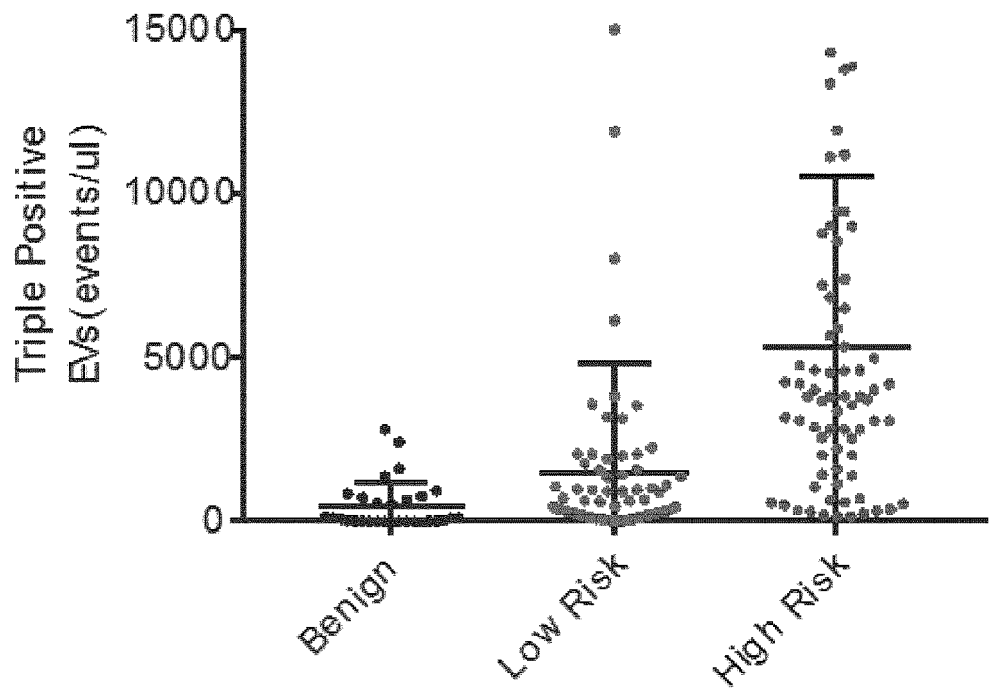
Figure 15C:
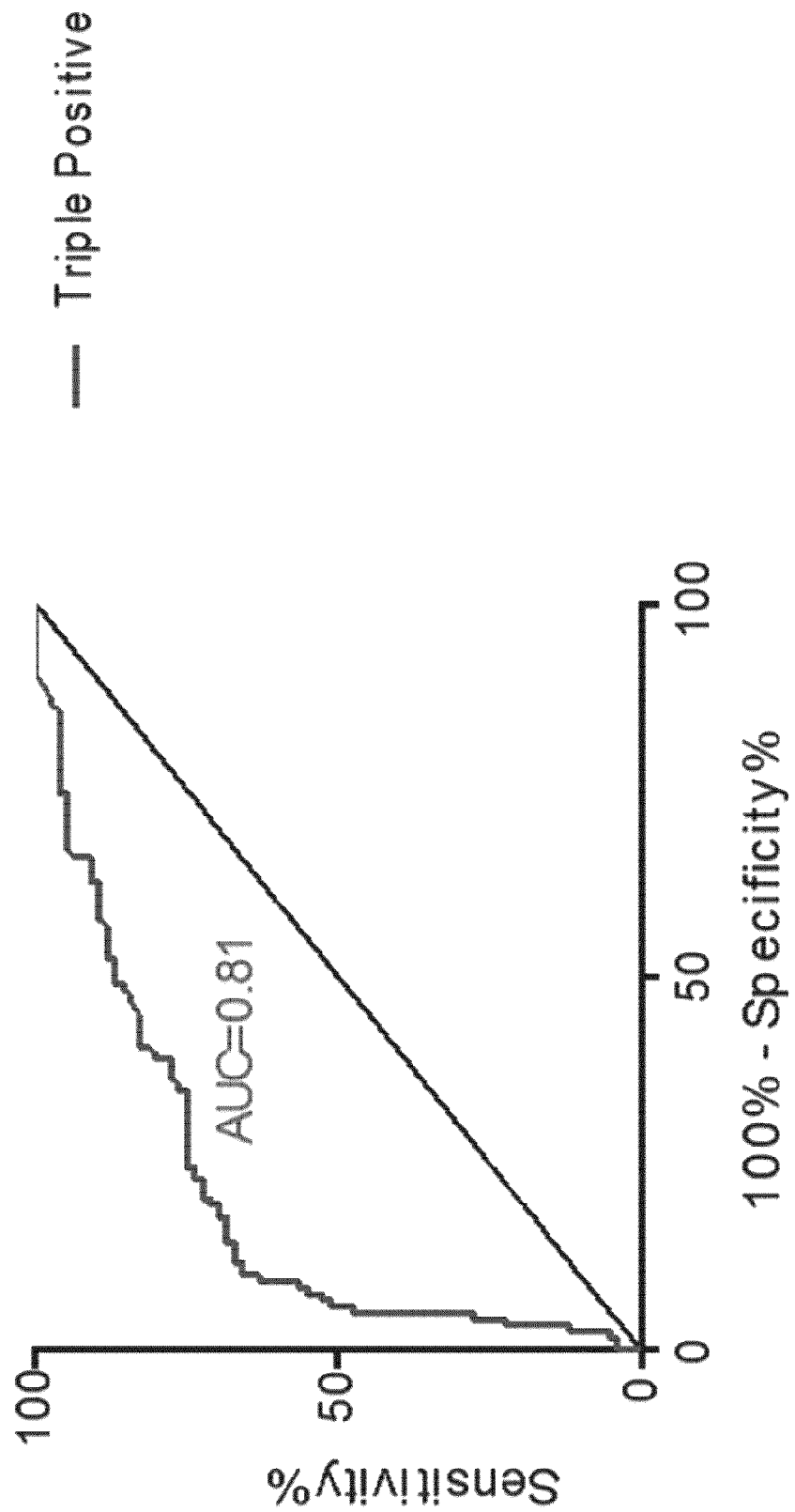

Example 15. Validation of a PolySia-STEAP1-PSMA EV Test for Detecting Aggressive Prostate Cancer To validate a polySia-STEAP1-PSMA extracellular vesicle detection test, a validation cohort was analyzed. This cohort consisted of 30 benign, 45 Group 1, 43 Group 2, 20 Group 3, 20 Group 4, and 37 Group 5 plasmas. Analysis of triple positive polySia-STEAP1-PSMA extracellular vesicle events demonstrated a significant increase in triple-positive levels for Group 3, 4 and 5 compared to benign (p<0.0001) and Group 1 and 2 (p<0.002) (FIG. 15A). Analysis of risk-stratified patients found significantly elevated triple-positive levels in high risk patients compared to low risk patients (p<0.0001), and low-risk individuals had significantly higher levels than benign (p=0.002) (FIG. 15B). ROC analysis of a test capable of detecting Groups 3-5 versus benign/Groups 1-2, generated an AUC of 0.81 (p<0.001) and a 95% Confidence interval of 0.74 to 0.88 (FIG. 15C). Using the cutoff value determined through FDR analysis in the discovery cohort, 2000 events/µl, a triple-positive extracellular vesicle test had a cancer detection rate of 3.3% for benign, 15.5% for Group 1, 11.6% for Group 2, 78.9% for Group 3, 70% for Group 4 and 72.9% for Group 5.

Figure 16A:
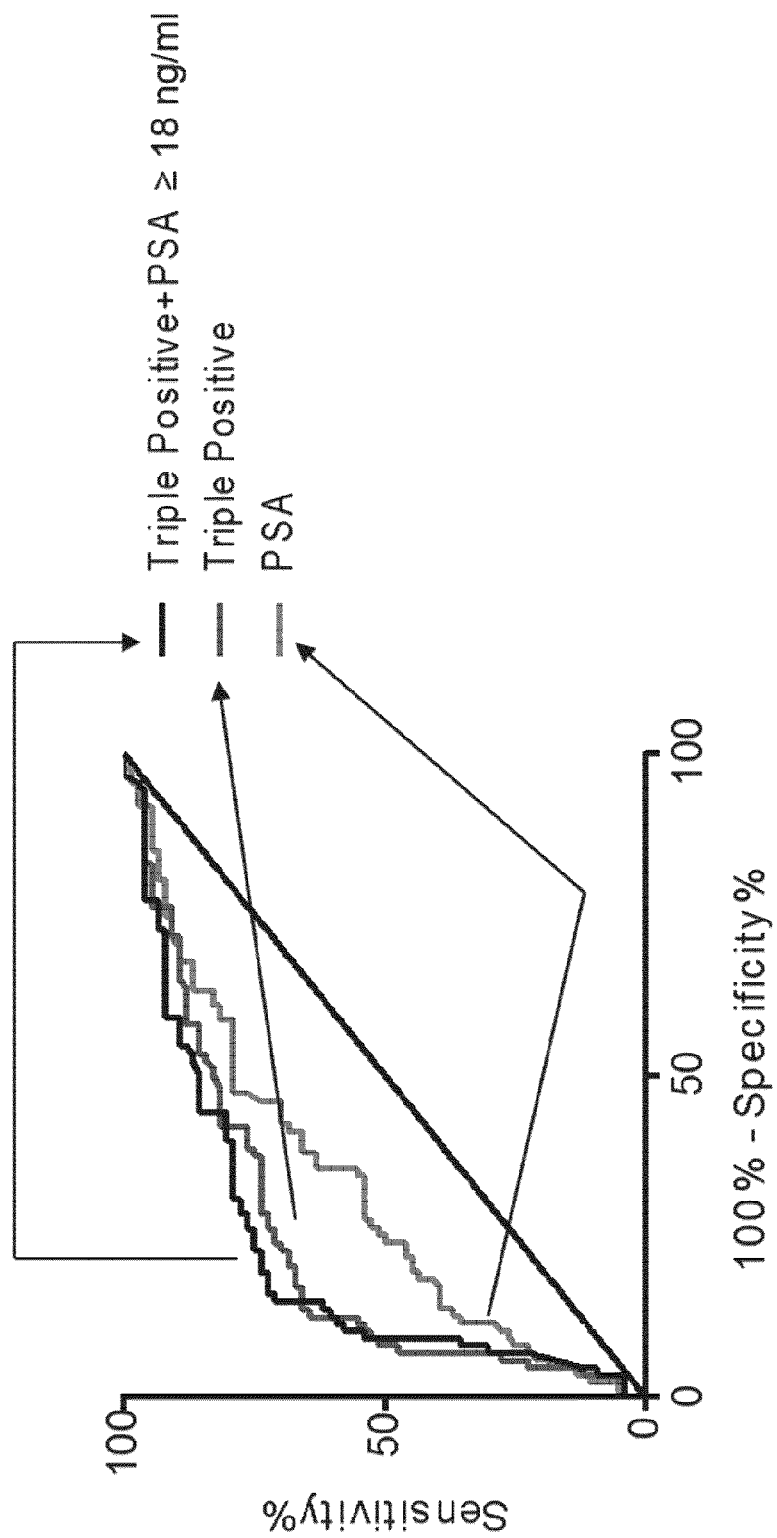

All individuals in the validation cohort had recorded PSA scores (Groups 1-5). PSA levels as a diagnostic test for discriminating high-risk prostate cancer (Groups 3-5) from low risk, or indolent, prostate cancer (Groups 1-2) using our validation cohort generated an AUC of 0.68 (95% CI: 0.60, 0.76) (FIG. 16A). A triple-positive extracellular vesicle test for discriminating Groups 1-2 from Groups 3-5 generated an AUC=0.77 (95% CI: 0.70, 0.84). Similar to our discovery cohort, PSA≥18 ng/ml had a very high Specificity (Specificity=96%), and by combining PSA≥18 ng/ml with our Triple-positive test, an AUC of 0.79 (CI: 0.72, 0.87) was generated. As with the discovery cohort, the test parameters were set to give a diagnosis of prostate cancer if triple-positive levels were ≥2000 events/µl or PSA was ≥18 ng/ml. A direct comparison of the false discovery rate (FDR) and true discovery rate (TDR) for these testing platforms found PSA testing at ≥4 ng/ml had a 69.5% FDR of cancer in low-risk groups and missed cancer in 13.3% of high-risk patients (FIG. 16B). A triple-positive extracellular vesicle test at ≥2000 events/µl had a 13% FDR of cancer and missed cancer in 28.3% of high-risk patients. The combination of PSA≥18 ng/ml and triple-positive extracellular vesicles as ≥2000 events/µl had a 15.5% FDR of cancer and missed cancer in 19.9% of high-risk patients.

Figure 17A:
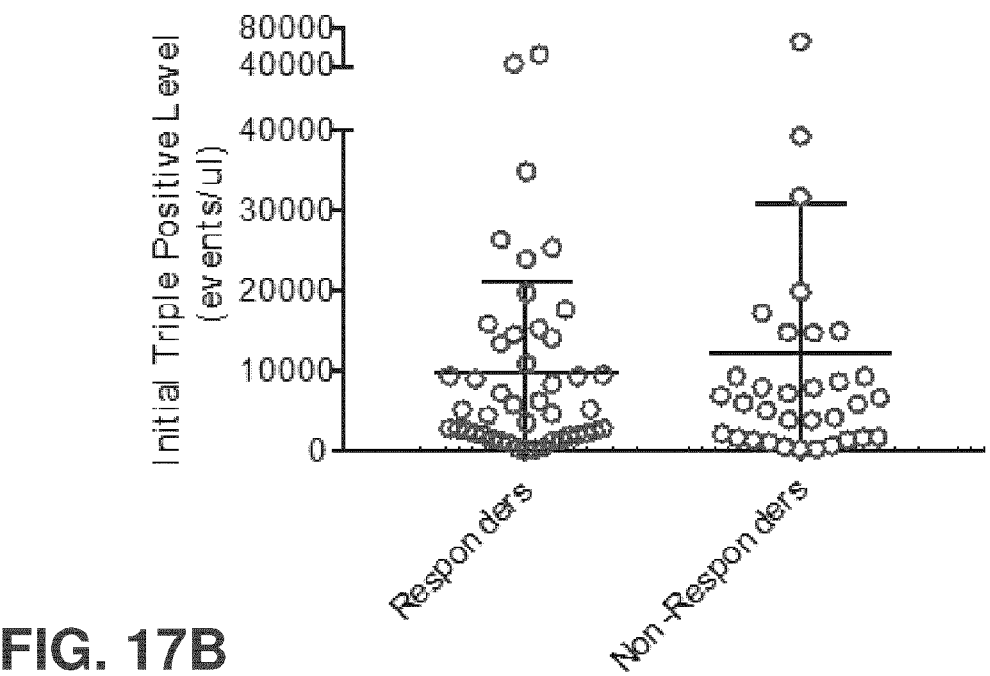
FIGS. 17A-17C are a series of graphs depicting metastatic patient triple-positive extracellular vesicle levels pre and post-treatment. Analysis of metastatic patient plasmas for polysialic acid-PSMA-STEAP1 extracellular vesicle levels were performed pre-treatment (FIG. 17A) and post-treatment (FIG. 17B). Post-treatment levels are represented as the total change in triple positive extracellular vesicle levels from pre-treatment levels. Post-treatment levels were grouped based on patient treatment (FIG. 17C). Asterisk denotes statistical significance ($p<0.05$). Data is shown as mean±standard deviation.
Figure 17B:
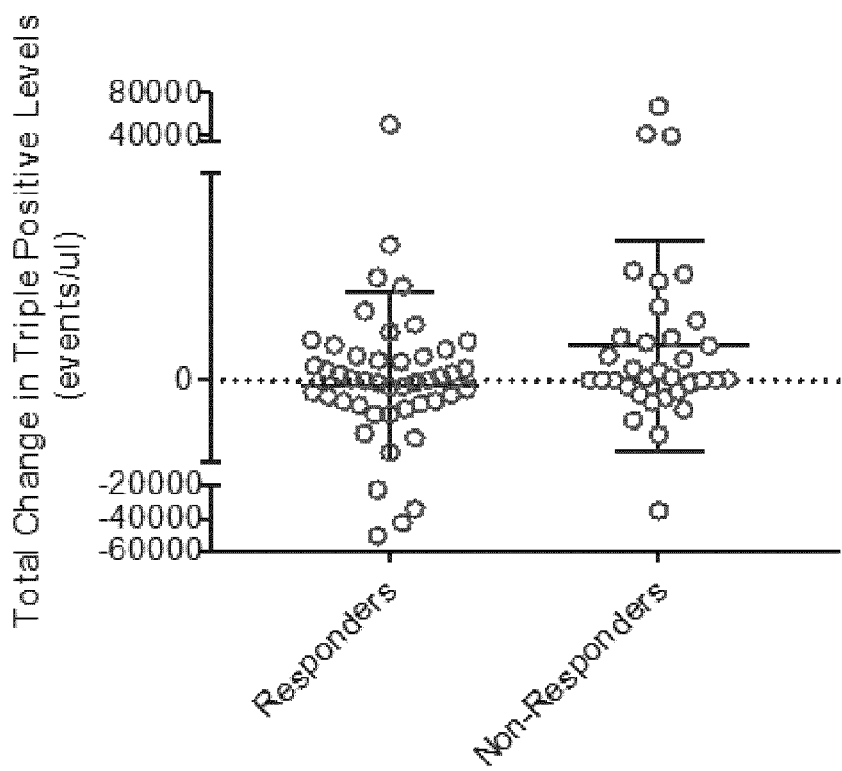
Figure 17C:
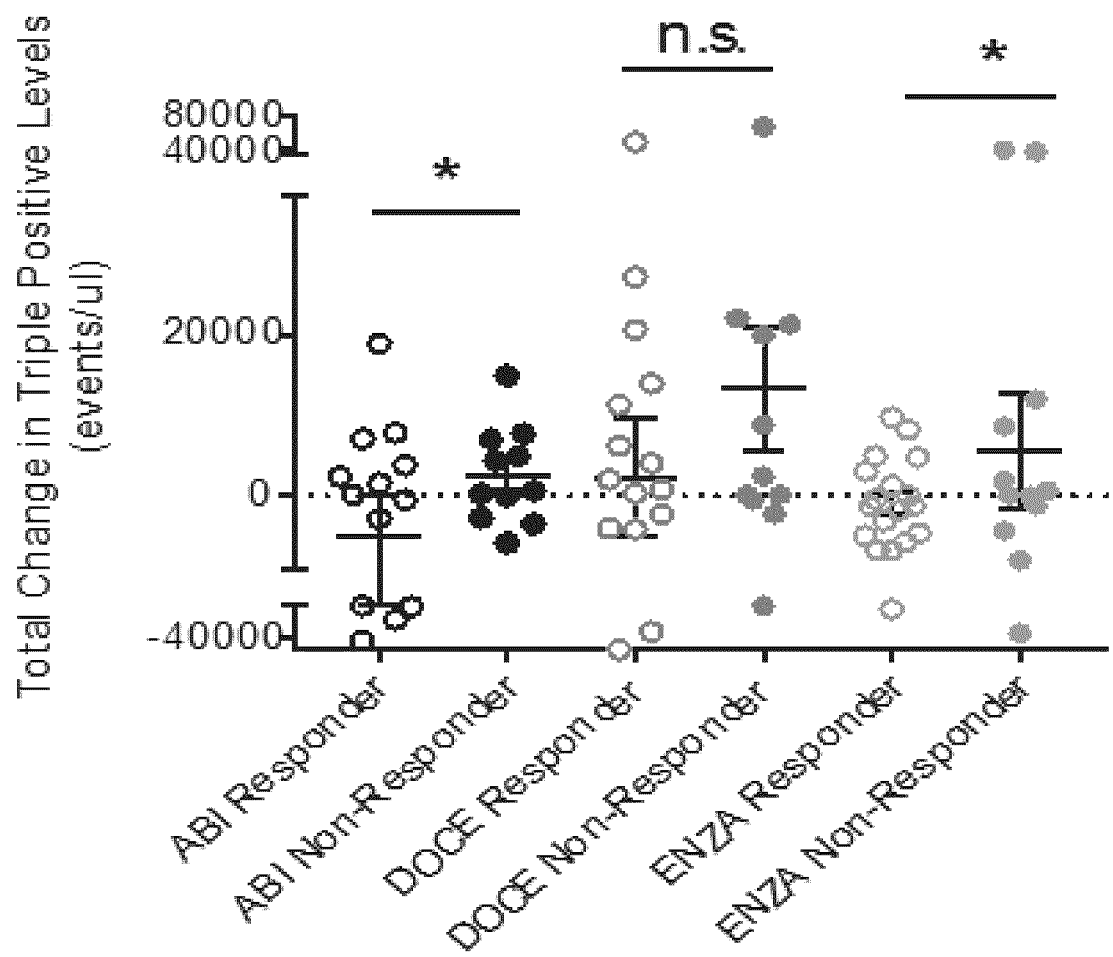

Example 16. PolySia-STEAP1-PSMA EV Levels in Metastatic Patients Pre and Post-Treatment A metastatic patient cohort, consisting of 80 patients with metastatic disease, was used to evaluate triple-positive polySia-STEAP1-PSMA extracellular vesicle levels pre- and post-treatment. Post-treatment patients were classified based on their treatment response as either responders or non-responders. Pre- and post-treatment plasmas were analyzed for triple-positive extracellular vesicles using nanoscale flow cytometry. There was no significant difference between pre-treatment triple-positive extracellular vesicles levels in responder (9658±1707) and non-responder groups (12038±3213) (FIG. 17A). Post-treatment plasma triple-positive extracellular vesicle levels were analyzed and results were represented as the total change in an individual's levels from pre-treatment to post-treatment. Results show a significant reduction in triple-positive extracellular vesicle levels for responders (−996±2239) compared to non-responders (6499±2625) (p=0.03) (FIG. 17B). As patients were treated with either abiraterone, docetaxel, or enzalutamide, we also analyzed each group individually for response to treatment. Abiraterone and enzalutamide treatment groups had significantly lower triple-positive levels in the responder group compared to the non-responders (p=0.0013 and p=0.03, respectively). However, no significant differences were found in the docetaxel responders versus non-responders (FIG. 17C).

Figure 20A:
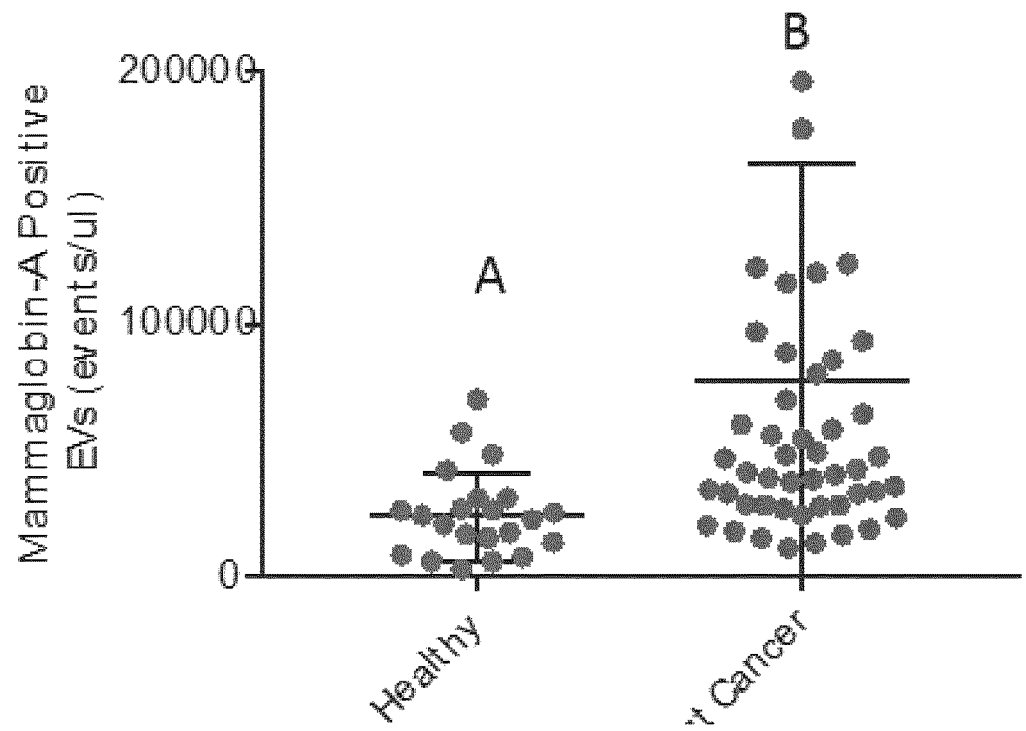
FIGS. 20A-20C are a series of graphs demonstrating that polySia-positive breast extracellular vesicles are increased in breast cancer patient plasmas. Seventy four plasma samples from 24 healthy and 50 breast cancer patients were analyzed by nanoscale flow cytometry and extracellular vesicle levels were graphed as the number of events per µl of sample. Tissue specific marker, Mammaglobin-A, was used to identify extracellular vesicles derived from breast tissue. Mammaglobin-A extracellular vesicles were found in healthy and breast cancer patient plasmas with significantly more events detected for breast cancer ($p<0.01$) (FIG. 20A). PolySia-Mammaglobin-A dual positive extracellular vesicles were elevated in breast cancer plasmas (FIG. 20B). There were significantly more events detected for breast cancer patient levels compared to healthy controls ($p<0.001$). Different letters represent statistically significant differences. The test parameters for a dual-positive extracellular vesicle test to detect breast cancer were determined using the area under receiver operating characteristic curve and found to have an AUC=0.92 (95% CI, 0.86-0.98) (FIG. 20C, upper line). Mammaglobin-A extracellular vesicle levels generated an AUC=0.80 (95% CI, 0.70, 0.91) (FIG. 20C, lower line). The diagonal line represents the reference line, AUC=0.5. CI=confidence interval.
Figure 20B:
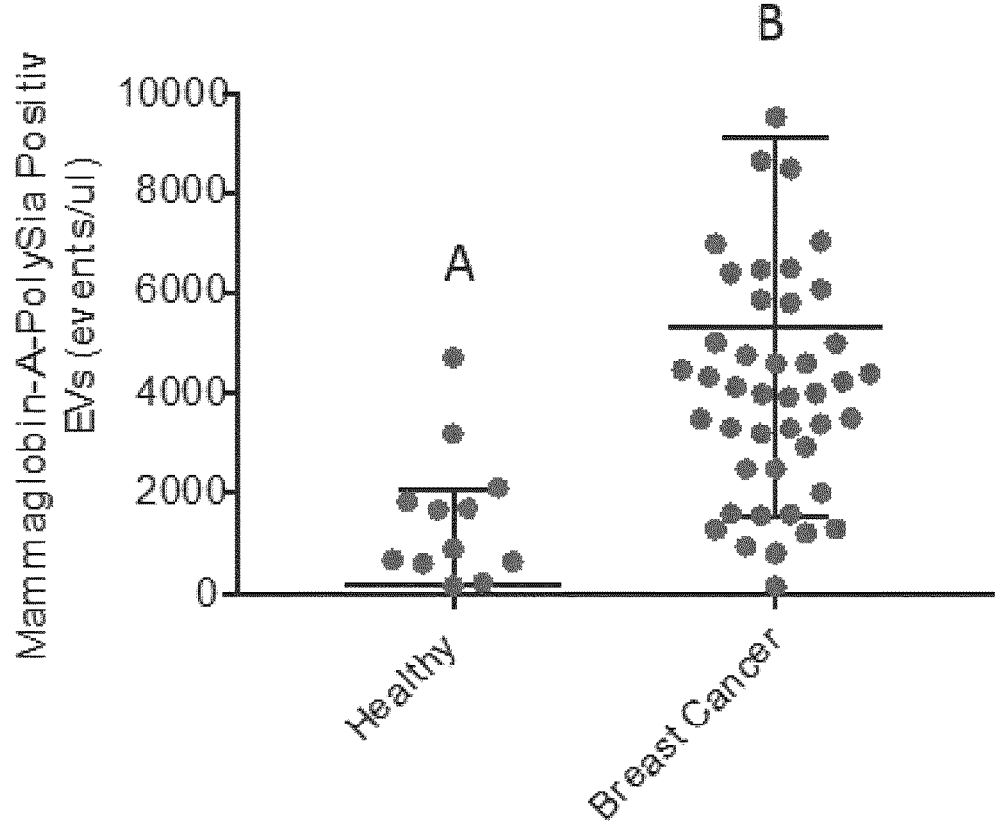
Figure 20C:
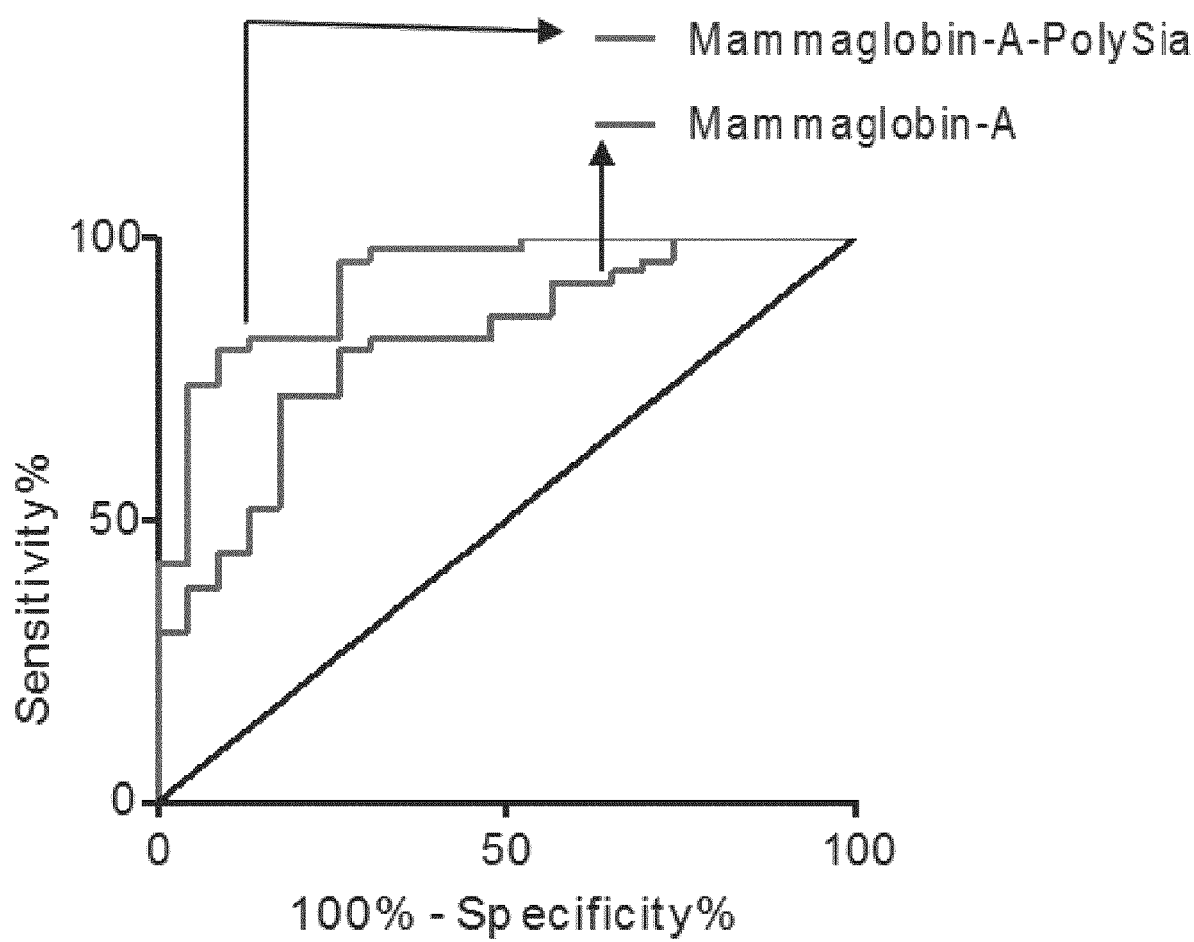
Figure 20D:
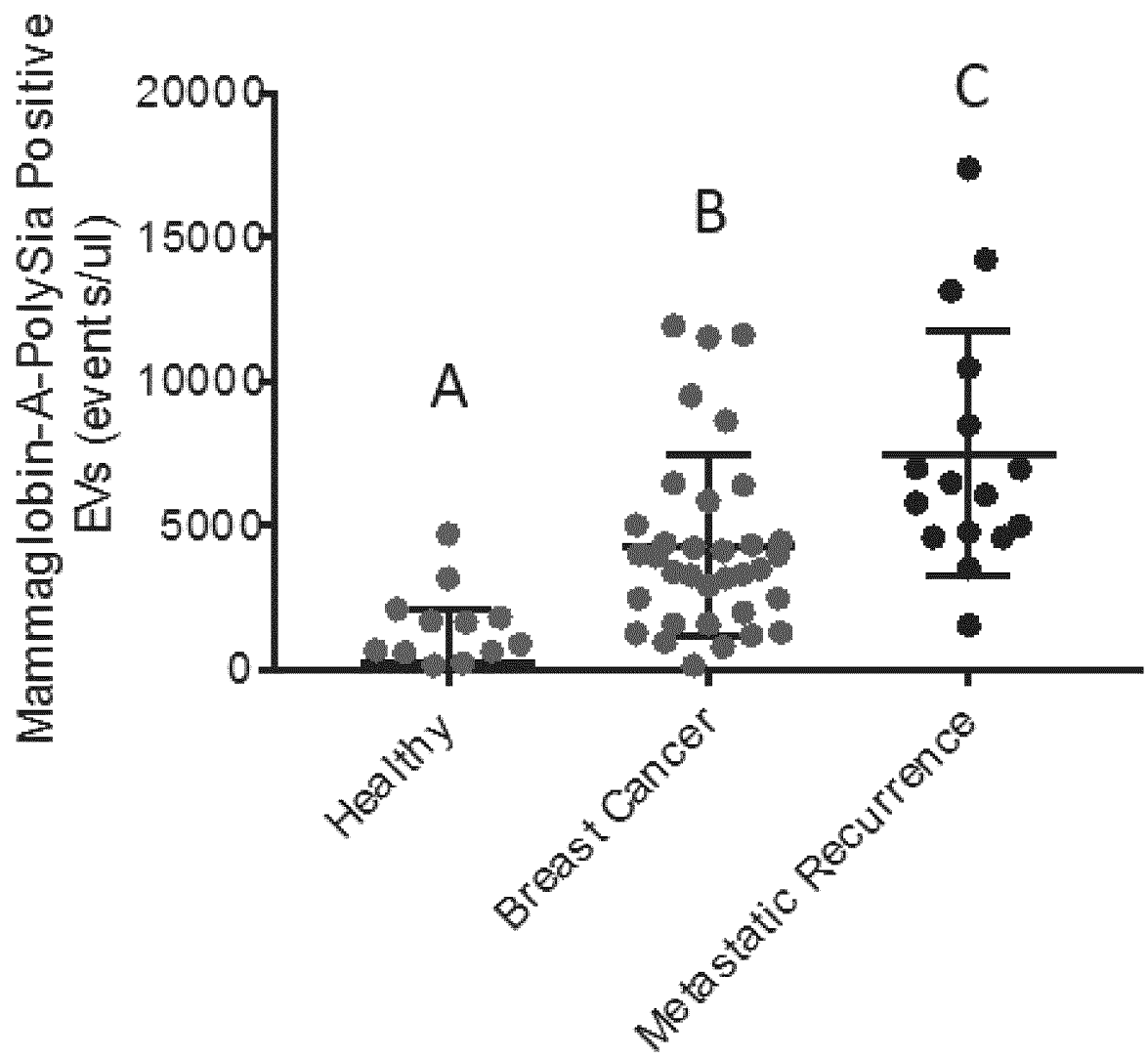
FIG. 20D is a graph demonstrating that Mammaglobin A-polySia dual positive extracellular vesicle levels identify women whose breast cancer will eventually recur. With the clinical follow-up data accompanying the breast cancer blood plasma specimens in FIGS. 20A-20B, patients were stratified into non-recurrent breast cancer (breast cancer) and recurrent breast cancer (metastatic recurrence). Dual-positive extracellular vesicle levels were plotted for each category and patients whose disease resulted in a recurrence had significantly elevated polySia-Mammaglobin-A extracellular vesicle levels present at the time of initial diagnosis compared to healthy volunteers ($p<0.0001$) and those whose disease did not recur ($p<0.01$) (FIG. 20D).

Example 17. Analysis of Plasma from 50 BCa Patients with Breast Cancer (Obtained at Baseline, Prior to Neoadjuvant Treatment) and 25 Healthy Volunteers Mammaglobin-A extracellular vesicles were detected in both healthy volunteers and BCa. Levels were significantly higher in BCa patients with a median value of 41,713 events/µl of plasma compared to 23,023 events/µl plasma (p<0.001) (FIG. 20A). Plasmas from healthy volunteers and BCa patients were analyzed for dual-positive mammaglobin-A-polySia positive extracellular vesicles. BCa patients were found to have significantly higher dual positive extracellular vesicles (p<0.0001) (FIG. 20B). To assess the clinical utility of mammaglobin-A-polySia dual positive levels to report on the presence of BCa, an ROC curve was generated and found to have an AUC of 0.925 with a 95% confidence interval of 0.86-0.98 (FIG. 20C). To determine if polySia-mammaglobin-A levels in patient plasma at baseline could be predictive of metastatic potential we assessed dual-positive levels in relation to a metastatic diagnosis during patient follow-up. BCa patients who developed metastatic disease were found to have significantly higher dual-positive extracellular vesicle levels compared to healthy volunteers and BCa patients who remained disease free after treatment (p<0.001) (FIG. 20D).

Example 18. Materials and Methods

Tissue-Microarray Production and Analysis.
The Vancouver Prostate Centre Pathology Core Predictive Tissue Microarray Series (VPC-PTMA) was built from 505 radical prostatectomies performed by the University of British Columbia, Department of Urologic Sciences surgical teams. The patients were therapy naïve at the time of surgery. Clinical data for these patients is available including pathologic grade, stage, serum PSA, lymph node status (LN) and distant metastasis history along with follow-up to time of PSA recurrence, or at least 5 years without PSA recurrence. The TMAs were constructed semi-automatedly using Pathology Devices' TMArrayer with attached Leica M50 stereo microscope by punching duplicate 1 mm cores of each specimen. The cores are scored based on the currently recommended ISUP Gleason grouping standards. Gleason Group scores reflect the normal distribution of scores with Group 1 (originally Gleason score 53+3) being 20%, Group 2 (originally Gleason score 3+4) being 20%, Group 3 (originally Gleason score 4+3) being 20%, and Groups 4 and 5 (originally Gleason score ≥4+4) being 10% each. The VPC-PTMA was designed to calculate PSA recurrence-free survival for biomarkers of interest. Consistent with this intent, recurrence-free survival (RCF) calculated for each Gleason Group based on pathologic grading by Kaplan-Meier analysis for relative time to recurrence, and as the total % recurrence indicate the expected increased risk of progression for each Gleason Group with Groups 1 and 2 having the most favorable prognosis, Groups 4 and 5 having the worse prognosis and Group 3 having an intermediate-risk. Positive control sections are human hippocampus tissue cores and ganglion tissue cores embedded randomly throughout the TMA. As optimized previously, a dilution of 1/100 is used with goat anti-mouse IgG-HRP and DAB as the secondary colorimetric based agent. A Ventana Autostainer (Ventana Inc.) was used for immunohistochemistry of the TMA sections. Scoring of TMAs is on a 0-3 scale (0=none, 1=minimal/patchy, 2=moderate, 3=high). After TMAs are scored, the data can be correlated with clinical outcomes (e.g., time to cancer recurrence, progression free survival, overall survival, skeletal related events).
Blood Collection:
Patient blood samples were obtained prior to transrectal ultrasound (TRUS)-based biopsy of the prostate or prior to breast biopsy. Two vacutainers (EDTA-K2 10 mL volume) were collected at least 30 minutes prior to biopsy, processed and plasma was stored at −80° C. until analysis.
Nanoscale Flow Cytometry:
Plasma was prepared from whole blood collected from localized prostate cancer or breast cancer patients prior to biopsy or surgery and stored at −80° C. Ethics to collect and use patient plasmas approved by the local REB board. 10 µL of plasma were each incubated with 1 µL of anti-PSMA-RPE, anti-STEAP1-Alexa647, and anti-polysialic acid-FITC in the dark for 30 minutes. The corresponding isotype controls were incubated with 10 µL of plasma. The samples were diluted in 1:30 in PBS then analyzed on the Apogee A50-Micro nanoscale flow cytometer (Apogee FlowSystems Inc., UK).
Demonstrating the sizing resolution of the apogee A50-micro nanoscale flow cytometer:
Three types of microspheres (silica, latex, liposomes) were analyzed using the A50-Micro Nanoscale Flow Cytometer (Apogee FlowSystems Inc.), and the CytoFlex (Beckman Coulter, Inc. Silica beads were purchased from Apogee FlowSystems Inc. Latex beads (100 nm, 200 nm, 500 nm and 1 µm Tetraspek beads; LifeTechnologies Inc.) were diluted 1:10000 prior to analysis on the A50-Micro Nanoscale Flow Cytometer.
Intravital Imaging of Extracellular Vesicle Release:
PC3MLN4 cells were incubated with GFP-EndoNDM for 30 min and cells were labeled with CellTracker-Red. The cells were extensively washed and injected into a vein within the choriallonic membrane (CAM) of a 13 day old avian embryo. Two hours post-cell injection, embryos were injected with 649-DyeLight, a lectin which binds to the stromal cells. Real-time imaging of cells in the vasculature of the CAM was performed using confocal microscopy.
Characterization of polySia Expression on Extracellular Vesicles Generated from an Aggressive Prostate Cancer Cell Line:
PC3MLN4 cells were plated on T25 flasks at 60% confluence. Cells were grown for 24 hrs in minimal media, OPTI-MEM, without FBS. Media was collected and centrifuged at 200×g for 5 min to remove unbroken cells. The supernatant was reserved, aliquoted, and stored at −80° C. To detect prostate polysialylated extracellular vesicles, 1 µL of anti-polySia was added to 20 µL of suspended extracellular vesicles and incubated at room temperature for 10 minutes in the dark. Samples were then diluted in 1:7 in PBS and analyzed on the flow cytometer.
Super Resolution Confocal Microscopy:
Plasma samples were prepared as described for nanoscale flow cytometry. Briefly, plasma samples were incubated with antibodies for STEAP1, PSMA and polySia. Plasma was washed with 300 ul of PBS and dried on coverslips. Dried coverslips were inverted on a drop of Prolonged Antifade or DAKO mounting media and imaged using super resolution microscopy.

Example 19. Treatment of a Subject with Prostate Cancer Using a Liquid Biopsy

According to the methods disclosed herein, a physician of skill in the art can treat a patient, such as a human patient with cancer (e.g., prostate cancer), so as to inhibit cancer growth, reduce tumor burden, increase cancer cell death, or slow disease progression. The method of treatment can include risk-stratifying the subject's cancer to determine the best course of treatment. For example, a blood sample can be collected from the subject, and prostate cancer extracellular vesicles in the blood sample can be evaluated for expression of polySia, PSMA, and STEAP1 using nanoscale flow cytometry. A subject having over 2,000 triple-positive events/µl is determined to have high-risk cancer. This determination can be made by the physician, or can be made by a laboratory technician prior to the subject's visit with the physician. Based on the liquid biopsy results indicating that the subject has high-risk prostate cancer, the physician can treat the subject using an aggressive therapy (e.g., radical prostatectomy or radiation therapy). Additional liquid biopsies can be performed (e.g., performed by the physician or performed by a laboratory technician and used by the physician) during or after treatment to evaluate treatment efficacy. A finding that the number of triple-positive events per microliter has decreased by 5% or more (e.g., 5%, 10%, 20%, 30%, 40%, 50%, 60%, 70%, 80%, 90% or more) during or after treatment indicates that the treatment is effective in reducing tumor burden in the subject. A finding that the number of triple-positive events per microliter is unchanged or has increased during or after treatment indicates that the treatment has not been successful in treating the cancer and that an additional round of treatment or different treatment option should be selected for the subject.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of diagnosing prostate cancer in a subject, the method comprising:
   providing a subject identified as having at least 2,000 prostate cancer extracellular vesicles that are triple-positive for polySia, STEAP1, and PSMA per microliter of biological sample; and
   performing a prostate needle-core biopsy on the subject.

2. The method of claim 1, wherein the biological sample is blood, blood plasma, urine, or semen.

3. The method of claim 1, wherein the number of triple-positive extracellular vesicles was measured using nanoscale flow cytometry.

4. The method of claim 1, wherein the method further comprises treating the subject with an aggressive therapy.

5. The method of claim 1, wherein the method is performed to obtain additional diagnostic information after the subject has received inconclusive results from magnetic resonance imaging of the prostate.

6. The method of claim 1, wherein the subject has been found to have a prostate specific antigen level of >2 to <18 ng/ml.

* * * * *